US012807949B2

(12) United States Patent
Raymond et al.

(10) Patent No.: US 12,807,949 B2
(45) Date of Patent: Nov. 24, 2026

(54) INDUCIBLE ANTI-SENSE REPRESSOR SWITCHES AND USES THEREOF

(71) Applicant: Trustees of Boston University, Boston, MA (US)

(72) Inventors: Michael Howard Raymond, Dorchester, MA (US); Ahmad S. Khalil, Lexington, MA (US)

(73) Assignee: Trustees of Boston University, Boston, MA (US)

( * ) Notice: Subject to any disclaimer, the term of this patent is extended or adjusted under 35 U.S.C. 154(b) by 228 days.

(21) Appl. No.: 18/450,168

(22) Filed: Aug. 15, 2023

(65) Prior Publication Data

US 2024/0110185 A1 Apr. 4, 2024

Related U.S. Application Data

(60) Provisional application No. 63/398,071, filed on Aug. 15, 2022, provisional application No. 63/454,508, filed on Mar. 24, 2023.

(51) Int. Cl.
*C12N 15/113* (2010.01)
*C12N 15/63* (2006.01)

(52) U.S. Cl.
CPC ............ *C12N 15/113* (2013.01); *C12N 15/63* (2013.01); *C12N 2310/11* (2013.01)

(58) Field of Classification Search
CPC .... C12N 15/113; C12N 15/63; C12N 2310/11
See application file for complete search history.

(56) References Cited

U.S. PATENT DOCUMENTS

| | | | |
|---|---|---|---|
| 5,034,506 | A | 7/1991 | Summerton et al. |
| 5,235,033 | A | 8/1993 | Summerton et al. |
| 6,444,871 | B1 | 9/2002 | Yeo |
| 10,138,493 | B2 | 11/2018 | Khalil et al. |
| 10,590,182 | B2 | 3/2020 | Lim et al. |
| 11,530,246 | B2 | 12/2022 | Khalil et al. |
| 2009/0311788 | A1 | 12/2009 | Pachuk et al. |
| 2014/0234851 | A1 | 8/2014 | Leonard et al. |
| 2019/0233844 | A1 | 8/2019 | Lu et al. |
| 2020/0002710 | A1 | 1/2020 | Khalil et al. |
| 2020/0377564 | A1 | 12/2020 | Khalil et al. |

FOREIGN PATENT DOCUMENTS

| | | | | |
|---|---|---|---|---|
| CA | 3138576 A1 * | 11/2020 | | ............ A61K 35/17 |
| WO | 2002088346 A2 | 11/2002 | | |
| WO | 2022032397 A1 | 2/2022 | | |

OTHER PUBLICATIONS

Alerasool "An efficient KRAB domain for CRISPRi applications in human cells" Nature Methods (2020) 17: 1093-1096. (Year: 2020).*

Bennett "RNA Targeting Therapeutics: Molecular Mechanisms of Antisense Oligonucleotides as a Therapeutic Platform" Annu. Rev. Pharmacol. Toxicol. (2010) 50: 259-93 (Year: 2010).*

Wu "Reversible immortalization of rat pancreatic cells with a novel immortalizing and tamoxifen-mediated self-recombination tricistronic vector" Journal of Biotechnology (2011) 101: 231-241. (Year: 2011).*

Fussenegger et al. "pTRIDENT, a Novel Vector Family for Tricistronic Gene Expression in Mammalian Cells" Biotechnol Bioeng ( 1998) 57: 1-10. (Year: 1998).*

Chery et al. "RNA therapeutics: RNAi and antisense mechanisms and clinical applications" Postdoc J. (2016); 4(7): 35-50. (Year: 2016).*

Li et al. Science 378 1227-1234 (Year: 2022).*

Berg "Proposed structure for the zinc-binding domains from transcription factor IIIA and related proteins." Proceedings of the National Academy of Sciences 85.1: 99-102 (1988).

Bintu "Dynamics of epigenetic regulation at the single-cell level." Biophysical Journal 110.3: 317a-318a (2016).

Bogenhagen "Proteolytic footprinting of transcription factor TFIIIA reveals different tightly binding sites for 5S RNA and 5S DNA." Molecular and cellular biology (1993).

Brandl et al. "Hydrogel-based drug delivery systems: Comparison of drug diffusivity and release kinetics." Journal of Controlled Release 142.2: 221-228 (2010).

Cardillo et al. "Interleukin-6, interleukin-10 and heat shock protein-90 expression in renal epithelial neoplasias and surrounding normal-appearing renal parenchyma." International journal of immunopathology and pharmacology 20.1: 37-46 (2007).

Chavez et al. "Highly efficient Cas9-mediated transcriptional programming." Nature methods 12.4: 326-328 (2015).

Csermely et al. "The 90-KDa molecular chaperone family: structure, function, and clinical applications. A comprehensive review." Pharmacology & therapeutics 79.2: 129-168 (1998).

Daringer et al. "Modular extracellular sensor architecture for engineering mammalian cell-based devices." ACS synthetic biology 3.12: 892-902 (2014).

Deuschle et al. "Tetracycline-reversible silencing of eukaryotic promoters." Molecular and cellular biology (1995).

Easton et al. "The Hsp110 and Grp170 stress proteins: newly recognized relatives of the Hsp70s." Cell stress & chaperones 5.4: 276 (2000).

Gatz et al. "Stringent repression and homogeneous de-repression by tetracycline of a modified CaMV 35S promoter in intact transgenic tobacco plants." The Plant Journal 2.3: 397-404 (1992).

(Continued)

*Primary Examiner* — Brian Whiteman
(74) *Attorney, Agent, or Firm* — Nixon Peabody LLP; Ronald I. Eisenstein; Alissa R. Young

(57) ABSTRACT

The methods and compositions described herein are directed to regulated synthetic gene expression systems. In particular, the technology described herein relates to compositions, systems and methods for inducible and transient (e.g., reversible) transcriptional repression of a target transcript of interest (GOI). The methods, compositions and systems described herein relate to engineered synthetic transcription factors (synTF) that are activated by an inducer molecule, which induces the transcription of a repressor or gene editing molecule from a synthetic inducible repressor constructs where the antisense repressor (or gene editing molecule) mediates reversible repression of a target transcript of interest (GOI) in the presence of the inducer.

30 Claims, 11 Drawing Sheets

Specification includes a Sequence Listing.

(56) References Cited

OTHER PUBLICATIONS

Gazit et al. "De-regulation of GRP stress protein expression in human breast cancer cell lines." Breast cancer research and treatment 54: 135-146 (1999).
Gossen et al. "Tight control of gene expression in mammalian cells by tetracycline-responsive promoters." Proceedings of the National Academy of Sciences 89.12: 5547-5551 (1992).
Hilton et al. "Epigenome editing by a CRISPR-Cas9-based acetyltransferase activates genes from promoters and enhancers." Nature biotechnology 33.5: 510-517 (2015).
Khalil et al. "A synthetic biology framework for programming eukaryotic transcription functions." Cell 150.3: 647-658 (2012).
Larson et al. "CRISPR interference (CRISPRi) for sequence-specific control of gene expression." Nature protocols 8.11: 2180-2196 (2013).
Lee et al. "Three-dimensional solution structure of a single zinc finger DNA-binding domain." Science 245.4918: 635-637 (1989).
Mackay et al. "Zinc fingers are sticking together." Trends Biochem Sci 23: 1-4 (1998).
Magari et al. "Pharmacologic control of a humanized gene therapy system implanted into nude mice." The Journal of clinical investigation 100.11: 2865-2872 (1997).
Miller et al. "Repetitive zinc-binding domains in the protein transcription factor IIIA from Xenopus oocytes." The EMBO journal 4.6: 1609-1614 (1985).
Ohtsuka et al. "Molecular chaperone function of mammalian Hsp70 and Hsp40-a review." International Journal of Hyperthermia 16.3: 231-245 (2000).
Park et al. "Engineering epigenetic regulation using synthetic read-write modules." Cell 176.1: 227-238 (2019).
Searles et al. "The role of the central zinc fingers of transcription factor IIIA in binding to 5 S RNA." Journal of molecular biology 301.1: 47-60 (2000).
Sirin et al. "Regulating gene expression using self-inactivating lentiviral vectors containing the mifepristone-inducible system." Gene 323: 67-77 (2003).
Strik et al. "Heat shock protein expression in human gliomas." Anticancer research 20.6B: 4457-4462 (2000).
Szewczenko-Pawlikowski, et al. "Heat shock-regulated expression of calreticulin in retinal pigment epithelium." Molecular and cellular biochemistry 177: 145-152 (1997).
Vora et al. "Rational design of a compact CRISPR-Cas9 activator for AAV-mediated delivery." BioRxiv: 298620 (2018).
Yeo et al. "An enhanced CRISPR repressor for targeted mammalian gene regulation." Nature methods 15.8: 611-616 (2018).
Yu et al. "Identification of differentially expressed proteins between human hepatoma and normal liver cell lines by two-dimensional electrophoresis and liquidchromatography-ion trap mass spectrometry." Electrophoresis: An International Journal 21.14: 3058-3068 (2000).

* cited by examiner

Inducible Anti-Sense Repressor Design

SynTF:

Synthetic inducible repressor - circuit:

FIG. 4A
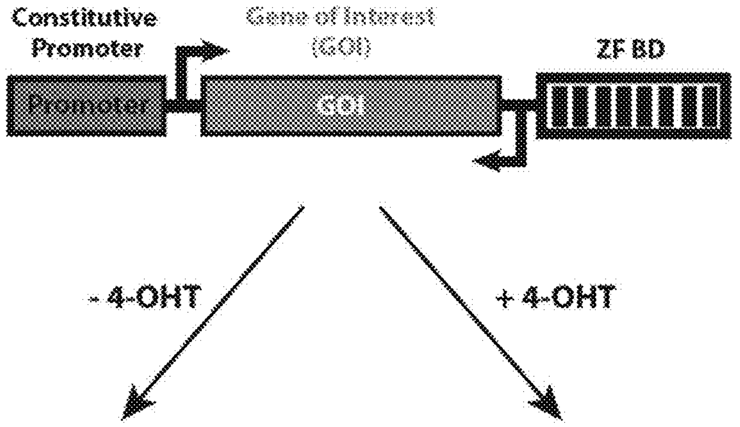
FIG. 4B
FIG. 4C
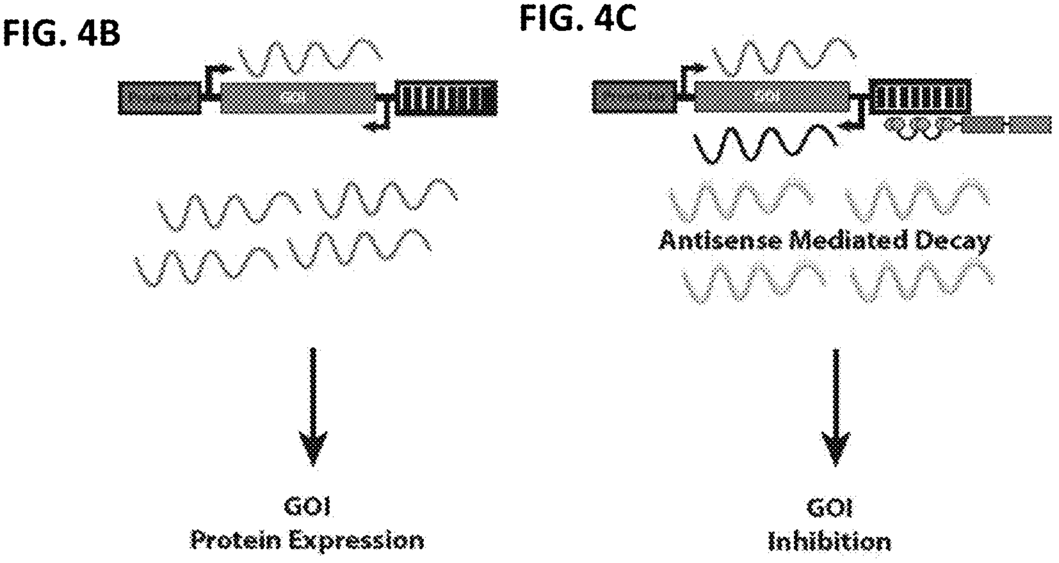

Inducible anti-sense repressor reversibly silenced the GOI (or TNA)

Conditions:
- 293T Cells
- Induce (1uM) 4OHT
- Induce 1d, 2d, 3d
- Recovery 2d, 4d, 6d, 8d

Downstream Inducible Repressor Design

Anti-sense Repressor Displays Mild Repression

Conditions:
- 293T Cells
- Induce: 1D, 2D, 3D Recover: 2D, 4D

Anti-sense Repressor With Spacer Displays Greater Repression

Conditions:
- 293T Cells
- Induce: 1D, 2D, 3D Recover: 2D, 4D

Anti-sense Repressor With Spacer Representative Flow Plot

Inducible Anti-Sense Repressor Design

Short Anti-sense Repressor Displays Greater Repression

Conditions:
- 293T Cells
- Induce: 1D, 2D, 3D Recover: 2D, 4D

INDUCIBLE ANTI-SENSE REPRESSOR SWITCHES AND USES THEREOF

CROSS REFERENCE TO RELATED APPLICATIONS

This application claims benefit under 35 U.S.C. § 119(e) of U.S. Provisional Application No. 63/398,071, filed Aug. 15, 2022 and U.S. Provisional Application No. 63/454,508, filed Mar. 24, 2023, the contents of each of which are incorporated herein by reference in their entireties.

SEQUENCE LISTING

The instant application contains a Sequence Listing which has been submitted electronically in XML format and is hereby incorporated by reference in its entirety. Said XML copy, created on Aug. 15, 2023, is named "701586-192620WOPT_SL.xml" and is 74,503 bytes in size.

TECHNICAL FIELD

The technology described herein relates to regulated synthetic gene expression systems. The present technology relates to compositions, systems, and methods for inducible and transient (e.g., reversible) transcriptional repression of a target transcript of interest. Engineered inducible synthetic transcription factors (synTF) and synthetic gene constructs are used to mediate reversible repression of a target transcript of interest present in the synthetic gene construct.

BACKGROUND

Precise regulation of therapeutic gene expression in a cell-based therapeutic or gene therapy is a central approach to the treatment of many genetic disorders. Achieving this goal fundamentally requires engineered regulatory elements and circuitry that can be used to program the cell in order to precisely regulated expression of therapeutic agents. Typically, promoters such as inducible promoters etc. and other nucleic regulatory elements (e.g., enhancers) are used. Towards this goal, synthetic transcriptional programs and circuits can be used with response modules to enable new layers of regulation in cells.

Synthetic transcriptional circuits have advanced the capabilities and safety of cell-based therapeutics and gene therapy. In particular, although there are reports of synthetic transcriptional circuits that function as synthetic transcriptional repressor systems, e.g., Alerasool et al., 2020, Nat Methods, and Larson, et al., Nat Protoc 8, 2180-2196 (2013), these transcriptional repressor systems are not transient reversible systems.

Recent technologies using synthetic regulatory systems, can use, for example, engineered proteins that target responsive promoters to conditionally induce or silence therapeutic gene expression. It has importantly been demonstrated that first-generation therapeutic delivery systems are functional and clinically viable strategies capable of achieving long-term regulation in primates. Non-limiting examples of some first-generation therapeutic delivery systems include simple, zinc finger containing transcription factors to induce therapeutic gene expression.

However, there are fundamental limitations to certain families of synthetic regulatory proteins that prevent their widespread adoption in gene therapies. For example, certain classes of programmable DNA-targeting domains (Transcription Activator Like Effector (TALE) and CRISPR/ dCas9) are derived from prokaryotic systems, rendering them likely to be immunogenic in a human therapy context. Additionally, these proteins are large and approach the packaging limits of traditional lentiviral delivery schemes, preventing ease of delivery and addition of other useful molecular components.

SUMMARY

The technology described herein relates, in general, to an anti-sense inducible-repressor system or synthetic gene circuit that functions as an inducible, and reversible, repressor of a target nucleic acid (TNA) (also referred to herein as a GOI or transgene) that is also present on the synthetic inducible-repressor construct. In particular, the technology described herein relates to compositions, systems and methods for inducible and transient (e.g., reversible) transcriptional repression of a target transcript of interest (e.g., a target nucleic acid (TNA)), and uses an inducible synthetic transcription factor (synTF) to mediate reversible repression of a target transcript of interest.

Without wishing to be bound by theory, the inventors have developed a synthetic circuit system to advance the precision and tunability of synthetic gene circuits, which is based on the use of an inducible mRNA anti-sense repressor switch or 'off switch'. More specifically, using a synthetic transcription factor (synTF) comprising a human genome orthogonal zinc-finger array and a drug-inducible translocation system, the inventors are able to achieve robust and temporary repression of a transgene of interest (GOI), also referred to herein as a target nucleic acid or TNA. The inventors herein have developed a synthetic gene circuit which functions as a synthetic repressor system, and is an improvement over existing synthetic repressor systems or circuits in that it is unique due to its ability to control the gene repression of the transgene of interest with small molecules, as well as being transient and reversible gene repression.

Moreover, the inventors have developed a small-molecule inducible transcriptional repressor system which is able to robustly and transiently silence transgene expression (e.g., a transgene of interest, or TOI) in mammalian cells. Without wishing to be bound by theory, as a proof of principal a small-molecule inducible transcriptional repressor system disclosed herein works as follows: in the absence of the inducer molecule (e.g., 4-OHT), the ERT2 keeps the anti-sense repressor in the cytoplasm (FIG. 4B). However, in the presence of 4-OHT, the ERT2 domain shuttles the anti-sense repressor to the nucleus where it binds to the zinc finger binding domain (ZF BD) and induces transcription of anti-sense mRNA to the gene of interest (GOI) (FIG. 4C) The anti-sense transcript mediates decay and repression of the GOI (FIG. 4C).

In some embodiments, the inducible antisense repressor construct design is comprised of two units, a first transcription unit and a second transcription unit. First, to construct the small-molecule induced anti-sense transcriptional switch, an artificial zinc finger protein, as disclosed in U.S. Pat. No. 10,138,493 B2 and Patent Application No. US 2020/0377564 A1, which are incorporated herein in their entirety was attached to both a VP64 transcriptional domain and ERT2 domain (FIG. 2A). To assess transcriptional repression, a constitutively expressed mCherry fluorescent reporter was used and was appended to an inverted zinc finger binding array and minimal promoter (FIG. 2B).

To evaluate the kinetics of this repressor switch, 293T cells where generated to stably express both the inducible anti-sense repressor and fluorescent reporter. In order to determine whether the repressor switch is able to transiently silence GOIs, the inventors treated reporter cells with. 1 uM 4-OHT and measured mCherry reporter fluorescence at 1 day, 2 days, and 3 days. In order to determine whether the repressor switch transiently represses GOIs, the inventors removed 4-OHT and measured fluorescence expression after 2 days, 4 days, 6 days, and 8 days (FIG. 5A-5B). The inventors discovered that the reporter fluorescence expression is strongly repressed after 3 days and restored 8 days post 4-OHT removal, demonstrating the anti-sense repressor circuit functioned as a robust and transient repression system.

Accordingly, in one aspect as described herein is an engineered genetic construct comprising a heterologous nucleic acid construct comprising, in the 5' to 3' direction; a first transcription module comprising: a first promoter, a nucleotide sequence encoding a target nucleic acid (TNA) operatively linked to the first promoter; and a second transcriptional module, comprising: a second promoter in the antisense direction to the first promoter, a DNA binding motif (DBM) orientated in the antisense direction to the GOI, the DBM comprising a target nucleic acid for binding of the at least one DBD of a synthetic transcription factor (synTF), the SynTF comprising: at least one DNA-binding domain (DBD), at least one Transcription activation (TA) domain, and at least one nuclear localization domain, wherein the nuclear localization domain sequesters the synTF in the cytosol in the absence of an inducer, and in the presence of an inducer, the nuclear localization domain moves to the cytosol in the presence of the inducer.

In one embodiment of this and all other aspects described herein, the second transcriptional module further comprises a SynTF-mediated nucleic acid sequence (SynTF-MNAS), wherein the SynTF-MNAS is operatively linked to the second promoter and encodes at least one antisense nucleic acid sequence directed against at least a portion of the TNA, and wherein the SynTF-MNAS is located 3' of the TNA and 5' of the second promoter. In another embodiment of this and all other aspects described herein, the antisense nucleic acid sequence is selected from any of: a RNAi molecule, shRNA, siRNA, and miRNA.

In another embodiment of this and all other aspects described herein, the second transcriptional module further comprises a SynTF-mediated nucleic acid sequence (SynTF-MNAS), wherein the SynTF-MNAS is operatively linked to the second promoter and encodes a nucleic acid sequence that encodes a single stranded RNA (ssRNA) molecule that hybridizes with at least a portion of the target nucleic acid sequence to form a double stranded RNA molecule (dsRNA), wherein the dsRNA molecule comprises at least one nucleic acid change as compared to the nucleic acid sequence of the TNA.

In another embodiment of this and all other aspects described herein, the engineered genetic construct further comprising a Ribosome entry (RZ) site located 3' of the TNA and 5' of the second promoter sequence.

In another embodiment of this and all other aspects described herein, the first and second promoters are selected from any of: constitutive promoters, inducible promoters or tissue specific promoters. In another embodiment of this and all other aspects described herein, the first and second promoters are selected from a group consisting of SV40, CMV, UBC, EF1A, PGK and CAGG.

In another embodiment of this and all other aspects described herein, the first and second promoters are the same promoter. In another embodiment of this and all other aspects described herein, the first and second promoters are different promoters.

In another embodiment of this and all other aspects described herein, the DBD is selected from a group consisting of helix-turn-helix domain, zinc-finger binding domain, leucine zipper, winged helix domain, winged helix-turn-helix domain, helix-loop-helix domain, HMG-box domain, Wor3 domain, or OB-fold domain. In another embodiment of this and all other aspects described herein, the DBD is a zinc-finger binding domain. In another embodiment of this and all other aspects described herein, the TA domain is selected from a group consisting of acidic domains, glutamine-rich domains, proline-rich domains, and isoleucine-rich domains.

In another embodiment of this and all other aspects described herein, the TA domain is selected from acidic domains. In another embodiment of this and all other aspects described herein, the TA domain is VP64.

In one embodiment of this and all other aspects described herein, the nuclear localization domain is ERT2. In one embodiment of this and all other aspects described herein, the inducer is 4-OHT.

In another aspect as described herein is a vector comprising the engineered genetic construct of any of the embodiments described herein.

In one embodiment of this and all other aspects described herein, the vector further comprising a third promoter operatively linked to a heterologous nucleic acid encoding a synthetic transcription factor (synTF), wherein the synTF comprises; at least one DNA-binding domain (DBD), at least one Transcription activation (TA) domain, and at least one nuclear localization domain, and wherein when the synTF is expressed, the nuclear localization domain sequesters the synTF in the cytosol in the absence of an inducer, and wherein in the presence of an inducer, the nuclear localization domain moves to the cytosol in the presence of the inducer.

In another embodiment of this and all other aspects described herein, the third promoter is selected from any of: constitutive promoters, inducible promoters or tissue specific promoters.

In another embodiment of this and all other aspects described herein, the third promoter is selected from a group consisting of SV40, CMV, UBC, EF1A, PGK and CAGG. In another embodiment of this and all other aspects described herein, the first, second, and third promoters are the same promoter.

In another embodiment of this and all other aspects described herein, the first, second, and third promoters are different promoters. In another embodiment of this and all other aspects described herein, the inducer is 4-OHT. In another aspect as described herein is a cell comprising the engineered construct or the vector of any of the embodiments as described herein.

In one embodiment of this and all other aspects described herein, the cell further comprises at least one synthetic transcription factor (synTF), or a nucleic acid construct encoding a synTF, wherein the synTF comprises; at least one DNA-binding domain (DBD), at least one Transcription activation (TA) domain, and at least one nuclear localization domain, wherein the nuclear localization domain sequesters the synTF in the cytosol in the absence of an inducer, and wherein in the presence of an inducer, the nuclear localization domain moves to the cytosol in the presence of the inducer.

In another embodiment of this and all other aspects described herein, the inducer is 4-OHT.

In another aspect as described herein is a composition comprising then engineered genetic construct, the vector, or the cell of any of the embodiments as described herein.

In another aspect as described herein is a system for regulating the expression of a target nucleic acid sequence (TNA) comprising: a synthetic transcription factor (synTF) comprising: at least one DNA-binding domain (DBD), at least one Transcription activation (TA) domain, and at least one nuclear localization domain, wherein the nuclear localization domain sequesters the synTF in the cytosol in the absence of an inducer, and wherein in the presence of an inducer, the nuclear localization domain moves to the cytosol in the presence of the inducer; and an engineered genetic construct comprising, in the 5' to 3' direction a first transcription module and a second transcription module, the first transcription module comprising: a first promoter and a nucleotide sequence encoding a target nucleic acid sequence (TNA) operatively linked to the first promoter, and the second transcriptional module, comprising: second promoter in the antisense direction to the first promoter, a DNA binding motif (DBM) orientated in the antisense direction to the TNA, wherein the DBM comprises a target nucleic acid for binding of the at least one DBD of the SynTF; wherein, in the absence of the inducer, the synTF is sequestered in the cytosol, preventing the DBD of the synTF from binding to the DBM, and preventing the TA domain from being in proximity to the second promoter sequence, preventing repression of the TNA ("antisense-OFF"), and wherein, in the presence of the inducer, the synTF moves to the nucleus, enabling the DBD to bind to the DNA binding motif (DBM) and enabling the TA domain (ED) to be in proximity to the second promoter sequence to enable the expression of the antisense sequence of the TNA ("antisense-ON").

In one embodiment of this and all other aspects described herein, the system in the presence of an inducer, the SynTF-mediated nucleic acid sequence (SynTF-MNAS) is expressed and hybridizes with a portion of the nucleic acid sequence of the TNA, forming a double stranded nucleic acid which is degraded.

In another embodiment of this and all other aspects described herein, the double stranded nucleic acid allows RNA editing of the TNA and/or a heterologous gene having a sequence at least 98% similar to the TNA.

In another embodiment of this and all other aspects described herein, the second transcriptional module further comprises a SynTF-mediated nucleic acid sequence (SynTF-MNAS), wherein SynTF-MNAS is operatively linked to the second promoter and encodes at least one antisense nucleic acid sequence directed against at least a portion of the TNA, and wherein the SynTF-MNAS sequence is located 3' of the TNA and 5' of the second promoter.

In another embodiment of this and all other aspects described herein, the antisense nucleic acid sequence is selected from any of: a RNAi molecule, shRNA, siRNA, and miRNA.

In another embodiment of this and all other aspects described herein, the second transcriptional module further comprises a SynTF-mediated nucleic acid sequence (SynTF-MNAS), wherein the SynTF-MNAS is operatively linked to the second promoter and encodes a nucleic acid sequence that hybridizes with at least a portion of the TNA, wherein the SynTF-MNAS has a nucleic acid change as compared to the TNA.

In another embodiment of this and all other aspects described herein, the system further comprising a Ribosome entry (RZ) site located 3' of the TNA and 5' of the SynTF-MNAS.

In another embodiment of this and all other aspects described herein, the first and second promoters are constitutive promoters. In another embodiment of this and all other aspects described herein, the first and second promoters are selected from a group consisting of SV40, CMV, UBC, EF1A, PGK and CAGG. In another embodiment of this and all other aspects described herein, the first and second promoters selected are the same constitutive promoter. In another embodiment of this and all other aspects described herein, the first and second promoter selected are different constitutive promoters.

In another embodiment of this and all other aspects described herein, the DBD is selected from a group consisting of helix-turn-helix domain, zinc-finger binding domain, leucine zipper, winged helix domain, winged helix-turn-helix domain, helix-loop-helix domain, HMG-box domain, Wor3 domain, or OB-fold domain. In another embodiment of this and all other aspects described herein, wherein the DBD is a zinc-finger binding domain.

In another embodiment of this and all other aspects described herein, the TA domain is selected from a group consisting of acidic domains, glutamine-rich domains, proline-rich domains, and isoleucine-rich domains.

In another embodiment of this and all other aspects described herein, the TA domain is selected from acidic domains. In another embodiment of this and all other aspects described herein, the TA domain is VP64. In another embodiment of this and all other aspects described herein, the nuclear localization domain is ERT2. In another embodiment of this and all other aspects described herein, the inducer is 4-OHT. In another embodiment of this and all other aspects described herein, the system uses the engineered genetic construct of any of the embodiments as described herein. In another embodiment of this and all other aspects described herein, the system is performed in a cell comprising any of the embodiments as described herein.

In another aspect as described herein is a method for transiently and reversibly regulating a gene of interest, the method comprising contacting the cell of any of the embodiments as described herein with an inducer molecule. In another embodiment of this and all other aspects described herein, the inducer molecule is 4-OHT.

In some embodiments, the technology described herein can be modified to encompasses many variants, including, but not limited to alterations to the transcriptional machinery, genetic payload and induction system. For example, in some embodiments it is encompassed that modifications to the transcriptional machinery can include, for example, but not be limited to, the use of different mammalian transcriptional activation domains in place of VP64 (e.g., p65, VPR), and/or stronger or weaker constitutive promoters (e.g., hPGK, CAG, SFFV), and/or different DNA binding domain variants (e.g., Zinc Fingers, Gal4, Tetracycline Responsive Element). For the genetic payload, variants could include secreted cytokine (IL-2, IL-12, IL-18, Interferon Gamma), antibodies (anti-CD19, anti-CD47, anti-PD1), or additional genetic switches (Transcription Factors). In some embodiments it is encompassed that modifications to the induction system can include, but not be limited to, additional or different small molecule inducers (e.g., Tetracycline, Caffeine, Abscisic Acid), and/or light gated activation (e.g., Optogenetic CRY2/CIB1), and/or cellular environment factor induction (e.g., HIF1a, NFkB, ARG1), and/or GPCR activation induced (e.g., TANGO), and/or surface receptor activation (e.g., TCR activation, SynNotch) could be tailored and used to induce anti-sense mediated repression of the target nucleic acid (TNA).

BRIEF DESCRIPTION OF THE DRAWINGS

FIG. 2A shows an exemplary synTF comprising (i) a zinc finger domain as the DNA-binding domain (DBD), (ii) an effector domain that is a transcription activation domain (TA domain), and (ii) a nuclear localization domain which is ERT2, that serves as a 4-OHT nuclear translocation domain. FIG. 2B shows an exemplary engineered genetic synthetic inducible-repressor construct comprising a first promoter, a gene of interest (GOI) and in the antisense direction, a second promoter and a DNA binding motif (DBM) that binds to the DNA binding domain of the synTF.

FIG. 3A is a schematic of a cell comprising the synTF and the genetic synthetic inducible-repressor construct, and in the absence of a small-molecule inducer binding to the synTF, the gene of interest is expressed from the first promoter. FIG. 3B shows an embodiment that when the inducer binds to the synTF, the synTF moves from the cytosol to the synthetic inducible-repressor construct and binds to the DNA binding motif (DBM). FIG. 3C shows the next step of antisense expression of the GOI from the second promoter, which results in double-stranded RNAi and degradation of the expressed sense-strand of the GOI.

FIG. 4A-4C is a schematic showing the effect of an inducer on the activity of the anti-sense repressor construct, with 4-OHT as an exemplary inducer. FIG. 4A shows an exemplary synthetic inducible-repressor construct, with the first transcription module comprising a first promoter, and a GOI, and a second transcription module which is in the opposite orientation (i.e., antisense direction) to the first transcription unit, the second transcription module comprising a promoter and DBM (e.g., a ZF binding domain). FIG. 4B shows in the absence of the inducer molecule, e.g., 4-OHT, the gene of interest is transcribed, which results in expression of the protein. FIG. 4C shows that in the presence of the inducer, e.g., 4-OHT, the synTF translocates to the nucleus, and the DBD of the synTF bind to the DBM of the construct, resulting in transcription of the anti-sense construct of the GOI from the second promoter, which results in the anti-sense mediated decay of the gene of interest, with the overall effect of inhibition of the expression of GOI.

FIG. 5A shows the timescale of addition of 4-OHT for at 3 days to cells comprising a synthetic inducible repressor circuit comprising mCherry as the GOI, and removal (or withdrawal) of 4-OHT after day 3. The expression of mCherry was measured at days 0, d1, d2, d3, d4, d6, d7, d9 and d11. FIG. 5B shows the % mCherry expressed in the presence of 4-OHT at 0.1 μM, 0.2 μM and 0.5 μM for d0-d3, and for 8-days after 4-OHT removal (d4-d11), showing that in the presence of 4-OHT mCherry expression is reduced to about 20% of normal levels in the presence of 4-OHT, and mCharry expression is significantly increased after the removal of 4-OHT, with mCherry levels back to normal levels 8-days after the removal of 4-OHT at 0.1 μM.

FIG. 6A shows an embodiment of a synTF comprising a repressor domain (e.g., synTF-RD), the synTF comprising a zinc finger domain, a repressor domain (e.g., KRAB) and a nuclear localization domain (e.g., ERT2), and a corresponding repressor construct. FIG. 6B shows the % mCherry expressed in the presence of 4-OHT at 0.1 μM, 0.2 μM, 0.5 μM and 1 μM for d0-d3, and for 8-days after 4-OHT removal (d4-d 11), showing milder repression as compared to the synTF and construct used in FIG. 5B.

FIG. 8 shows the % mCherry expressed in the presence of 4-OHT for d0-d3 (at 0.1 μM, 0.2 M, 0.5 μM and 1 μM) for duplicate experiments and for four days after 4-OHT removal (d4-d7), showing greater repression of mCherry as compared to the construct in the top pane of FIG. 7.

FIG. 12A shows an engineered synthetic inducible repressor construct construct comprise in the 5'-3' direction (a) a first transcriptional module and a (b) second transcriptional module, where the first transcription module comprises a first promoter and a nucleic acid sequence that encodes a gene of interest (GOI) or transgene, which is operatively linked to the first promoter, and the second transcription unit comprises in a 5' to 3' direction, a DBM, a second promoter, an nucleic acid sequence encoding a RNA polymerase III molecule, and a SynTF-MNAS, where the synTF-MNAS is a RNAi molecule that binds to at least a portion of the GOI. In this embodiment, the first and second promoters are in the same orientation. FIG. 12B shows an engineered synthetic inducible repressor construct which comprises, in the 5'-3' direction (a) a first transcriptional module and a (b) second transcriptional module, where the first transcription module comprises a first promoter and a nucleic acid sequence that encodes a gene of interest (GOI) or transgene, which is operatively linked to the first promoter, and the second transcription unit comprises in a 5' to 3' direction, a DBM, a second promoter, an nucleic acid sequence encoding a RNA polymerase III molecule, and a SynTF-MNAS, where the synTF-MNAS is a RNA editing molecule that can bind to the mRNA expressed from the GOI nucleic acid sequence. Without wishing to be bound by theory, in this embodiment, when the SynTF-MNAS is expressed, it can form a dsRNA molecule with a portion of the mRNA expressed from the GOI, which can be recognized by a RNA gene editing molecule for RNA editing, e.g., using the CRISPR/Cas9 editing mechanism. FIG. 12C shows an alternative exemplary synTF for use in the methods, compositions and systems as disclosed herein, and in particular, for the engineered synthetic inducible repressor constructs shown in FIGS. 12A and 12B, and shows a zinc-finger domain as the DBD, a RNA Pol III activation domain, and ERT2 as a nuclear localization domain. FIG. 12D shows an alternative exemplary synTF for use in the methods, compositions and systems as disclosed herein, and in particular, for the engineered synthetic inducible repressor constructs shown in FIGS. 12A and 12B, and shows a synTF comprising, in the order of: a zinc-finger domain as the DBD, a ERT2 as a nuclear localization domain, and a RNA Pol III activation domain.

FIG. 13A shows an exemplary engineered synthetic inducible repressor constructs comprising in the 5'-3' direction (a) a first transcriptional module and a (b) second transcriptional module, where the first transcriptional module comprises a first promoter and a nucleic acid sequence that encodes a gene of interest (GOI) operatively linked to the first promoter, and where the second transcriptional module comprises in a 5' to 3' direction, a second promoter and a DNA binding motif (DBM), each of which are in the opposite orientation to that of the first promoter and the GOI in the first translation module. FIG. 13B shows an exemplary modification to the engineered synthetic inducible repressor construct shown in FIG. 13A, where the second transcription module (also referred to as unit) further comprises the nucleic acid sequence of a synTF-mediated nucleic acid sequence (synTF-MNAS) located 5', and operatively linked to second promoter, where the synTF-MNAS encodes at least one antisense nucleic acid sequence, e.g., RNAi molecule, directed against at least a portion of the GOI. In such an embodiment, when the synTF-MNAS (e.g., RNAi molecule) is expressed, it can hybridize with a portion of the nucleic acid sequence of the GOI to forms a double stranded nucleic acid molecule, which is then degraded. FIG. 13C shows another exemplary modification to the engineered synthetic inducible repressor construct shown in FIG. 13A, where the second transcription module (also referred to as unit) further comprises the nucleic acid sequence of a synTF-mediated nucleic acid sequence (synTF-MNAS) located 5', and operatively linked to second promoter, where the synTF-MNAS encodes at a double stranded RNA (dsRNA) molecule with a nucleic acid modification for RNA-mediated gene editing. In such an embodiment, when the synTF-MNAS (e.g., dsRNA) molecule) is expressed, it can hybridize with a portion of the nucleic acid sequence of the GOI to form a double stranded nucleic acid molecule with a mismatch, which can be gene-edited by RNA-mediated editing machinery.

DETAILED DESCRIPTION

Described herein is an inducible repressor system for regulating a gene of interest or target nucleic acid (TNA), comprising a synthetic transcription factor (synTF) and a engineered genetic circuit. For illustrative purposes only, referring to FIG. 13A, one aspect of the present invention relates to an engineered genetic circuit comprises in the 5' to 3' direction; (i) a first transcriptional module comprising a first promoter, a nucleotide sequence encoding a target nucleic acid (TNA) operatively linked to the first promoter; and (ii) a second transcriptional module, comprising a second promoter in the antisense direction to the first promoter, and a DNA binding motif (DBM) orientated in the antisense direction to the TNA. In some embodiment, the DBM comprises a target nucleic acid for binding of the at least one DNA binding domain (DBD) of a synthetic transcription factor (synTF), the SynTF comprising: (i) at least one DBD, (ii) at least one transcription activation (TA) domain, and (iii) at least one nuclear localization domain. In some embodiments, the nuclear localization domain sequesters the synTF in the cytosol in the absence of an inducer, and in the presence of an inducer, the nuclear localization domain moves to the cytosol.

Figure 13A:
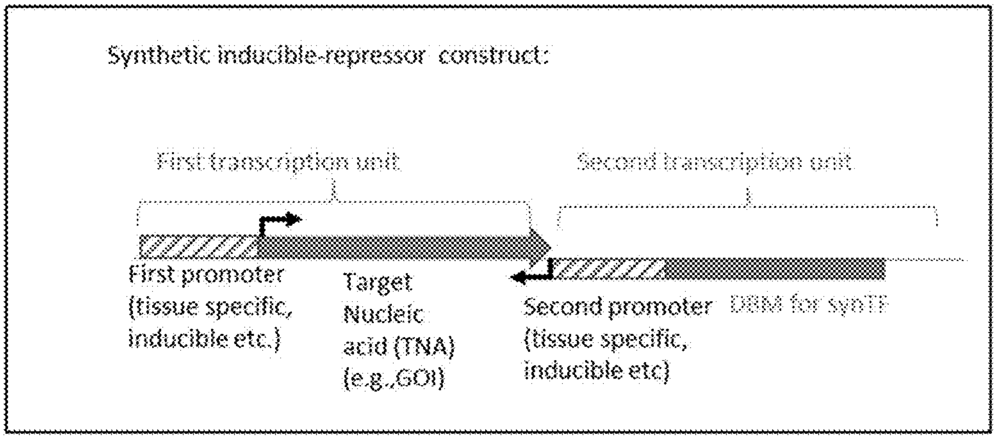
FIG. 13A-13C show schematics of exemplary engineered synthetic inducible repressor constructs for use in the methods, constructs and systems as disclosed herein, comprising (a) a first transcriptional module and a (b) second transcriptional module, where the first and second transcription module are orientated in opposite directions with respect to each other.
Figure 13B:
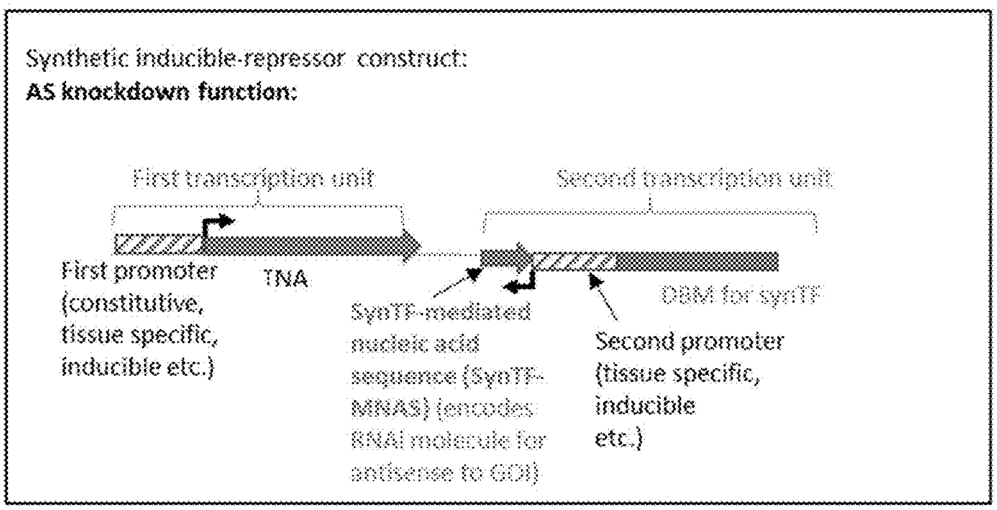

In some embodiments, the engineered genetic circuit is configured for antisense knockdown of the GOA or TNA, for example, for illustrative purposes, see FIG. 13B. In some embodiments, the engineered genetic circuit is configured for a gene editing function, e.g., see FIG. 13C for illustrative purposes.

Other aspects of the technology relate to cells comprising the engineered genetic construct (also referred interchangeably to as a "synthetic inducible-repressor construct") as disclosed herein, a composition or vector comprising the engineered inducible-repressor construct, and cells comprising the engineered construct as described herein. Other aspects relate to a system using the engineered construct as described herein, comprising a synthetic transcription factor (synTF) and an engineered inducible-repressor construct as described herein.

Other aspects of the technology relate to a method for transiently and reversibly regulating the expression of a gene of interest, comprising contacting a cell comprising the synthetic inducible-repressor construct with an inducer molecule, thereby inducing transcription of the anti-sense to the target nucleic acid (TNA), resulting in repression of the TNA expression.

I. System for Repressing a Gene of Interest Comprising a Synthetic Inducible-Repressor Construct and synTF The technology described herein relates to a small-molecule inducible transcriptional repressor system which is able to robustly and transiently silence transgene expression (e.g., a transgene of interest, or gene of interest (GOI)) in mammalian cells. In particular, the technology described herein relates to a synthetic gene circuit which functions in coordination with a synthetic transcription factor (synTF) to repress the expression of a GOI. The synthetic repressor system disclosed herein is an improvement over existing synthetic repressor systems due to its ability to be inducible,—that is, it can control the gene repression of the transgene of interest (e.g., GOI or target nucleic acid (TNA)) in a transient and reversible manner, which is mediated by the presence or absence of an inducer molecule. In particular, the technology described herein is an inducible and reversible anti-sense repressor system that can be used in a cell to control the expression of a GOI. Such a system advances the precision and tunability of genes expressed from synthetic gene circuits, where the inducible repressor circuit functions as an inducible and reversible mRNA anti-sense repressor switch or 'off switch'. Using this system, the inventors have demonstrated a robust and temporary repression of a transgene of interest (GOI) (also referred to herein as a target nucleic acid (TNA)), in the presence of the inducer, which is reversible upon withdrawal or removal of the inducer molecule.

Figure 3A:
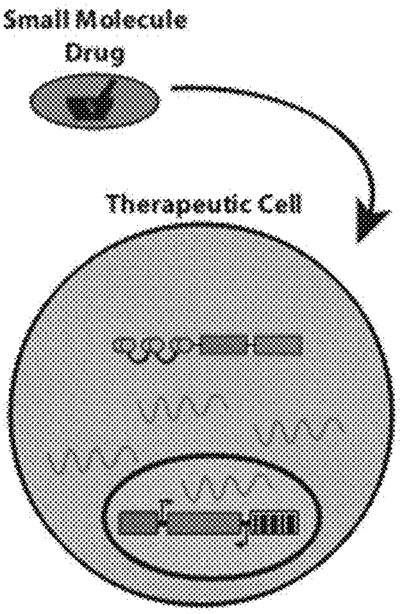
FIG. 3A-3C is a schematic of an exemplary inducible repressor synthetic construct and synTF and the sequential steps for inducer-mediated anti-sense repression of the GOI.
Figure 3B:
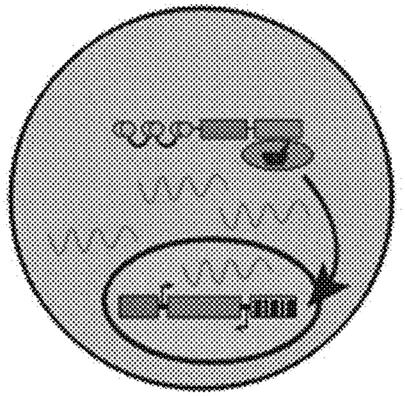
Figure 3C:
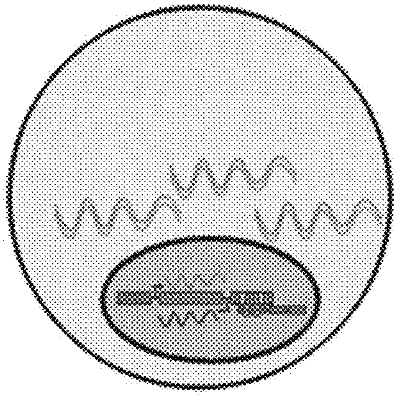

Without wishing to be bound by theory and referring to FIG. 3A-3C as an illustrative example, a cell comprising a synthetic transcription factor (SynTF) as disclosed herein) and synthetic inducible repressor circuit can work cooperatively in the presence of an inducer to regulate (e.g., inducer-mediated inhibition) of a GOI encoded by the synthetic inducible repressor circuit. More specifically, as shown in FIG. 3A, in the absence of an inducer, a cell comprising a synthetic transcription factor (synTF) and a synthetic inducible-repressor circuit expresses the GOI from the first promoter in the circuit. When the inducer is present, the synTF is activated, and translocate to the nucleus of the cell, see, e.g., FIG. 3B, where the activated synTF induces the expression of the anti-sense transcription of the GOI (i.e., induces expression of the GOI in the antisense direction). As shown in FIG. 3C, the anti-sense GOI transcript results in RNA-interference (RNAi) and d.s. RNA degradation of the GOA transcript, effectively resulting in "switching off", or repressing, the expression of the GOI.

Without wishing to be bound by theory, as a proof of principal, the inventors demonstrated the effectiveness of the small-molecule inducible transcriptional repressor system as follows: in the absence of the inducer molecule (e.g., 4-OHT), the ERT2 keeps the anti-sense repressor in the cytoplasm (FIG. 3A). However, in the presence of 4-OHT, the ERT2 domain shuttles the anti-sense repressor to the nucleus where it binds to the zinc finger binding domain (ZF BD or DBD) and induces transcription of anti-sense mRNA to the gene of interest (GOI) (FIG. 3B) The anti-sense transcript mediates mRNA silencing via mRNA degradation or mRNA decay leading to repression of the expression of the GOI (FIG. 3C).

In all aspects herein, 4-OT is a represented as an exemplary inducer molecule, and can be readily substituted with other inducer molecules that activate a synTF as disclosed herein. An "inducer molecule" or "inducer" or "inducing agent" with respect to an inducer that activates a synTF as described herein, is typically an exogenous compound or protein that is administered to a cell in such a way as to activate the function of the synTF from an non-active state. In some embodiments, the inducer is a small molecule, however, synTF inducers can include, but not be limited to RNA inducers, proteins, as well as environmental inducers. In some embodiments, a small molecule inducers can be any of: Tetracycline, Caffeine, Abscisic Acid. In some embodiments, the synTF is induced by light gated activation (e.g., the synTF is conjugated with Optogenetic CRY2/CIB). In some embodiments, the inducer a cellular environment factor induction factor, e.g., but not limited to HIF1a, NFkB, ARG1). In some embodiments, the inducer is induced by GPCR activation (e.g., TANGO), and/or by surface receptor activation (TCR activation, SynNotch). In some embodiments, the inducer is an environmental inducer, e.g., heat or temperature that activate heat-sensitive domains of the synTF, as well as environmental states of the cell. By way of an illustrative example only, an environmental inducer can be, e.g., but not limited to a cell's in a particular environmental state (e.g., if a T cell is in a pro-inflammatory state or if a T cell in an anti-inflammatory state). Accordingly, in some embodiments, an inducer is an environmental inducer which can serve as a positive-feedback loop, whereby the GOI can trigger a particular state of the cell, which induces the activation of the synTF. Examples include the expression of a GOI reaching a particular pre-defined threshold level, or the expression of the GOI achieving a pre-defined cellular response (e.g., decrease of a target protein or increase of a target protein, etc.). By way of an illustrative example only, a pre-defined cellular response can be a decrease in any of: a cancer antigen, a self-antigen, a microbial antigen, an allergen, or an environmental antigen to, or below pre-defined threshold level for that antigen. Accordingly, in some embodiments, a synTF inducer molecule is a protein or endogenous agent that is induced by the GOI reaching a predefined level, thereby triggering a positive-feedback loop.

In some embodiments, the inducible antisense repressor construct design is comprised of two units, a first transcription unit and a second transcription unit, the first transcriptional unit comprising a first promoter operatively linked to a GOI. The second transcriptional unit is downstream or 3' to the first transcriptional unit, and is in the opposite orientation to the first transcriptional unit, and comprises a DNA binding motif (DBM) for binding of a synTF as disclosed herein, and optionally, a second promoter which is operatively linked to either to (i) the nucleic acid encoding the GOI in the antisense orientation, or alternatively, (ii) synTF-mediated nucleic acid sequence (synTF-MNAS) that can encode any one of: a RNAi molecule, a target antisense portion of the GOI, or a dsRNA molecule for RNA-mediated gene editing (see, e.g., FIG. 13A-13C). In some embodiments, the synthetic inducible antisense repressor is responsive to a synTF that comprises an artificial zinc finger protein, e.g., as disclosed in U.S. Pat. Nos. 10,138,493 and 11,530,246, or Patent Application Nos. US 2020/0377564, US2020/0002710, each of which are incorporated herein in their entirety. In some embodiments, a synTF useful in the methods, systems and composition as disclosed herein comprises (i) an artificial zinc finger protein as a DNA binding domain (DBD), a transcriptional activation domain (e.g., VP64 transcriptional domain) and a nuclear localization domain (e.g., ERT2 domain) (e.g., see FIG. 2A). In some embodiments, other synTF are useful, e.g., see FIGS. 12A and 12B, where the transactional domain is RNA polymerase III activation domain.

Figure 5A:
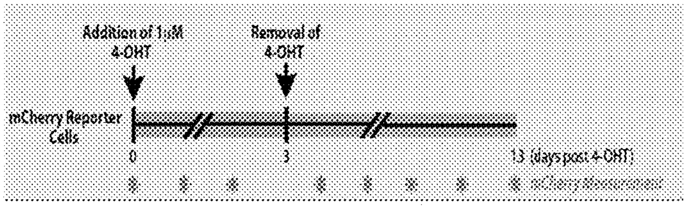
FIGS. 5A and 5B demonstrates the reversible silencing of the expression of GOI after addition and removal of the inducer 4-OHT to 293 cells comprising a synTF and construct shown in FIG. 2A-2B.
Figure 5B:
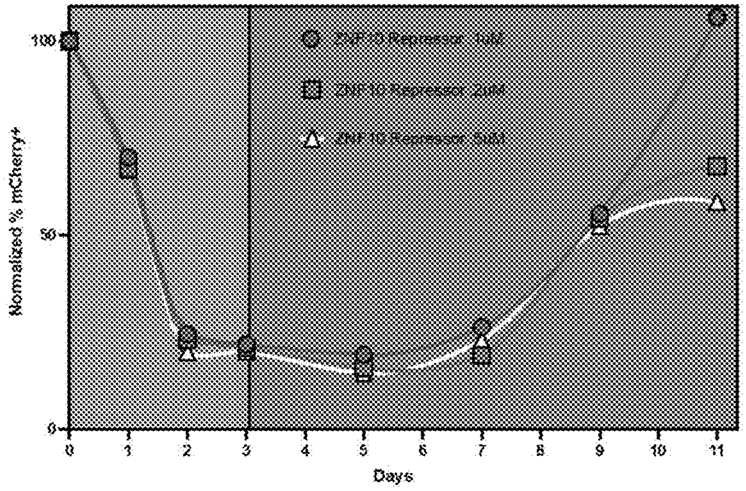
Figure 6A:
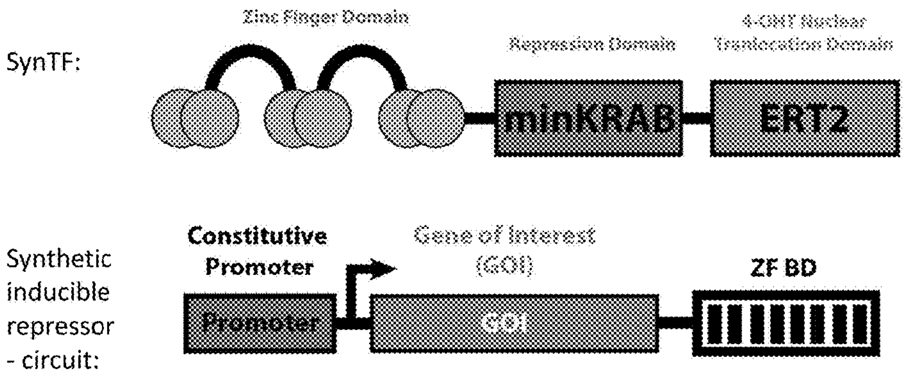
FIG. 6A-6B show an alternative embodiment of a synTF and construct system for downstream inducible-repression.
Figure 6B:
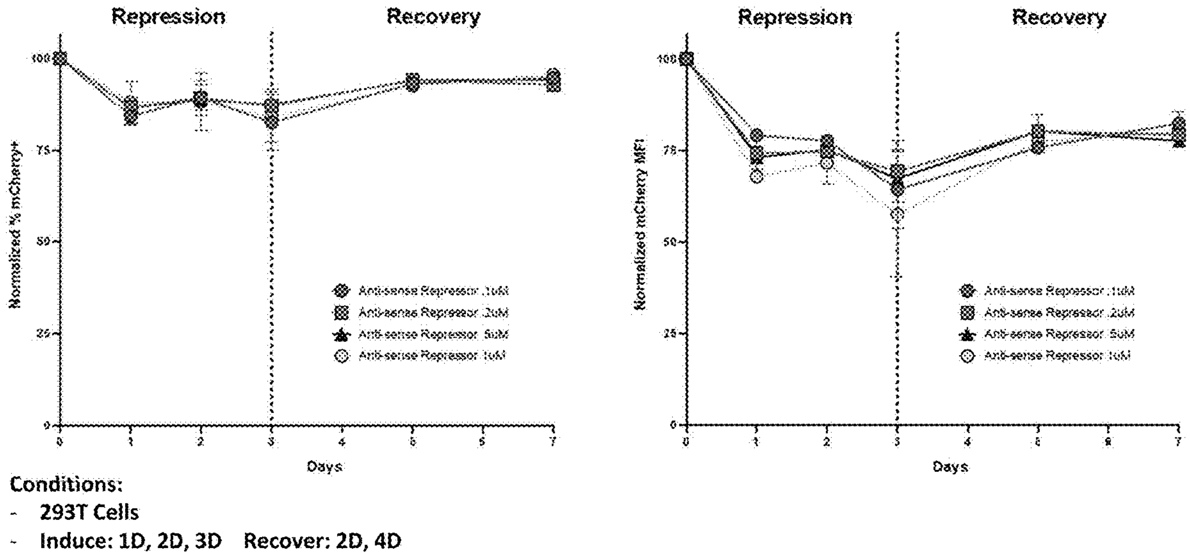

To assess transcriptional repression of the GOI, inducible antisense repressor construct comprising (i) a first transcriptional unit comprising a constitutively active promoter operatively linked to a mCherry fluorescent reporter GOI was used, and a (ii) a second transcriptional unit comprising an inverted DNA binding motif (DBM) comprising a zinc finger binding array operatively linked to a minimal promoter (FIG. 4A). To evaluate the kinetics of this repressor switch, 293T cells where generated to stably express both the inducible anti-sense repressor and fluorescent reporter. In order to determine whether the repressor switch is able to transiently silence GOIs, the inventors treated reporter cells with 0.1 uM 4-OHT and measured mCherry reporter fluorescence at 1 day, 2 days, and 3 days. In order to determine whether the repressor switch transiently represses GOIs, the inventors removed 4-OHT and measured fluorescence expression after 2 days, 4 days, 6 days, and 8 days (FIG. 5A-5B). The inventors discovered that the reporter fluorescence expression is strongly repressed after 3 days and restored 8 days post 4-OHT removal, demonstrating the anti-sense repressor circuit functioned as a robust and transient repression system.

Accordingly, in one aspect as described herein is an engineered genetic construct comprising a heterologous nucleic acid construct comprising, in the 5' to 3' direction; a first transcription module comprising: a first promoter, a nucleotide sequence encoding a target nucleic acid (TNA) operatively linked to the first promoter; and a second transcriptional module, comprising: a second promoter in the antisense direction to the first promoter, a DNA binding motif (DBM) orientated in the antisense direction to the GOI, the DBM comprising a target nucleic acid for binding of the at least one DBD of a synthetic transcription factor (synTF), the SynTF comprising: at least one DNA-binding domain (DBD), at least one Transcription activation (TA) domain, and at least one nuclear localization domain, wherein the nuclear localization domain sequesters the synTF in the cytosol in the absence of an inducer, and in the presence of an inducer, the nuclear localization domain moves to the cytosol in the presence of the inducer.

In one embodiment of this and all other aspects described herein, the second transcriptional module further comprises a SynTF-mediated nucleic acid sequence (SynTF-MNAS), wherein the SynTF-MNAS is operatively linked to the second promoter and encodes at least one antisense nucleic acid sequence directed against at least a portion of the TNA, and wherein the SynTF-MNAS is located 3' of the TNA and 5' of the second promoter. In another embodiment of this and all other aspects described herein, the antisense nucleic acid sequence is selected from any of: a RNAi molecule, shRNA, siRNA, or miRNA, or other inhibiting nucleic acid molecules.

Aspects of the technology described herein, relate to methods to control gene expression of the GOI, where the administration (i.e., presence) or removal of an inducer results in a switch between the "ON" and "OFF" states of the expression of the operatively linked nucleic acid sequence (e.g., nucleic acid encoding a GOI). Thus, as used herein, the "ON" state of the system described herein is where the first promoter operatively linked to a GOI nucleic acid sequence is actively driving transcription of the GOI nucleic acid sequence. Conversely, as disclosed herein in some embodiments, the "OFF" state is when synTF is activated by the inducer, and the synTF mediates gene expression from the second promoter and the expressed antisense molecule (e.g., RNAi molecule or synTF-MNAS) targets the GOI transcript (which was expressed from the first promoter), resulting in mRNA silencing of the GOI via mRNA degradation or mRNA decay leading to repression of the expression of the GOI (e.g., GOI degradation or decay of the expressed GOI transcript). In some embodiments, the inducer can be doxycycline, tamoxifen, rapamycin, or abscisic acid for the promoter operative linked to a nucleic acid sequence encoding a recombinase.

Synthetic Inducible-Repressor Construct

Aspects of the technology described herein relates to systems, methods and compositions for cooperative molecular complexes in cells that can be used to regulate and repress the expression of a GOI in a cell. That is, the technology described herein relates to a system for cooperative function of an synthetic transcription factor (synTF) and a synthetic inducible-repressor circuit comprising the nucleic acid encoding a GOI to control or repress the expression of the GOI.

Figure 12A:
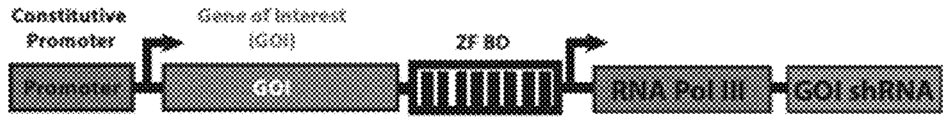
FIG. 12A-12D are exemplary embodiments of alterative configuration of the configuration of the synthetic inducible repressor construct, and the corresponding synTFs useful in the methods, compositions and systems as disclosed herein, with the first and second transcription modules in the same orientation, and depicts modifications to the inducible anti-sense repressor design technology.
Figure 12B:
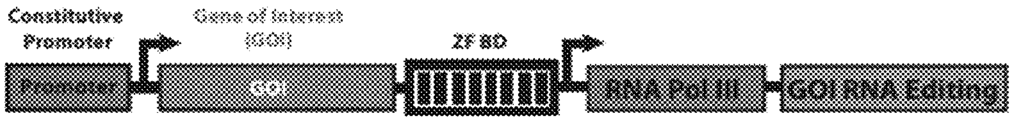
Figure 13C:
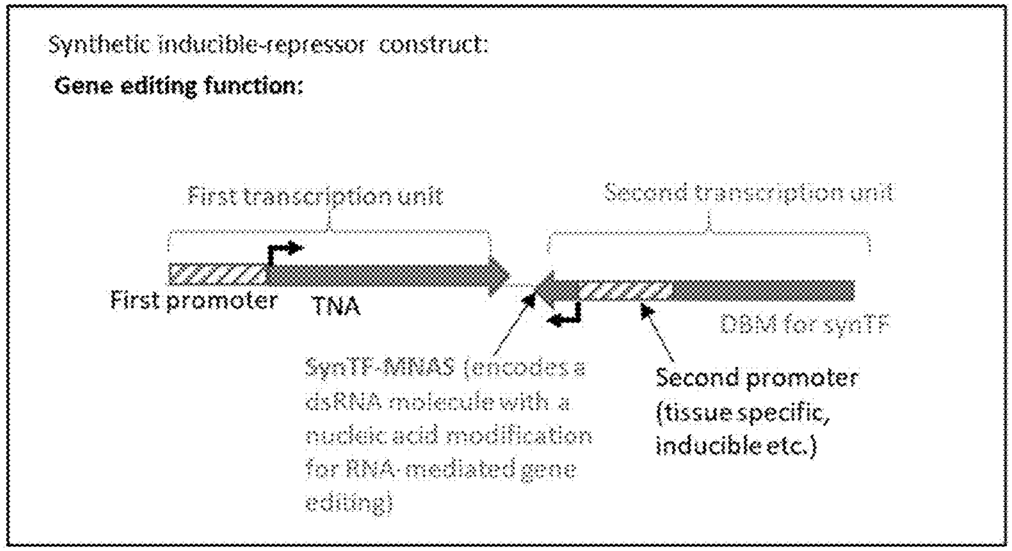

In summary, the components of system for an engineered genetic construct comprise in the 5'-3' direction (a) a first transcriptional module and a (b) second transcriptional module. An exemplary synthetic inducible-repressor construct is shown in FIGS. 13A, 13B, and 13C. Alternative exemplary synthetic inducible-repressor constructs are shown in FIGS. 12A and 12B.

(a) First transcriptional module: In some embodiments, the first transcriptional module comprises a first promoter and a nucleic acid sequence that encodes a gene of interest (GOI) operatively linked to the first promoter.

The gene of interest (GOI) can be modified to include features, for example to reduce GpG islands and/or minimize alternative open reading frames and/or maximize sequence diversity and/or to improve the nucleic acid sequence (e.g., a codon-optimized nucleic acid sequence). In some embodiments, the codon-optimized nucleic acid described herein is operatively linked to a promoter. In some embodiments, the codon-optimized nucleic acid is included in an expression vector in expressible form (e.g. a viral based expression vector).

(b) Second transcriptional module: In some embodiments, the second transcriptional module comprises in a 5' to 3' direction, a second promoter and a DNA binding motif (DBM), each of which are in the opposite orientation to that of the first promoter and the GOI in the first translation module. The second promoter is different from the first promoter in the first transcription module. The second promoter is in the antisense direction compared to the first promoter. The DBM is also oriented in the antisense direction as compared to the GOI in the first transcriptional module. In some embodiments, the second transcriptional module further comprises a SynTF mediated target nucleic acid sequence (also referred to as SynTF-MNAS). The target nucleic acid sequence is operatively linked to the second promoter and encodes at least one antisense nucleic acid sequence directed against at least a portion of the GOI, and wherein the target nucleic acid sequence is located 3' of the GOI and 5' of the second promoter. In some embodiments, in the presence of an inducer, the target nucleic acid sequence can be expressed and hybridize with a portion of the nucleic acid sequence of the GOI, which forms a double stranded nucleic acid (e.g., an antisense nucleic acid sequence) which is degraded.

In some embodiments, the second transcription module is configured to comprise, in a 5' to 3' direction, a DBM, a second promoter, an nucleic acid sequence encoding a RNA polymerase III molecule, and a SynTF-MNAS, which can be selected from (i) a RNAi molecule that binds to the GOI, or (ii) a RNA editing molecule that can bind to the mRNA expressed from the GOI nucleic acid sequence. Exemplary second transcript modules of such a configuration are shown in FIGS. 12A-12B.

In some embodiments, an antisense nucleic acid sequence can include, but not be limited to an RNAi molecule or an shRNA.

II. First Transcriptional Module Components

In all aspects of all embodiments herein, a first transcriptional module comprises a first promoter and a nucleic acid sequence that encodes a gene of interest (GOI) operatively linked to the first promoter. In some embodiments, the GOI is any transgene that is desired to be expressed in a cell, and is also referred to as target nucleic acid (TNA).

A. First Promoters

The administration or removal of an inducer as disclosed herein results in a switch between the "on" or "off" states of the transcription of the GOI operably linked to the first promoter. Thus, as defined herein the "on" state, as it refers to a first promoter operably linked to a GOI nucleic acid sequence, refers to the state when the promoter is actively driving transcription of the operably linked nucleic acid sequence, i.e., the linked nucleic acid sequence is expressed.

As discussed herein, the synthetic inducible-repressor circuit as disclosed herein comprises a first promoter and a second promoter, each of which are in the first transcription module and second transcription module/unit respectively, as disclosed herein. Promoters suitable for use as a first promoter in the synthetic inducible repressor construct are further described below. In some embodiments, the first promoter is different from the second promoter. In some embodiments, the first promoter is an inducible promoter as defined herein. In some embodiments, the first promoter is a tissue-specific promoter as defined herein. Other promoters commonly known to persons of ordinary skill are encompassed for use as a first promoter herein. In some embodiments, the first promoter is a synthetic promoter.

A promoter useful as first promoter may also contain sub-regions at which regulatory proteins and molecules may bind, such as RNA polymerase and other transcription factors. Promoters useful as first promoters may be constitutive, inducible, activatable, repressible, tissue-specific or any combination thereof. In some embodiments, the first promoter is constitutive. In some embodiments, the first promoter is an inducible promoter. In some embodiments, the first promoter is a mammalian promoter. In some embodiments, the first promoter is a tissue-specific promoter.

B. GOI or Transgene

The synthetic inducible-repressor circuit as disclosed herein can comprise any GOI, also referred to as a target nucleic acid sequence (TNA). In some embodiments, a TNA is any transcript of interest to be expressed in a cell. In some embodiments, the TNA or GOI is a transgene, where the transgene encodes a genetic medicine selected from any of a nucleic acid sequence, an inhibitor, peptide or polypeptide, antibody or antibody fragment, antigen, antagonist, agonist, RNAi molecule, aptamer, and the like. In some embodiments, the TNA is a heterologous nucleic acid sequence which encodes a therapeutic transgene (e.g., a genetic medicine) at a desired level of expression of the transgene, which, in some embodiments, is a therapeutically effective amount. In all aspects herein, a GOI or TNA comprises a transgene which is a genetic medicine, e.g., selected from any of a nucleic acid, an inhibitor, peptide or polypeptide, antibody or antibody fragment, antigen, antagonist, agonist, RNAi molecule, aptamer, and the like. In some embodiments, the desired expression level of the TNA or transgene achieved or mediated by transgene repression in the presence of the inducer molecule, inducer after the administration of the composition at one or more time points after the second time point is a therapeutically effective amount of the transgene.

The gene of interest (GOI) can be modified to include features, for example to reduce GpG islands and/or minimize alternative open reading frames and/or maximize sequence diversity and/or to improve the nucleic acid sequence (e.g., a codon-optimized nucleic acid sequence). In some embodiments, the codon-optimized nucleic acid described herein is operatively linked to a promoter. In some embodiments, the codon-optimized nucleic acid is included in an expression vector in expressible form (e.g. a viral based expression vector).

In some embodiments, a GOI operatively linked to the second promoter is a transgene, and can be, for example, any therapeutic molecule and/or prophylactic molecule. In some embodiments, the transgene or GOI is protein or peptide (e.g., a therapeutic protein or peptide). In some embodiments, the transgene or GOI is a nucleic acid (e.g., a therapeutic nucleic acid). Examples of nucleic acids include RNA, DNA or a combination of RNA and DNA. In some embodiments the product interest is DNA (e.g., single-stranded DNA or double-stranded DNA). In some embodiments, the product of interest is RNA. For example, the product of interest may be selected form RNA interference (RNAi) molecules, such as short-hairpin RNAs, short interfering RNAs and micro RNAs. In some embodiments, a transgene or GOI controls viral replication and/or virulence.

Examples of therapeutic and/or prophylactic molecules, such as antibodies (e.g., monoclonal or polyclonal; chimeric; humanized; including antibody fragments and antibody derivatives (bispecific, trispecific, scFv, and Fab)), enzymes, hormones, inflammatory molecules, anti-inflammatory molecules, immunomodulatory molecules, and anti-cancer molecules. Specific examples of the foregoing classes of therapeutic molecules are known in the art, any of which may be used in accordance with the present disclosure.

In some embodiments, the transgene or GOI is an immunomodulatory molecule. An immunomodulatory molecule is a molecule (e.g., protein or nucleic acid) that regulates an immune response. In some embodiments, the immunomodulatory molecules are expressed at the surface of, or secreted from, a cancerous cell or secreted from a cancerous cell.

In some embodiments, the immunomodulatory molecule is a synthetic T cell engager (STE). A synthetic T cell engager is a molecule (e.g., protein) that binds to (e.g., through a ligand-receptor binding interaction) a molecule on the surface of a T cell (e.g., a cytotoxic T cell), or otherwise elicits a cytotoxic T cell response. In some embodiments, an STE is a receptor that binds to a ligand on the surface of a T cell. In some embodiments, an STE is an anti-CD3 antibody or antibody fragment. A STE of the present disclosure is typically expressed at the surface of, or secreted from, a cancer cell or other disease cell to which a nucleic acid encoding the STEs is delivered. See, e.g., International Publication Number WO 2016/205737, incorporated herein by reference.

Examples of STEs of the present disclosure include antibodies, antibody fragments and receptors that binds to T cell surface antigens. T cell surface antigens include, for example, CD3, CD4, CD8 and CD45.

In some embodiments, a GOI can be selected from chemokines, cytokines and checkpoint inhibitors. Immunomodulatory molecule include immunostimulatory molecule and immunoinhibitory molecule. An immunostimulatory molecule is a molecule that stimulates an immune response (including enhancing a pre-existing immune response) in a subject, whether alone or in combination with another molecule. Examples include antigens, adjuvants (e.g., TLR ligands, nucleic acids comprising an unmethylated CpG dinucleotide, single-stranded or double-stranded RNA, flagellin, muramyl dipeptide), cytokines including interleukins (e.g., IL-2, IL-7, IL-15 (or superagonist/mutant forms of these cytokines), IL-12, IFN-gamma, IFN-alpha, GM-CSF, FLT3-ligand, etc.), immunostimulatory antibodies (e.g., anti-CTLA-4, anti-CD28, anti-CD3, or single chain/antibody fragments of these molecules), and the like. In some embodiments, a GOI useful in the methods, compositions as disclosed herein, include nucleic acid sequences encoding a secreted cytokine (e.g., not limited to IL-2, IL-12, IL-18, Interferon Gamma), or one or more antibodies (e.g., but not limited to, anti-CD19, anti-CD47, anti-PD1). In some embodiments, a TNA useful in the methods, compositions as disclosed herein, includes nucleic acid sequences encoding one or more additional genetic switches, including transcription Factors, and/or a synthetic transcription factor known in the art.

An immunoinhibitory molecule is a molecule that inhibits an immune response in a subject, whether alone or in combination with another molecule. Examples include anti-CD3 antibody or antibody fragment, and other immunosuppressants.

Antigens may be, without limitation, a cancer antigen, a self-antigen, a microbial antigen, an allergen, or an environmental antigen.

A cancer antigen is an antigen that is expressed preferentially by cancer cells (e.g., it is expressed at higher levels in cancer cells than on non-cancer cells) and in some instances it is expressed solely by cancer cells. The cancer antigen may be expressed within a cancer cell or on the surface of the cancer cell. The cancer antigen may be MART-1/Melan-A, gp100, adenosine deaminase-binding protein (ADAbp), FAP, cyclophilin b, colorectal associated antigen (CRC)-C017-1A/GA733, carcinoembryonic antigen (CEA), CAP-1, CAP-2, etv6, AML1, prostate specific antigen (PSA), PSA-1, PSA-2, PSA-3, prostate-specific membrane antigen (PSMA), T cell receptor/CD3-zeta chain, and CD20. The cancer antigen may be selected from the group consisting of MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5). The cancer antigen may be selected from the group consisting of GAGE-1, GAGE-2, GAGE-3, GAGE-4, GAGE-5, GAGE-6, GAGE-7, GAGE-8, GAGE-9. The cancer antigen may be selected from the group consisting of BAGE, RAGE, LAGE-1, NAG, GnT-V, MUM-1, CDK4, tyrosinase, p53, MUC family, HER2/neu, p2lras, RCAS 1, α-fetoprotein, E-cadherin, α-catenin, β-catenin, γ-catenin, p120ctn, gp100Pmel117, PRAME, NY-ESO-1, cdc27, adenomatous polyposis coli protein (APC), fodrin, Connexin 37, Ig-idiotype, p15, gp75, GM2 ganglioside, GD2 ganglioside, human papilloma virus proteins, Smad family of tumor antigens, Imp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, CD20, and c-erbB-2.

In some embodiments, a transgene or GOI is a diagnostic molecule. In some embodiments, a diagnostic molecule may be, for example, a detectable molecule, e.g., detectable by microscopy. In some embodiments, a diagnostic molecule is a fluorescent molecule, such as a fluorescent protein. Fluorescent proteins are known in the art, any of which may be used in accordance with the present disclosure. In some embodiments, the diagnostic molecule is a reporter molecule that can be imaged in a subject (e.g., human subject). For example, the reporter molecule may be a sodium iodide symporter (see, e.g., Galanis, E. et al. Cancer Research, 75(1): 22-30, 2015, incorporated herein by reference).

In some embodiments, the first transcription unit of the synthetic genetic circuit as disclosed herein can further comprise one or more promoters, e.g. artificial promoters that is/are operably linked to and drive expression of one or more nucleic acid molecules encoding a GOI, e.g., where the GOI can be therapeutic or marker polypeptides. For example, the first transcription unit can comprise (i) a first promoter (promoter 1A) operatively linked to a first GOI (e.g., GOI-A) which can be a therapeutic molecule, and also comprise one or more subsequent first promoters (e.g., promoter 1B, 1C, 1D etc), each linked to additional GOI, e.g., where the additional GOI (e.g., GOI-B, GOI-C, GOI-D etc.) can be a second therapeutic molecule as disclosed herein, or a marker molecule for example. In such a system, one or more synTF can be used to repress the expression of the first GOI and/or the second GOI, where the synTF can be activated by the same or a different inducer molecule. In such a system, one or more GOI (e.g., GOI-A, GOI-B etc.) can be repressed by the same inducible synTF or by different synTF. In some embodiments, each GOI are operatively linked to the same first promoter. In some embodiments, each GOI (e.g., GOI-A, GOI-B, GOI-C, GOI-D etc) are operatively linked to different first promoters respectively (e.g., first promoter 1B, 1C, 1D, respectively).

In some embodiments, the GOI or TNA can be modified to comprise, or include a synthetic nucleic acid sequence that functions as a target binding site (herein referred to as a "AS-binding site") for the antisense nucleic acid sequence or synTF-MNAS expressed from the second transcription unit. In some embodiments, such a GOI or TNA can comprise, for example, at least 3, 4, 5, 6, 7, 8, 9 or 10 AS-binding sites. In some embodiments, a GOI or TNA can comprise at least five (or five) AS-binding sites. In some embodiments, a GOI or TNA includes 1-10 AS-binding sites. For example, a GOI or TNA can comprise between 1-9, 1-8, 1-7, 1-6, 1-5, 1-4, 1-3, 1-2, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-9, 8-10, 8-9, or 9-10 AS-binding sites, where the AS-binding sites can be the same or comprise different nucleic acid sequences that can be bound by the same or different AS molecules or synTF-MNAS expressed from the second transcription unit. In some embodiments, a GOI or TNA includes 2-10 AS-binding sites. In some embodiments, a GOI or TNA includes 5-10 AS-binding sites.

The length of an AS-binding site (e.g., AS-GOI or synTF-MNAS binding site) in the GOI or TNA mRNA may vary. In some embodiments, the length of a AS-GOI or synTF-MNAS binding site (i.e., AS-binding site) is between about 10-30, or about 15-30 nucleotides. For example, the length of an AS-binding site (i.e., AS-GOI or synTF-MNAS binding site) in a GOI mRNA can be 15, 16, 17, 18, 19, 20, 21, 22, 23, 24, 25, 26, 27, 28, 29, or 30 nucleotides. In some embodiments, the length of an AS-binding site is 15-20, 20-30, or 20-25 nucleotides.

In such embodiments, the synthetic AS-binding site can be located at any of: the 3' or at the 5' or located within the nucleic acid sequence of the GOI or TNA, providing the AS-binding site does not interfere with the function of the expressed GOI or TNA. In some embodiments, the AS-binding sites are located in tandem. That is, the AS-binding sites may be directly adjacent to each other (contiguous with each other), or separated from each other by nucleotide spacers (e.g., spacers having lengths of 1-10, e.g., 1, 2, 3, 4, 5, 6, 7, 8, 9 or 10) nucleotides.

III. Second Transcriptional Module Components

In some embodiments, the second transcriptional module comprises (i) a second promoter and (ii) a DNA binding motif (DBM). In some embodiments, the second promoter is different from the first promoter in the first transcription module. On the sense strand of DNA, the second promoter is in the antisense direction as compared to the first promoter, such that on the antisense DNA strand, the second promoter is functional and, in some embodiments, is operatively linked to the antisense of the GOI. On the sense DNA strand, the DBM is oriented in the antisense direction as compared to the GOI in the first transcriptional module. In some embodiments, the second transcriptional module further comprises a synTF mediated nucleic acid sequence, which is referred to as a synTF-MNAS—meaning a nucleic acid sequence which is expressed when the synTF binds to the DBM. In some embodiments, the synTF-MNAS is operatively linked to the second promoter and encodes at least one antisense nucleic acid sequence or RNAi molecule directed against at least a portion of the GOI, and wherein the target nucleic acid sequence is located 3' of the GOI and 5' of the second promoter. In some embodiments, in the presence of an inducer, the target nucleic acid sequence can be expressed and hybridize with a portion of the nucleic acid sequence of the GOI, which forms a double stranded nucleic acid (e.g., an antisense nucleic acid sequence) which is degraded.

In some embodiments, an antisense nucleic acid sequence or synTF-MNAS can include, but not be limited to an RNAi molecule, e.g., microRNA (miRNA), scRNA or an shRNA, or simply the antisense strand of a portion of the GOI.

A. DNA binding Motif (DBM)

In all aspects as disclosed herein, the DBM comprises a target nucleic acid sequence which is the binding site for at least one DNA binding domain (DBD) of a synthetic transcription factor (synTF). In some embodiments, the SynTF comprises of at least one DBD, at least one transcription activation domain (TA) and at least one nuclear localization domain. In some embodiments, the nuclear localization domain sequesters the synTF in the cytosol in the absence of an inducer, and wherein in the presence of an inducer, the nuclear localization domain moves to the cytosol in the presence of the inducer.

In some embodiments, the DBM comprises a target nucleic acid for binding of the at least one DNA binding domain (DBD) of a synthetic transcription factor (synTF) as disclosed herein. The SynTF comprises of at least one DBD, at least one transcription activation domain (TA) and at least one nuclear localization domain. In some embodiments, the nuclear localization domain sequesters the synTF in the cytosol in the absence of an inducer, and wherein in the presence of an inducer, the nuclear localization domain moves to the cytosol in the presence of the inducer.

In some embodiments, a DNA binding motif (DBM) is the binding site for the DNA-binding domain (DBD) of the synTF. In some embodiments, a synthetic gene circuit comprises at least two DNA binding motifs (DBM) downstream (e.g., 3') to a second promoter or other regulatory element, where the second promoter or regulatory element is operatively linked to either the antisense of the gene of interest (GOI), or alternatively, a synTF-MNAS, as disclosed herein. The nucleotide sequence of one or more of nucleotides of one or more DBMs can be modified to change (e.g., increase or decrease) the binding affinity for binding of the DBD of the synTF. In some embodiments, the second transcription module of the synthetic gene circuit can be represented as comprising: promoter-$[DBM]_n$ or [SynTF-MNAS]-promoter-$[DBM]_n$.

In some embodiments of any of the aspects, a synthetic inducible-repressor construct described herein can comprise at least two DBM, each of which can be the binding site for at least one synTF. In some embodiments, a synthetic inducible-repressor construct described herein can comprise at least two DBM, each of which can be the binding site for different or unique synTF, where each synTF respond or is activated by a different inducer molecule. Thus, repression of the GOI can be mediated by more than one inducer molecule, each of which activates a different synTF that binds to a DBM in the second transcription module. Accordingly, in some embodiments of any of the aspects, a synthetic inducible-repressor system disclosed herein can comprise any combination of at least two synTF polypeptides as described herein, controlling the same GOIs.

The DBMs of the synthetic gene circuit are DNA sequence elements are specially designed to be a "target" DNA binding site, or "target" DNA sequence or "target DNA sequence" elements in the context of the DNA binding domain (DBD) of the synthetic transcription factor, and are used interchangeably. Moreover, these DNA sequence elements are specially designed to be recognized and bound specially by engineered synthetic transcription factors. When used together in vivo, these DNA sequence elements (e.g., DBM) and their specially engineered synthetic transcription factors form the basic components of a regulatable, programmable gene expression system that allows the modulation of gene expression in vivo.

In one embodiment, this DBM nucleic acid sequence is part of an engineered responsive promoter or transcriptional unit, where the sequence is located upstream of the promoter sequence. Upstream as is conventionally used in the art means 5' of an element, conversely, downstream is used conventionally in the art to mean 3' of an element. In the case of the synthetic inducible-repressor construct described herein, the first transcription module comprises a first promoter that is 5' (upstream) of a GOI, and the second transcription module comprise as a second promoter that is 3' of the GOI (or synTF-MNAS) and 5' of the DBM.

In one embodiment, this DBM nucleic acid sequence is operably linked to the promoter sequence to influence the transcription initiation when the DBM nucleic acid sequence is occupied by the DBD of the synTF having an effector domain (e.g., TA domain, TR domain or EE domain, as disclosed herein).

In some embodiments, the synthetic inducible-repressor construct as disclosed herein can comprises repeat DBM sequences, for example, [DBM]n wherein n is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more.

The nucleotide sequence of the DBM for a synthetic inducible-repressor construct as disclosed herein is dependent on the DNA binding domain (DBD) of the synTF, and in some embodiments, the cognate DNA binding sequence of the zinc finger domain of the DBD. In some embodiments, the DBM is at least 8-15 nucleotides in length. In some embodiments, the DBD is 8, 9, 10, 11, 12, 13, 14, 15, 16, 17, 18, 19, 20, 21 nucleotides in length. In some embodiments, the DBM comprises synthetic nucleotides.

Exemplary DBMs can for 43-8 (ZF1) be selected from: aGAGTGAGGAC (SEQ ID NO: 1), aCAGTGAGGAC (SEQ ID NO: 2) (DBM2); aTAGTGAGGAC (SEQ ID NO: 3) (DBM3); Exemplary DBMs can for 42-10 (ZF2) be selected from: aGACGCTGCTc (SEQ ID NO: 4); tGACGCTGCTc (SEQ ID NO: 5); aGACGGTGCTc (SEQ ID NO: 6); aCACGCTGCTc (SEQ ID NO: 7); aGACGCTACTc (SEQ ID NO: 8); aGACGCTGCTa (SEQ ID NO: 9); aGACTCTGCTc (SEQ ID NO: 10).

In some embodiments of any aspect described herein, in the nucleotide sequence of the DBM of the synthetic circuit is an orthogonal target DNA sequences comprising any of SEQ ID NOS: 81-91 disclosed in U.S. Pat. No. 10,138,493, which is incorporated herein in its entirety by reference.

In some embodiments, a DBM in a second transcription module useful in the methods, systems and compositions as disclosed herein, comprises a nucleic acid sequence of any of SEQ ID NO: 181-191 or 229-240 as disclosed in U.S. Pat. No. 11,530,246. In some embodiments of any of the aspects, the DBD binds to DNA binding motifs (DBM) comprising any of: SEQ ID NOs: 229-240 as disclosed in U.S. Pat. No. 11,530,246.

SEQ ID NO: 11 is an exemplary DBM (DNA binding motif) nucleic acid sequence for 36-4: c GAA GAC GCT g. SEQ ID NO: 11-SEQ ID NO: 14 are exemplary DBM affinity variant nucleic acid sequences for 43-8. Bold text indicates residues mutated from the WT sequence. SEQ ID NO: 12 is 43-8 DBM1-aGAGTGAGGAc. SEQ ID NO: 13 is 43-8 DBM2-aCAGTGAGGAc. SEQ ID NO: 14 is 43-8 DBM3-aTAGTGAGGAc. SEQ ID NOS 15-22 are exemplary DBM affinity variant nucleic acid sequences for 42-10. Bold text indicates residues mutated from the WT sequence. SEQ ID NO: 15 is 42-10 DBM1-aGACGCTGCTc. SEQ ID NO: 16 is 42-10 DBM2-tGACGCTGCTt. SEQ ID NO: 17 is 42-10 DBM3-aGACGGTGCTc. SEQ ID NO: 18 is 42-10 DBM4-aCACGCTGCTc. SEQ ID NO: 19 is 42-10 DBM5-aGACGCTACTc. SEQ ID NO: 20 is 42-10 DBM6-aGACGCTGCTa. SEQ ID NO: 21 is 42-10 DBM7-aGACTCTGCTc. SEQ ID NO: 22 is an exemplary DBM (DNA binding motif) nucleic acid sequence for 97-4: a TTA TGG GAG a.

In some embodiments, the synthetic gene circuit comprises multiple DBM's that are the same, i.e., bind the same DBD on the synTF. In alternative embodiments, the DBM's in a synthetic inducible-repressor construct as disclosed herein are not the same (e.g., the DBM's bind to different DBDs, or alternatively, have different binding affinities for the same DBD on the synTF). For exemplary purposes, where a synthetic inducible-repressor construct comprises multiple DBMs, the second transcription module of the synthetic gene circuit can comprise [SynTF-MNAS]-[$2^{nd}$ promoter]-(DBM1)n; [SynTF-MNAS]-[$2^{nd}$ promoter]-(DBD1-DBM2-DBM3-DBM4), [SynTF-MNAS]-[$2^{nd}$ promoter]-(DBM [DBM2]n; [SynTF-MNAS]-[$2^{nd}$ promoter]-[DBM1]n-[DBM2]n-[DBM3]n; [SynTF-MNAS]-[$2^{nd}$ promoter]-[DBM1]n-[DBM2]n-[DBM3]n-[DBM4]n;

where DBM1, DBM2, DBM3, DBM4 bind to different DBDs, or alternatively, have different binding affinities for the same DBD on the synTF.

In some embodiments, a synthetic inducible-repressor construct as disclosed herein comprises a second promoter operatively linked to the antisense of the GOI or a synTF-MNAS, as described herein.

B. Second Promoters

In some embodiments, a promoter that is used as a second promoter in the synthetic inducible repressor construct as disclosed herein can be the same or different to the first promoter. A promoter drives expression or drives transcription of the nucleic acid sequence that it regulates. Without wishing to be bound by theory, in some embodiments, the second promoter can be described serves as an "inverted promoter,"—in that the promoter is a nucleic acid sequence is in the reverse orientation, such that what was the coding strand is now the non-coding strand, and vice versa. Inverted promoter sequences can be used in various embodiments of the invention to regulate the expression of the SynTF-MNAS. Thus, in some embodiments, the second promoter is an inverted promoter. In some embodiments, e.g., see FIG. 12A-12B, the second promoter is in the same orientation as the first promoter.

In some embodiments, the synthetic inducible-repressor construct as disclosed herein can comprise a first promoter (located in the first transcription module) and a second promoter (located in the second transcription module), that is, in a synthetic inducible-repressor construct described herein promoters can be found on either the sense strand, the antisense strand, or both. In some embodiments, promoters are found on both the sense and antisense strand. The promoters can be the same promoter on a nucleic acid construct. The promoters can be different promoters on a nucleic acid construct. In some embodiments, the first promoter is different to the second promoter—that is the first and second promoters are not the same. In some embodiments, the first promoter is a constitutive promoter, or an inducible promoter, or a tissue specific promoter. In some embodiments, the second promoter is selected from: a constitutive promoter, an inducible promoter, or a tissue specific promoter, but is a different promoter to the promoter sequence used for the first promoter.

In some embodiments of all aspects of the technology, a first or second promoter may or may not be used in conjunction with an "enhancer," which refers to a cis-acting regulatory sequence involved in the transcriptional activation of a nucleic acid sequence downstream of the promoter. The enhancer may be located at any functional location before or after the promoter and/or the encoded nucleic acid.

Without wishing to be limited to theory, a promoter useful herein is a nucleic acid sequence in a DNA molecule which forms the site at which transcription of a nucleic acid sequence starts (e.g., herein, is the start of the transcription of the GOI nucleic acid sequence or AS-GOI or synTF-MNAS as disclosed herein). Promoters can be about 100-1000 base pairs long, the sequence of which is highly dependent on the gene and product of transcription, type or class of RNA polymerase recruited to the site, and species of organism. There are three main portions that make up a promoter which include the core promoter, the proximal promoter, and the distal promoter. The core promoter is located most proximal to the start codon and contains the RNA polymerase binding site, TATA box, and transcription start site (TSS). The TATA box is a DNA sequence (5'-TATAAA-3') within the core promoter region where general transcription factor proteins and histones can bind. The most 3' portion (closest to the gene's start codon) of the core promoter is the TSS which is where transcription actually begins. Only eukaryotes and archaea, however, contain this TATA box. Most prokaryotes contain a sequence thought to be functionally equivalent called the Pribnow box which usually consists of the six nucleotides, TATAAT. The proximal promoter which contains many primary regulatory elements. The proximal promoter is found approximately 250 base pairs upstream from the TSS and it is the site where general transcription factors bind. The distal promoter which is upstream of the proximal promoter. The distal promoter also contains transcription factor binding sites, but mostly contains regulatory elements.

Promoters can either be inducible or constitutively active. An inducible promoter is a regulated promoter which becomes on or active in the cell in response to specific stimuli. Inducible promoters consist of cis-regulatory elements that work in concert with multiple trans-activing factors to determine overall expression output. Examples of inducible promoters include, chemically inducible promoters, temperature inducible promoters, and light inducible promoters. One who is skilled in the art will be able to select and use an inducible promoter in the construct. A constitutively active promoter is an unregulated promoter which is active in vivo at all the circumstances. These promoters carry out the transcription of associated genes continuously in the cell. The activities of these promoters are not affected by transcriptional factors. Examples of constitutively active promoters include but are not limited to cytomegalovirus (CMV) promoters, thymidine kinase (TK), simian virus 40 (SV40), elongation factor 1 alpha (EF1a), CAG, phosphoglycerate kinase gene promoter (PGK), Human U6 nuclear promoter for small RNA expression (U6), T7 promoter from the T7 bacteriophage, and Sp6 promoter from the Sp6 bacteriophage.

In some embodiments of any of the aspects, the promoter which is operatively linked to the GOI or is selected from any of: miniCMV promoter, miniTK promoter, ybTATA promoter, minSV40 promoter, CMV53 promoter, pJB42CAT5 promoter, MLP promoter, TATA promoter, pSFFV promoter, CMV promoter, pUb/UbC promoter, EF1apromoter, PGK/pGK promoter, CAG/CAGG promoter, SV40 promoter, and beta actin/ACTB promoter.

In some embodiments of any of the aspects, the second promoter which is operatively linked to a nucleic acid encoding a synTF-mediated nucleic acid sequence (synTF-MNAS) and/or is located downstream of the DNA-binding motif (DBM) is selected from any of: miniCMV promoter, miniTK promoter, ybTATA promoter, minSV40 promoter, CMV53 promoter, pJB42CAT5 promoter, MLP promoter, TATA promoter, pSFFV promoter, CMV promoter, pUb/UbC promoter, EF1apromoter, PGK/pGK promoter, CAG/CAGG promoter, SV40 promoter, and beta actin/ACTB promoter.

A promoter is classified as strong or weak according to its affinity for RNA polymerase (and/or sigma factor); this is related to how closely the promoter sequence resembles the ideal consensus sequence for the polymerase. The strength of a promoter may depend on whether initiation of transcription occurs at that promoter with high or low frequency. Different promoters with different strengths may be used to construct logic gates with different digitally settable levels of gene output expression (e.g., the level of gene expression initiated from a weak promoter is lower than the level of gene expression initiated from a strong promoter).

A promoter may be one naturally associated with a gene or sequence, as may be obtained by isolating the 5' non-coding sequences located upstream of the coding segment and/or exon of a given gene or sequence. Such a promoter can be referred to as "endogenous." Similarly, an enhancer may be one naturally associated with a nucleic acid sequence, located either downstream or upstream of that sequence.

In some embodiments, a coding nucleic acid segment may be positioned under the control of a recombinant or heterologous promoter, which refers to a promoter that is not normally associated with the encoded nucleic acid sequence in its natural environment. A recombinant or heterologous enhancer refers to an enhancer not normally associated with a nucleic acid sequence in its natural environment. Such promoters or enhancers may include promoters or enhancers of other genes; promoters or enhancers isolated from any other prokaryotic, viral or eukaryotic cell; and synthetic promoters or enhancers that are not "naturally occurring" such as, for example, those that contain different elements of different transcriptional regulatory regions and/or mutations that alter expression through methods of genetic engineering that are known in the art. In addition to producing nucleic acid sequences of promoters and enhancers synthetically, sequences may be produced using recombinant cloning and/or nucleic acid amplification technology, including PCR, in connection with the logic gates disclosed herein (see U.S. Pat. Nos. 4,683,202 and 5,928,906). Furthermore, control sequences that direct transcription and/or expression of sequences within non-nuclear organelles such as mitochondria, chloroplasts and the like, may be used in accordance with the invention.

In some embodiments, the promoter in the cassette or switch is a constitutive or tissue-specific promoter. Tissue-specific promoters are active in a specific type of cells or tissues such as B cells, monocytic cells, leukocytes, macrophages, muscle, pancreatic acinar cells, endothelial cells, astrocytes, and lung. Tissue-specific promoters are available as native or composite promoter. Native promoters, also called minimal promoters, consist of a single fragment from the 5' region of a given gene. Each of them comprises a core promoter and its natural 5'UTR. In some cases, the 5'UTR contains an intron. Composite promoters combine promoter elements of different origins or were generated by assembling a distal enhancer with a minimal promoter of the same origin. Tissue-specific promoters are commercially available through vendors such as InvivoGen.

Non-limiting constitutive promoters include EF1alpha, SFFV, CMV, RSV, SV40, PGK, CAGGS, pTK, Ube, Ubi, hU6, and H1.

In some embodiments, the promoter in the cassette is an inducible promoter.

Inducible Promoters

Inducible promoters for use in accordance with the invention may function in both prokaryotic and eukaryotic host organisms. In some embodiments, mammalian inducible promoters are used. Examples of mammalian inducible promoters for use herein include, without limitation, promoter type $P_{ACT}$:$P_{AIR}$, $P_{ART}$, $P_{BIT}$, $P_{CR5}$, $P_{CTA}$, $P_{ETR}$, $P_{NIC}$, $P_{PIP, PROP}$, $P_{SPA}$/$P_{SCA}$, $P_{TET}$, $P_{TtgR}$, promoter type $P_{Rep}$:$P_{CuO}$, $P_{ETR}$, ON8, $P_{NIC}$, $P_{PIR}$ ON, $P_{SCA}$ ON8, $P_{TetO}$, $P_{UREXS}$, promoter type $P_{Hyb}$:teto$_7$-ETR$_8$-$P_{hcMVmin}$, tet0$_7$-PIR$_3$-ETR$_8$-$P_{hcMvmin}$, and scbR$_8$-PIR$_3$-$P_{hCMVmin}$. In some embodiments, inducible promoters from other organisms, as well as synthetic promoters designed to function in a prokaryotic or eukaryotic host may be used. Examples of non-mammalian inducible promoters for use herein include, without limitation, Lentivirus promoters (e.g., Efa, CMV, Human Synapsin1 (hSyn1), CaMKIIa, hGFAP and TPH-2) and Adeno-Associated Virus promoters (e.g., CaMKIIa (AAV5), hSyn1 (AAV2), hThy1 (AAV5), fSST (AAV1), hGFAP (AAV5, AAV8), MBP (AAV8), SST (AAV2)). One important functional characteristic of the inducible promoters of the present invention is their inducibility by exposure to an externally applied inducer. Other examples of inducible promoters include tetracycline inducible (pTRE), streptogramin inducible (pPIR), macrolide inducible (pETR), allolactose or isopropyl β-D-thiogalactopyranoside inducible (pLacO), ponasterone A inducible, coumermycin/novobiocin-regulated gene expression system, hypoxia inducible (hypoxia response elements), TGFbeta inducible (SMAD response elements), amino acid deprivation inducible (ATF3/ATF3/ATF2). More examples of inducible promoters can be found at http://sabiosciences.com/reporterassays.php.

The administration or removal of an inducer results in a switch between the "ON" or "OFF" states of the transcription of the operatively linked nucleic acid sequence (e.g., nucleic acid encoding a recombinase). Thus, as used herein, the "ON" state of a promoter operatively linked to a nucleic acid sequence refers to the state when the promoter is actively driving transcription of the nucleic acid sequence (i.e., the linked nucleic acid sequence is expressed). Conversely, the "OFF" state of a promoter operatively linked, or conditionally operatively linked, to a nucleic acid sequence refers to the state when the promoter is not actively driving transcription of the nucleic acid sequence (i.e., the linked nucleic acid sequence is not expressed). In some embodiments, the inducer can be doxycycline, tamoxifen, rapamycin, or abscisic acid for the promoter operative linked to a nucleic acid sequence encoding a recombinase.

An inducible promoter for use in accordance with the invention may be induced by (or repressed by) one or more physiological condition(s), such as changes in pH, temperature, radiation, osmotic pressure, saline gradients, cell surface binding, and the concentration of one or more extrinsic or intrinsic inducing agent(s). The extrinsic inducer or inducing agent may comprise, without limitation, amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones or combinations thereof. The condition(s) and/or agent(s) that induce or repress an inducible promoter can be input(s) of the logic gates described herein.

Promoters that are inducible by ionizing radiation can be used in certain embodiments, where gene expression is induced locally in a cell by exposure to ionizing radiation such as UV or x-rays. Radiation inducible promoters include the non-limiting examples of fos promoter, c-jun promoter or at least one CarG domain of an Egr-1 promoter. Further non-limiting examples of inducible promoters include promoters from genes such as cytochrome P450 genes, inducible heat shock protein genes, metallothionein genes, hormone-inducible genes, such as the estrogen gene promoter, and such. In further embodiments, an inducible promoter useful in the methods and systems as described herein can be Zn2+ metallothionein promoter, metallothionein-1 promoter, human metallothionein IIA promoter, lac promoter, lacO promoter, mouse mammary tumor virus early promoter, mouse mammary tumor virus LTR promoter, triose dehydrogenase promoter, herpes simplex virus thymidine kinase promoter, simian virus 40 early promoter or retroviral myeloproliferative sarcoma virus promoter. Examples of inducible promoters also include mammalian probasin promoter, lactalbumin promoter, GRP78 promoter, or the bacterial tetracycline-inducible promoter. Other examples include phorbol ester, adenovirus E1A element, interferon, and serum inducible promoters.

In some embodiments, the inducer or inducing agent, i.e., a chemical, a compound or a protein, can itself be the result of transcription or expression of a nucleic acid sequence (i.e., an inducer can be a transcriptional repressor protein, such as Lad), which itself can be under the control of an inducible promoter. In some embodiments, an inducible promoter is induced in the absence of certain agents, such as a repressor. In other words, in such embodiments, the inducible promoter drives transcription of an operably linked sequence except when the repressor is present. Examples of inducible promoters include but are not limited to, tetracycline, metallothionine, ecdysone, mammalian viruses (e.g., the adenovirus late promoter; and the mouse mammary tumor virus long terminal repeat (MMTV-LTR)) and other steroid-responsive promoters, rapamycin responsive promoters and the like.

The promoters for use in the molecular/biological circuits described herein encompass the inducibility of a prokaryotic or eukaryotic promoter by, in part, either of two mechanisms. In some embodiments, the molecular/biological circuits comprise suitable inducible promoters that can be dependent upon transcriptional activators that, in turn, are reliant upon an environmental inducer. In other embodiments, the inducible promoters can be repressed by a transcriptional repressor which itself is rendered inactive by an environmental inducer, such as the product of a sequence driven by another promoter. Thus, unless specified otherwise, an inducible promoter can be either one that is induced by an inducing agent that positively activates a transcriptional activator, or one which is repressed by an inducing agent that negatively regulates a transcriptional repressor. In such embodiments of the various aspects described herein, where it is required to distinguish between an activating and a repressing inducing agent, explicit distinction will be made.

Inducible promoters that are useful in the molecular/biological circuits and methods of use described herein also include those controlled by the action of latent transcriptional activators that are subject to induction by the action of environmental inducing agents. Some non-limiting examples include the copper-inducible promoters of the yeast genes CUP1, CRS5, and SOD1 that are subject to copper-dependent activation by the yeast ACE1 transcriptional activator (see e.g. Strain and Culotta, 1996; Hottiger et al., 1994; Lapinskas et al., 1993; and Gralla et al., 1991). Alternatively, the copper inducible promoter of the yeast gene CTT1 (encoding cytosolic catalase T), which operates independently of the ACE1 transcriptional activator (Lapinskas et al., 1993), can be utilized. The copper concentrations required for effective induction of these genes are suitably low so as to be tolerated by most cell systems, including yeast and *Drosophila* cells. Alternatively, other naturally occurring inducible promoters can be used in the present invention including: steroid inducible gene promoters (see e.g. Oligino et al. (1998) Gene Ther. 5: 491-6); galactose inducible promoters from yeast (see e.g. Johnston (1987) Microbiol Rev 51: 458-76; Ruzzi et al. (1987) Mol Cell Biol 7: 991-7); and various heat shock gene promoters. Many eukaryotic transcriptional activators have been shown to function in a broad range of eukaryotic host cells, and so, for example, many of the inducible promoters identified in yeast can be adapted for use in a mammalian host cell as well. For example, a unique synthetic transcriptional induction system for mammalian cells has been developed based upon a GAL4-estrogen receptor fusion protein that induces mammalian promoters containing GAL4 binding sites (Braselmann et al. (1993) Proc Natl Acad Sci USA 90: 1657-61). These and other inducible promoters responsive to transcriptional activators that are dependent upon specific inducers are suitable for use with the cassettes, switches, and methods of use described herein.

Inducible promoters useful in some embodiments of the cassettes, switches, and methods of use disclosed herein also include those that are repressed by "transcriptional repressors" that are subject to inactivation by the action of environmental, external agents, or the product of another gene. Such inducible promoters can also be termed "repressible promoters" where it is required to distinguish between other types of promoters in a given module or component of a cassette or switch described herein. Examples include prokaryotic repressors that can transcriptionally repress eukaryotic promoters that have been engineered to incorporate appropriate repressor-binding operator sequences.

In some embodiments, repressors for use in the cassettes or switches described herein are sensitive to inactivation by a physiologically benign agent. Thus, where a lac repressor protein is used to control the expression of a promoter sequence that has been engineered to contain a lacO operator sequence, treatment of the host cell with IPTG will cause the dissociation of the lac repressor from the engineered promoter containing a lacO operator sequence and allow transcription to occur. Similarly, where a tet repressor is used to control the expression of a promoter sequence that has been engineered to contain a tetO operator sequence, treatment of the host cell with tetracycline or doxycycline will cause the dissociation of the tet repressor from the engineered promoter and allow transcription of the sequence downstream of the engineered promoter to occur.

Inducible promoters for use in accordance with the invention include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some embodiments, the inducer used in accordance with the invention is an N-acyl homoserine lactone (AHL), which is a class of signaling molecules involved in bacterial quorum sensing. Quorum sensing is a method of communication between bacteria that enables the coordination of group-based behavior based on population density. AHL can diffuse across cell membranes and is stable in growth media over a range of pH values. AHL can bind to transcriptional activators such as LuxR and stimulate transcription from cognate promoters. In some embodiments, the inducer used in accordance with the invention is anhydrotetracycline (aTc), which is a derivative of tetracycline that exhibits no antibiotic activity and is designed for use with tetracycline-controlled gene expression systems, for example, in bacteria. Other inducible promoter systems may be used in accordance with the invention.

Inducible promoters useful in the functional modules, cassettes, and switches as described herein for in vivo uses can include those responsive to biologically compatible agents, such as those that are usually encountered in defined animal tissues or cells. An example is the human PAI-1 promoter, which is inducible by tumor necrosis factor. Further suitable examples include cytochrome P450 gene promoters, inducible by various toxins and other agents; heat shock protein genes, inducible by various stresses; hormone-inducible genes, such as the estrogen gene promoter, and such.

Several small molecule ligands have been shown to mediate regulated gene expressions, either in tissue culture cells and/or in transgenic animal models. These include the FK1012 and rapamycin immunosuppressive drugs (Spencer et al., 1993; Magari et al., 1997), the progesterone antagonist mifepristone (RU486) (Wang, 1994; Wang et al., 1997), the tetracycline antibiotic derivatives (Gossen and Bujard, 1992; Gossen et al., 1995; Kistner et al., 1996), and the insect steroid hormone ecdysone (No et al., 1996). All of these references are herein incorporated by reference. By way of further example, Yao discloses in U.S. Pat. No. 6,444,871, which is incorporated herein by reference, prokaryotic elements associated with the tetracycline resistance (tet) operon, a system in which the tet repressor protein is fused with polypeptides known to modulate transcription in mammalian cells. The fusion protein is then directed to specific sites by the positioning of the tet operator sequence. For example, the tet repressor has been fused to a transactivator (VP16) and targeted to a tet operator sequence positioned upstream from the promoter of a selected gene (Gussen et al., 1992; Kim et al., 1995; Hennighausen et al., 1995). The tet repressor portion of the fusion protein binds to the operator thereby targeting the VP16 activator to the specific site where the induction of transcription is desired. An alternative approach has been to fuse the tet repressor to the KRAB repressor domain and target this protein to an operator placed several hundred base pairs upstream of a gene. Using this system, it has been found that the chimeric protein, but not the tet repressor alone, is capable of producing a 10 to 15-fold suppression of CMV-regulated gene expression (Deuschle et al., 1995).

One example of a repressible promoter useful in the cassettes and switches described herein is the Lac repressor (lacR)/operator/inducer system of *E. coli* that has been used to regulate gene expression by three different approaches: (1) prevention of transcription initiation by properly placed lac operators at promoter sites (Hu and Davidson, 1987; Brown et al., 1987; Figge et al., 1988; Fuerst et al., 1989; Deuschle et al., 1989; (2) blockage of transcribing RNA polymerase II during elongation by a LacR/operator complex (Deuschle et al. (1990); and (3) activation of a promoter responsive to a fusion between LacR and the activation domain of herpes simples virus (HSV) virion protein 16 (VP16) (Labow et al., 1990; Baim et al., 1991). In one version of the Lac system, expression of lac operator-linked sequences is constitutively activated by a LacR-VP16 fusion protein and is turned off in the presence of isopropyl-R-D-1-thiogalactopyranoside (IPTG) (Labow et al. (1990), cited supra). In another version of the system, a lacR-VP16 variant is used that binds to lac operators in the presence of IPTG, which can be enhanced by increasing the temperature of the cells (Baim et al. (1991), cited supra).

Thus, in some embodiments described herein, components of the Lac system are utilized. For example, a lac operator (LacO) can be operably linked to a tissue specific promoter, and control the transcription and expression of the heterologous target gene and another protein, such as a repressor protein for another inducible promoter. Accordingly, the expression of the heterologous target gene is inversely regulated as compared to the expression or presence of Lac repressor in the system.

Components of the tetracycline (Tc) resistance system of *E. coli* have also been found to function in eukaryotic cells and have been used to regulate gene expression. For example, the Tet repressor (TetR), which binds to tet operator (tetO) sequences in the absence of tetracycline or doxycycline and represses gene transcription, has been expressed in plant cells at sufficiently high concentrations to repress transcription from a promoter containing tet operator sequences (Gatz, C. et al. (1992) Plant J. 2:397-404). In some embodiments described herein, the Tet repressor system is similarly utilized in the molecular/biological circuits described herein.

A temperature- or heat-inducible gene regulatory system can also be used in the cassettes and switches described herein, such as the exemplary TIGR system comprising a cold-inducible transactivator in the form of a fusion protein having a heat shock responsive regulator, rheA, fused to the VP16 transactivator (Weber et al. 2003a). The promoter responsive to this fusion thermosensor comprises a rheO element operably linked to a minimal promoter, such as the minimal version of the human cytomegalovirus immediate early promoter. At the permissive temperature of 37 °C, the cold-inducible transactivator transactivates the exemplary rheO-CMVmin promoter, permitting expression of the target gene. At 41 °C, the cold-inducible transactivator no longer transactivates the rheO promoter. Any such heat-inducible or heat-regulated promoter can be used in accordance with the circuits and methods described herein, including but not limited to a heat-responsive element in a heat shock gene (e.g., hsp20-30, hsp27, hsp40, hsp60, hsp70, and hsp90). See Easton et al. (2000) Cell Stress Chaperones 5(4):276-290; Csermely et al. (1998) Pharmacol Ther 79(2): 129-168; Ohtsuka & Hata (2000) Int J Hyperthermia 16(3):231-245; and references cited therein. Sequence similarity to heat shock proteins and heat-responsive promoter elements have also been recognized in genes initially characterized with respect to other functions, and the DNA sequences that confer heat inducibility are suitable for use in the disclosed gene therapy vectors. For example, expression of glucose-responsive genes (e.g., grp94, grp78, mortalin/grp75) (Merrick et al. (1997) Cancer Lett 119(2): 185-190; Kiang et al. (1998) FASEB J 12(14):1571-16-579), calreticulin (Szewczenko-Pawlikowski et al. (1997) Mol Cell Biochem 177(1-2): 145-152); clusterin (Viard et al. (1999) J Invest Dermatol 112(3):290-296; Michel et al. (1997) Biochem J 328(Pt1): 45-50; Clark & Griswold (1997) J Androl 18(3):257-263), histocompatibility class I gene (HLA-G) (Ibrahim et al. (2000) Cell Stress Chaperones 5(3):207-218), and the Kunitz protease isoform of amyloid precursor protein (Shepherd et al. (2000) Neuroscience 99(2):317-325) are upregulated in response to heat. In the case of clusterin, a 14 base pair element that is sufficient for heat-inducibility has been delineated (Michel et al. (1997) Biochem J 328(Pt1):45-50). Similarly, a two-sequence unit comprising a 10- and a 14-base pair element in the calreticulin promoter region has been shown to confer heat-inducibility (Szewczenko-Pawlikowski et al. (1997) Mol Cell Biochem 177(1-2): 145-152).

Other inducible promoters useful in the cassettes and switches described herein include the erythromycin-resistance regulon from *E. coli*, having repressible (Eoff) and inducible (Eon) systems responsive to macrolide antibiotics, such as erythromycin, clarithromycin, and roxithromycin (Weber et al., 2002). The Eoff system utilizes an erythromycin-dependent transactivator, wherein providing a macrolide antibiotic represses transgene expression. In the Eon system, the binding of the repressor to the operator results in repression of transgene expression. Thus, in the presence of macrolides, gene expression is induced.

Fussenegger et al. (2000) describe repressible and inducible systems using a Pip (pristinamycin-induced protein) repressor encoded by the streptogramin resistance operon of *Streptomyces coelicolor*, wherein the systems are responsive to streptogramin-type antibiotics (such as, for example, pristinamycin, virginiamycin, and Synercid). The Pip DNA-binding domain is fused to a VP16 transactivation domain or to the KRAB silencing domain, for example. The presence or absence of, for example, pristinamycin, regulates the PipON and PipOFF systems in their respective manners, as described therein.

Another example of a promoter expression system useful for the cassettes and switches described herein utilizes a quorum-sensing (referring to particular prokaryotic molecule communication systems having diffusible signal molecules that prevent binding of a repressor to an operator site, resulting in repression of a target regulon) system. For example, Weber et al. (2003b) employ a fusion protein comprising the *Streptomyces coelicolor* quorum-sending receptor to a transactivating domain that regulates a chimeric promoter having a respective operator that the fusion protein binds. The expression is fine-tuned with non-toxic butyrolactones, such as SCB1 and MP133.

In some embodiments, multiregulated, multigene gene expression systems that are functionally compatible with one another are utilized in the modules, cassettes, and switches described herein (see, for example, Kramer et al. (2003)). For example, in Weber et al. (2002), the macrolide-responsive erythromycin resistance regulon system is used in conjunction with a streptogramin (PIP)-regulated and tetracycline-regulated expression systems.

Other promoters responsive to non-heat stimuli can also be used. For example, the mortalin promoter is induced by low doses of ionizing radiation (Sadekova (1997) Int J Radiat Biol 72(6):653-660), the hsp27 promoter is activated by 17-O-estradiol and estrogen receptor agonists (Porter et al. (2001) J Mol Endocrinol 26(1):31-42), the HLA-G promoter is induced by arsenite, hsp promoters can be activated by photodynamic therapy (Luna et al. (2000) Cancer Res 60(6): 1637-1644). A suitable promoter can incorporate factors such as tissue-specific activation. For example, hsp70 is transcriptionally impaired in stressed neuroblastoma cells (Drujan & De Maio (1999) 12(6):443-448) and the mortalin promoter is up-regulated in human brain tumors (Takano et al. (1997) Exp Cell Res 237(1):38-45). A promoter employed in methods described herein can show selective up-regulation in tumor cells as described, for example, for mortalin (Takano et al. (1997) Exp Cell Res 237(1):38-45), hsp27 and calreticulin (Szewczenko-Pawlikowski et al. (1997) MoI Cell Biochem 177(1-2): 145-152; Yu et al. (2000) Electrophoresis 2 1(14):3058-3068)), grp94 and grp78 (Gazit et al. (1999) Breast Cancer Res Treat 54(2): 135-146), and hsp27, hsp70, hsp73, and hsp90 (Cardillo et al. (2000) Anticancer Res 20(6B):4579-4583; Strik et al. (2000) Anticancer Res 20(6B):4457-4552).

C. Syn-TF Mediated Nucleic Acid Sequence (SynTF-MNAS)

As disclosed herein, the second promoter is operatively linked to a nucleic acid sequence that is the antisense of a portion or the whole mRNA nucleic sequence of the GOI (e.g., referred to herein as "antisense-GOI: or "AS-GOI") or one or more synTF-MNAS. In some embodiments, an antisense nucleic acid sequence of the GOI or synTF-MNAS as disclosed herein can include, but not be limited to an RNAi molecule, e.g., microRNA (miRNA), scRNA or an shRNA, or simply the antisense strand of a portion of the GOI. In some embodiments, one or more antisense nucleic acid sequence of the GOI or one or more synTF-MNAS can function in RNA silencing and post-transcriptional regulation of the GOI expression, e.g., where the antisense nucleic acid sequence of the GOI or synTF-MNAS comprise a nucleic acid sequence wholly or partially complementary to sequences found in GOI nucleic acid sequence. When the antisense nucleic acid sequence of the GOI or synTF-MNAS binds to the complementary or partially complementary nucleic acid sequences in GOI mRNA, it leads to mRNA silencing via mRNA degradation thus preventing mRNA translation. The antisense nucleic acid sequence of the GOI or synTF-MNAS suppresses GOI expression in the presence of the inducer that activates the synTF.

In some embodiments, the antisense nucleic acid sequence of the GOI or one or more synTF-MNAS can recognize at least 1, or at least 2, or at least 3 or more binding sites (e.g., partially or wholly complementary nucleic acid sequences) in the GOI or TNA.

In all aspects of the second transcription unit, the anti-sense nucleic acid sequences of the GOI (e.g., referred to herein as "antisense-GOI: or "AS-GOI") or synTF-MNAS expressed from the second transcription unit bind to a portion of the mRNA of the GOI expressed from the first promoter. In some embodiments, the AS-GOI or synTF-MNAS has a nucleic acid sequence that has an identical complementary sequence to a portion of the GOI mRNA (i.e., they have a nucleotide sequence that results in 100% hybridization over a portion of at least 10- or at least 12-nucleotides). In some embodiments, the AS-GOI or synTF-MNAS has a nucleic acid sequence that share at least 80% (e.g., at least 85%, 90%, 95%, 96%, 97%, 98%, or 99%) nucleotide complementary to a portion of at least 10-nucleotides of the GOI mRNA, or an AS-binding site (e.g., synthetic AS-binding site as disclosed herein) present in the GOI mRNA.

In some embodiments, the length of a nucleic acid sequence of a AS-GOI or synTF-MNAS can vary. In some embodiments, the length of a AS-GOI or synTF-MNAS is between about 10-30, or about 15-30 nucleotides. For example, the length of a AS-GOI or synTF-MNAS is sufficient to bind to an AS-binding site in a GOI mRNA, and in some embodiments, a AS-GOI or synTF-MNAS expressed by the second transcription unit can be 15, 16, 17, 18, 19, 20, 21, 22, 23, 24, 25, 26, 27, 28, 29, or 30 nucleotides in length. In some embodiments, the length of a AS-GOI or synTF-MNAS is 15-20, 20-30, or 20-25 nucleotides. In some embodiments, where the second promoter induces the transcription of the antisense sequence of the GOI (see, e.g., FIG. 2B) the length of a AS-GOI is the length of the nucleic acid sequence of the GOI, or at least 80% thereof or less than 80% (e.g., at least 80%, 75%, 70%, 65%, 60%, 55%, or 50%, or 45%, or 40%, or 35%, 30%, or 25%, or 20%, or 15%, or 10%, or 5%, or 4%, or 3%, or 2%, or 1%) of the length of the GOI mRNA sequence.

In some embodiments, the nucleic acid sequence of a AS-GOI or synTF-MNAS, when expressed by the second transcription unit, is wholly (100%) complementary to between about 10-30, or about 15-30 nucleotides of the GOI mRNA. In other embodiments, the nucleic acid sequence of a AS-GOI or synTF-MNAS expressed by the second transcription unit is partially (less than 100%) complementary to between about 10-30, or about 15-30 nucleotides of the GOI mRNA, e.g., at least 99%, or at least 98%, or at least 97% or at least 96%, or at least 95% or at least 85% (e.g., at least 85%, 86%, 87%, 88%, 89%, 90%, 95%, 96%, 97%, 98%, or 99%) to at least about 10-30, or about 15-30 nucleotides of the GOI mRNA.

As used herein, the antisense nucleic acid sequence can comprise of a RNAi molecule, a shRNA, a siRNA, a miRNA. A microRNA (miRNA) is a small non-coding RNA molecule (e.g., containing about 22 nucleotides) that typically functions in RNA silencing and post-transcriptional regulation of gene expression. miRNA molecules include a sequence wholly or partially complementary to sequences found in the 3' untranslated region (UTR) of some mRNA transcripts. Binding of a miRNA to a miRNA binding site leads to silencing that may occur via mRNA degradation or prevention of translation.

In some embodiments of any of the aspects, second transcriptional module further comprises a SynTF-mediated nucleic acid sequence (SynTF-MNAS), wherein the SynTF-MNAS is operatively linked to the second promoter and encodes a nucleic acid sequence that encodes a double stranded RNA (dsRNA) molecule that hybridizes with at least a portion of the target nucleic acid sequence, wherein the dsRNA molecule comprises at least one nucleic acid change as compared to the nucleic acid sequence of the TNA. Such an embodiment is useful to mediate gene-editing of one or more nucleotides in the nucleic acid sequence of the GOI expressed from the first promoter.

In some embodiments, the synTF-MNAS is operatively linked to the second promoter and comprises a nucleic acid sequence that encodes at least one antisense nucleic acid sequence directed against at least a portion of the TNA, such that the synTF-MNAS and the TNA forms a dsRNA molecule that is subsequently degraded.

In some embodiments, the second transcription unit of the synthetic inducer repressor construct as disclosed herein can comprise multiple antisense nucleic acid sequences of the GOI or synTF-MNAS, which can be encoded in tandem and operatively linked to at least one second promoter. Such an embodiment can allow for the same synTF to induce the expression of different AS-GOI or synTF-MNAS that can have different AS-binding sites in the GOI. In alternative embodiments, the expression of each AS-GOI or synTF-MNAS can be activated by different synTFs, thus enabling a system where different inducer molecules can activate different synTFs and thus different inducers can function to repress the expression of the GOI. Such an embodiment is useful, for example, where a first inducer can activate a first synTF that functions to repress the GOI to a certain level, and a second inducer can activate a second synTF to repress the GOI to a different level. Such an embodiment allows fine tailoring of the expression of the GOI and thus serves as a tunable, modular approach to antisense repression of the GOI.

D. Spacers

Figure 7:
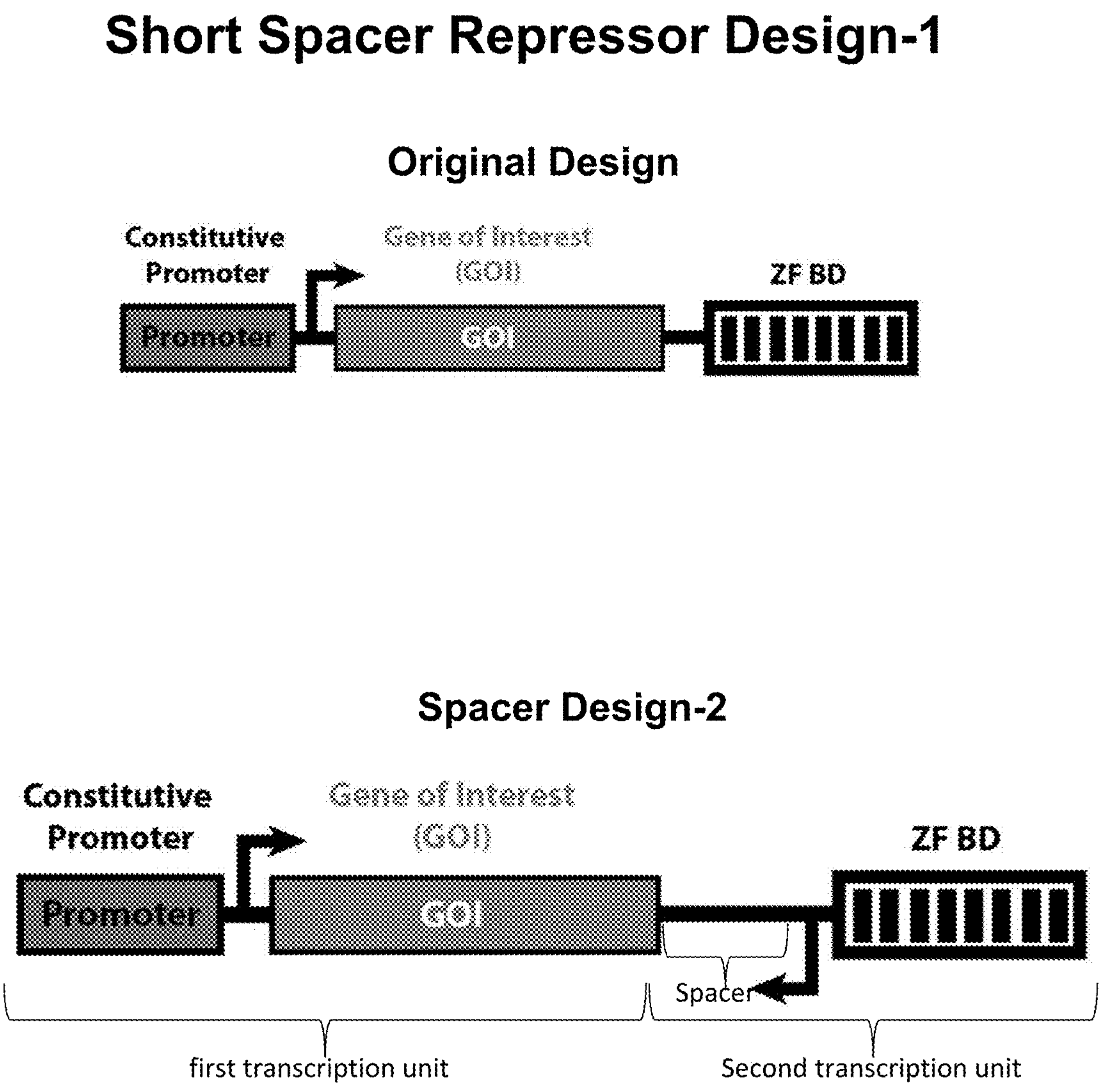
FIG. 7 is a schematic of an exemplary inducible-repressor circuit (top panel), and a second exemplary inducible-repressor circuit (bottom panel), where the second inducible-repressor circuit is modified to comprise, in the second transcription unit, a spacer and a second promoter, and the DBD, each if which are in the antisense direction to the first transcription unit comprising the first promoter and GOI.
Figure 8:
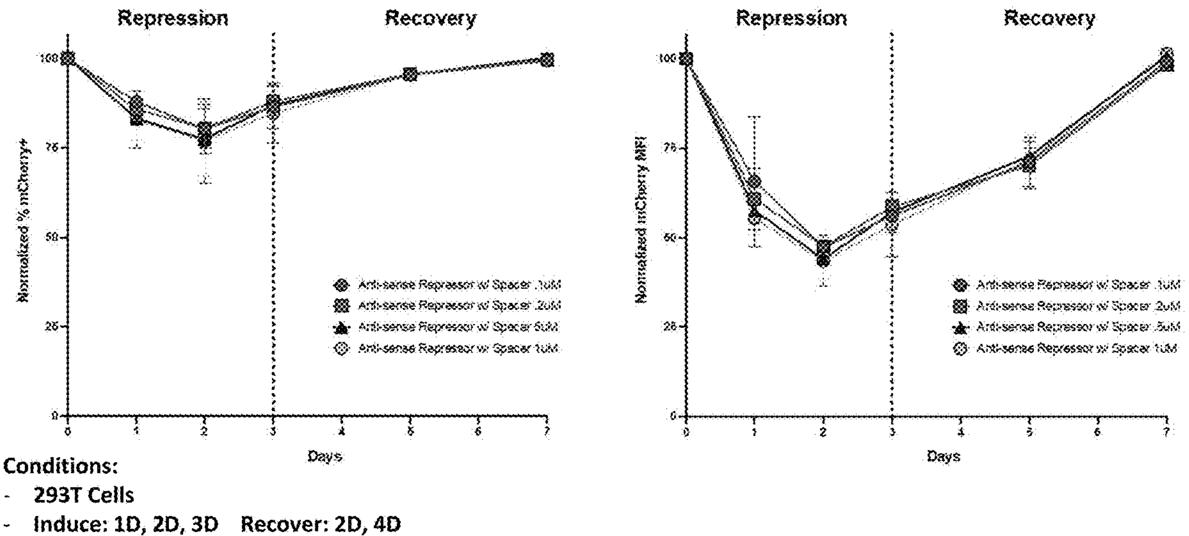
FIG. 8 shows repression of mCherry GOI with an exemplary inducible-repressor circuit comprising a spacer and a second promoter as illustrated in the bottom panel FIG. 7.
Figure 9:
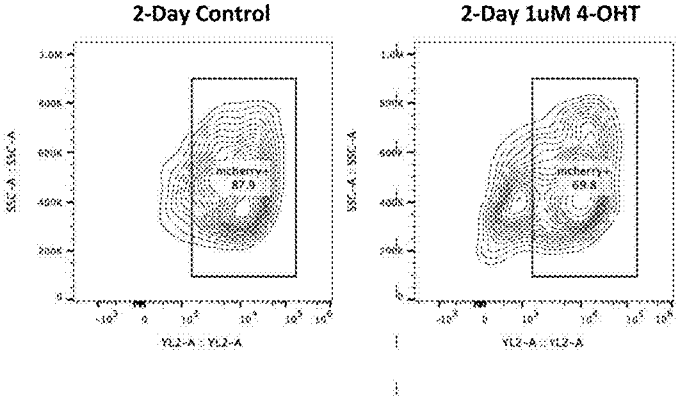
FIG. 9 shows results of the FACS flow plot of cells from FIG. 8, showing 2-days after addition of 1 uM 4-OHT, mCherry expression is decreased from 87.9% to 69.8%.
Figure 10:
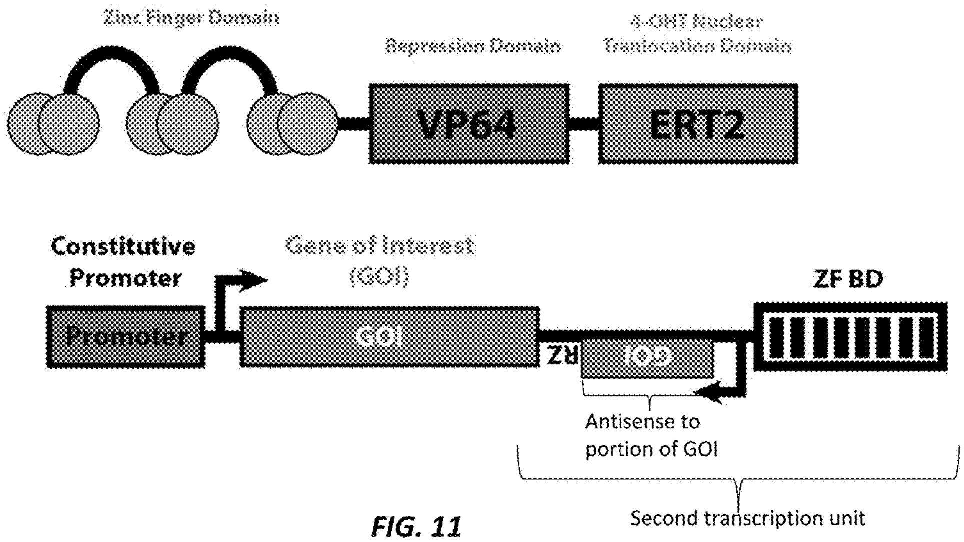
FIG. 10 is a schematic of an exemplary synTF comprising VP64, and an exemplary inducible anti-sense repressor construct comprising, in the second transcription unit, a ribosome entry site (RZ), and a nucleic acid sequence that is the antisense to a portion of the nucleic acid encoding the GOI, which are both 5' to the second promoter and the DBD. In some embodiments, the antisense to the portion of the GOI, herein referred to as "synTF-mediated nucleic acid sequence" or "synTF-MNAS" can be replaced by any RNAi molecule known to persons of ordinary skill in the art.
Figure 11:
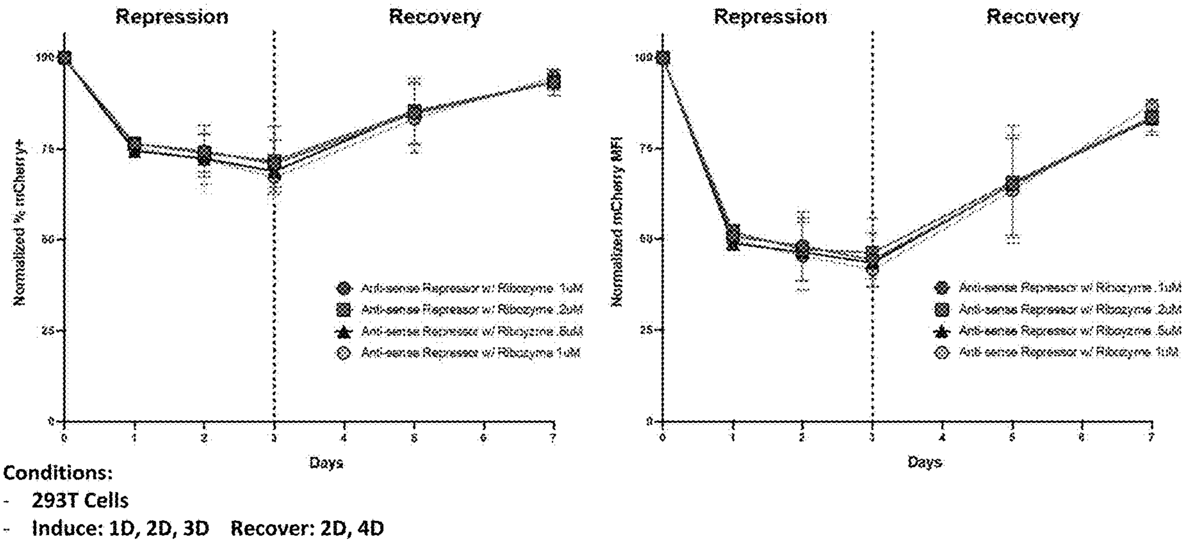
FIG. 11 show results of repression of mCherry with an exemplary inducible-repressor circuit shown in FIG. 10, comprising a RZ and synTF-MNAS, in the presence of 4-OHT for d0-d3 (at 0.1 μM, 0.2 μM, 0.5 μM and 1 μM) for duplicate experiments and for four days after 4-OHT removal (d4-d7), showing greater repression of mCherry as compared to the construct in the top pane of FIG. 7.

In some embodiments, the second transcription unit of the synthetic inducible repressor construct comprises a spacer, which can be located 3' of the GOI and 5' of the second promoter (see, e.g., FIG. 7). In some embodiments, where the second transcription unit comprises a synTF-MNAS, the spacer can be located 3' of the GOI and 5' of the synTF-MNAS.

As used herein, a "spacer" is at least one nucleotide inserted near the TATA start site in order to permit optimal transcription. Activity of the promoter is dependent on the length of the spacer as well as the spacer sequence composition. A spacer allows for the docking of various proteins involved in transcription, including but not limited to the RNA polymerase, activators, and transcription factors. The location of the spacer can be located upstream of the promoter between position −1 and position −215. A spacer can be at least one nucleotide, at least two nucleotides, at least three nucleotides, at least four nucleotides, at least five nucleotides, at least six nucleotides, at least seven nucleotides, at least eight nucleotides, at least nine nucleotides, at least ten nucleotides, at least eleven nucleotides, at least twelve nucleotides, at least thirteen nucleotides, at least fourteen nucleotides, at least fifteen nucleotides, at least sixteen nucleotides, at least seventeen nucleotides, at least eighteen nucleotides, at least nineteen nucleotides, at least twenty nucleotides, at least twenty-one nucleotides, at least twenty-two nucleotides, at least twenty-three nucleotides, at least twenty-four nucleotides, at least twenty-five nucleotides, at least twenty-six nucleotides, at least twenty-seven nucleotides, at least twenty-eight nucleotides, at least twenty-nine nucleotides, at least thirty nucleotides, at least thirty-one nucleotides, at least thirty-two nucleotides, at least thirty-three nucleotides, at least thirty-four nucleotides, at least thirty-five nucleotides or more.

In some embodiments, the second transcription module comprises a spacer located 3' of the GOI and 5' of the second promoter, e.g., see FIG. 7 (lower panel). Any spacer known in the art is encompassed for use in the second transcription module. A spacer can be between about 5-10 bp in length, or between about 10-20 bp, or about 20-30 bp, or about 30-40 bp, or about 40-50 bp, or about 50-75 bp or about 75-100 bp, or about 100-200 bp, or more than 200 bp in length.

In some embodiments, the synthetic inducible repressor construct does not comprise a polyA between the first and second transcription units. In some embodiments, the synthetic inducible repressor construct can comprise a polyA sequence in the second transcription unit, where the second transcription unit comprises a synTF-MNAS, and the polyA is located between the GOI and the synTF-MNAS (e.g., 3' of the GOI and 5' of the synTF-MNAS), such that after transcription of the synTF-MNAS the RNA polIII does not transcribe the antisense of the GOI.

E. Ribozome Entry (RZ) Site

In some embodiments, the second translation module comprises a Ribosome entry site (RZ) located between the second promoter and either the GOI, or the synTF-MNAS. A RZ is an RNA element that allows for translation initiation in a cap-independent manner, as part of the greater process of protein synthesis. In some embodiments, the RZ can be located 3' of the TNA and 5' of the second promoter sequence.

In one embodiment, a RZ is also referred to in the art as an "internal ribosome entry site" or "IRES," which refers to an element that promotes direct internal ribosome entry prior to transcription of a nucleic acid sequence, thereby leading to the cap-independent translation of the gene.

III. Synthetic Transcription Factors (synTFs)

Provided herein are synthetic transcription factors (synTF) that functions as inducible transcription factors that induce expression from the second transcription module as disclosed herein and can be used to induce the expression of the antisense strand of the GOI, or in alternative embodiments, the SynTF-mediated nucleic acid sequence (SynTF-MNAS). Such synthetic transcription factors can be engineered and arrayed with a given DNA specificity to form the basis for synthetic and customizable transcriptional modules, which can be used to control eukaryotic transcription. In some embodiments, the synTFs as described herein comprise orthogonally-functioning synthetic TFs that activate cognate synthetic promoters, using engineered zinc-finger arrays that direct protein-DNA recognition. In some embodiments, the DBM comprises a target nucleic acid for binding of the at least one DNA binding domain (DBD) of a synthetic transcription factor (synTF). The SynTF comprises of at least one DBD, at least one transcription activation domain (TA) and at least one nuclear localization domain. In some embodiments, the nuclear localization domain sequesters the synTF in the cytosol in the absence of an inducer, and wherein in the presence of an inducer, the nuclear localization domain moves to the cytosol in the presence of the inducer. Exemplary synTF for use in the methods, constructs and systems as disclosed herein are shown in FIGS. 2A, FIG. 10, FIG. 12C and FIG. 12D.

A. DNA Binding Domain (DBD)

In some embodiments, the synTF comprises a DNA binding domain which is a zinc finger protein. A zinc finger (ZF) protein is a finger-shaped fold in a protein that permits it to interact with nucleic acid sequences such as DNA and RNA. Such a fold is well known in the art. The fold is created by the binding of specific amino acids in the protein to a zinc atom. Zinc-finger containing proteins (also known as ZF proteins) can regulate the expression of genes as well as nucleic acid recognition, reverse transcription and virus assembly.

Described herein are synTFs comprising at least one DNA-binding domain (DBD). In some embodiments of any of the aspects, a synTF polypeptide as described herein (or a synTF polypeptide system collectively) comprises 1, 2, 3, 4, 5, or more DBD(s). In some embodiments of any of the aspects, the synTF polypeptide or system comprises one DBD. In embodiments comprising multiple DBDs, the multiple DBDs can be different individual DBDs or multiple copies of the same DBDs, or a combination of the foregoing.

In some embodiments of any of the aspects, the at least one DBD is an engineered zinc finger (ZF) binding domain. A zinc finger (ZF) is a finger-shaped fold in a protein that permits it to interact with nucleic acid sequences such as DNA and RNA. Such a fold is well known in the art. The fold is created by the binding of specific amino acids in the protein to a zinc atom. Zinc-finger containing proteins (also known as ZF proteins) can regulate the expression of genes as well as nucleic acid recognition, reverse transcription and virus assembly.

In some embodiments of any aspect described herein, in the synTF described or any ZF-containing fusion protein described herein, the individual ZFA therein described are specifically designed to bind orthogonal target DNA sequences, where each ZFA can at least four helices selected from any of the amino acid sequences consisting of: SEQ ID NO: 22-51, 52-69 or 70-80 of U.S. Pat. No. 10,138,493, the sequences of which are incorporated herein in its entirety by reference. In some embodiments of any aspect described herein, in the synTF described or any ZF-containing fusion protein described herein, the individual ZFA therein described are specifically designed to bind orthogonal target DNA sequences selected from SEQ ID NO: 82-91 of U.S. Pat. No. 10,138,493, the sequences of which are incorporated herein in its entirety by reference.

A ZF is a relatively small polypeptide domain comprising approximately 30 amino acids, which folds to form an α-helix adjacent an antiparallel β-sheet (known as a ββα-fold). The fold is stabilized by the co-ordination of a zinc ion between four largely invariant (depending on zinc finger framework type) Cys and/or His residues, as described further below. Natural zinc finger domains have been well studied and described in the literature, see for example, Miller et al., (1985) EMBO J. 4: 1609-1614; Berg (1988) Proc. Natl. Acad. Sci. USA 85: 99-102; and Lee et al., (1989) Science 245: 635-637. A ZF domain recognizes and binds to a nucleic acid triplet, or an overlapping quadruplet (as explained below), in a double-stranded DNA target sequence. However, ZFs are also known to bind RNA and proteins (Clemens, K. R. et al. (1993) Science 260: 530-533; Bogenhagen, D. F. (1993) Mol. Cell. Biol. 13: 5149-5158;

Searles, M. A. et al. (2000) J. Mol. Biol. 301: 47-60; Mackay, J. P. & Crossley, M. (1998) Trends Biochem. Sci. 23: 1-4).

In one embodiment, as used herein, the term “zinc finger” (ZF) or “zinc finger motif” (ZF motif) or “zinc finger domain” (ZF domain) refers to an individual “finger”, which comprises a beta-beta-alpha (00a)-protein fold stabilized by a zinc ion as described elsewhere herein. The Zn-coordinated ON protein fold produces a finger-like protrusion, a “finger.” Each ZF motif typically includes approximately 30 amino acids. The term “motif” as used herein refers to a structural motif. The ZF motif is a supersecondary structure having the ββα-fold that stabilized by a zinc ion.

In one embodiment, the term “ZF motif” according to its ordinary usage in the art, refers to a discrete continuous part of the amino acid sequence of a polypeptide that can be equated with a particular function. ZF motifs are largely structurally independent and may retain their structure and function in different environments. Because the ZF motifs are structurally and functionally independent, the motifs also qualify as domains, thus are often referred as ZF domains. Therefore, ZF domains are protein motifs that contain multiple finger-like protrusions that make tandem contacts with their target molecule. Typically, a ZF domain binds a triplet or (overlapping) quadruplet nucleotide sequence. Adjacent ZF domains arranged in tandem are joined together by linker sequences to form an array. A ZF peptide typically contains a ZF array and is composed of a plurality of “ZF domains”, which in combination do not exist in nature. Therefore, they are considered to be artificial or synthetic ZF peptides or proteins.

$C_2H_2$ zinc fingers ($C_2H_2$-ZFs) are the most prevalent type of vertebrate DNA-binding domain, and typically appear in tandem arrays (ZFAs), with sequential $C_2H_2$-ZFs each contacting three (or more) sequential bases. $C_2H_2$-ZFs can be assembled in a modular fashion. Given a set of modules with defined three-base specificities, modular assembly also presents a way to construct artificial proteins with specific DNA-binding preferences.

ZF-containing proteins generally contain strings or chains of ZF motifs, forming an array of ZF (ZFA). Thus, a natural ZF protein may include 2 or more ZF, i.e., a ZFA consisting of 2 or more ZF motifs, which may be directly adjacent one another (i.e. separated by a short (canonical) linker sequence), or may be separated by longer, flexible or structured polypeptide sequences. Directly adjacent ZF domains are expected to bind to contiguous nucleic acid sequences, i.e., to adjacent trinucleotides/triplets. In some cases cross-binding may also occur between adjacent ZF and their respective target triplets, which helps to strengthen or enhance the recognition of the target sequence, and leads to the binding of overlapping quadruplet sequences (Isalan et al., (1997) Proc. Natl. Acad. Sci. USA, 94: 5617-5621) By comparison, distant ZF domains within the same protein may recognize (or bind to) non-contiguous nucleic acid sequences or even to different molecules (e.g. protein rather than nucleic acid).

Engineered ZF-containing synTF proteins are chimeric proteins composed of a DNA-binding zinc finger protein domain (ZF protein domain) and another domain through which the protein exerts its effect (effector domain). In some embodiments, the effector domain may be a transcriptional activator (TA) or transcriptional repressor (TR), a methylation domain or a nuclease. DNA-binding ZF protein domain would contain engineered zinc finger arrays (ZFAs). See e.g., Khalil et al., Cell Volume 150, Issue 3, 3 Aug. 2012, Pages 647-658; U.S. Pat. No. 10,138,493; US Patent Application US20200002710A1 and U.S. Pat. No. 11,530,246; the contents of each of which are incorporated herein by reference in their entireties.

In some embodiments, the synTF useful in the methods, systems and compositions as disclosed herein are chimeric, non-natural polypeptides and suitably contain 3 or more, for example, 4, 5, 6, 8, 9, 10, 11, 12, 13, 14, 15, 16, 17, 18 or more (e.g. up to approximately 30 or 32) ZF motifs arranged adjacent one another in tandem, forming arrays of ZF motifs or ZFA. Particularly ZF-containing synTF proteins of the disclosure include at least 3 ZF, at least 4 ZF motifs, at least 5 ZF motifs, or at least 6 ZF motifs, at least 7 ZF motifs, at least 8 ZF motifs, at least 9 ZF motifs, at least 10 ZF motifs, at least 11 or at least 12 ZF motifs; and in some cases at least 18 ZF motifs. In other embodiments, the DBD of the synTF contains up to 6, 7, 8, 10, 11, 12, 16, 17, 18, 22, 23, 24, 28, 29, 30, 34, 35, 36, 40, 41, 42, 46, 47, 48, 54, 55, 56, 58, 59, or 60 ZF motifs. The ZF-containing synTF of the disclosure bind to contiguous orthogonal target nucleic acid binding sites. That is, the DBD of the synTF comprise a ZF domain that binds orthogonal target nucleic acid sequences or DBMs.

In one embodiment, as used herein, an “engineered synthetic transcription factor” or “engineered synTF” or “synTF” refers to an engineered ZF-containing chimeric protein having at least one of the following characteristics and may have more than one: bind target orthogonal specific DNA sequences (e.g., DBM as defined herein) and can transition from a non-active state to an active state in the presence of an inducer molecule, that is, they have reduced or minimal functional binding potential to a DBM in the absence of an inducer molecule. In some embodiments, a synTF as disclosed herein is minimally functional in a host eukaryotic genome; comprises an activation domain (also referred to herein as a regulator protein (or RP) that is activated in the presence of the inducer molecule. In some embodiments, synTFs are derived from mammalian protein scaffolds, conferring minimal degree of immunogenicity over other prokaryotically-derived domains; and can be packaging in viral delivery systems, such as lentiviral delivery constructs.

In another embodiment, as used herein, the term “engineered synthetic transcription factor” or “engineered synTF,” abbreviated as “synTF” or “ZF synTF,” refers to an engineered ZF containing synthetic transcription factor that is a polypeptide, in other words, a ZF-containing synthetic transcription factor protein. These synTFs contain ZF arrays (ZFA) therein for binding to specific target nucleic acid sequences. The synTF is a chimeric, fusion protein that comprises a DNA-binding, ZF-containing protein domain and an effector domain through which the synTF exerts its effect on gene expression. These synTFs can modulate gene expression, wherein the modulation is by increasing or decreasing the expression of a gene that is operably linked to a promoter that is also operably linked to the specific target nucleic acid sequence to which the DNA-binding, ZF-containing protein domain of the synTF binds.

In some embodiments, the DBD comprises a Cys2-His2 zing-finger domain. The Cys2-His2 zinc-finger domain is the most common DNA-binding motif in the human proteome and a single zinc finger contains approximately 30 amino acids. Zinc finger domains typically function by binding three consecutive base pairs of DNA via interactions of a single amino acid side chain per base pair. The modular structure of zinc-finger motifs permits the generation of several domains in series (e.g., zinc finger arrays), allowing for the recognition and targeting of extended sequences in multiples of three nucleotides. As a result, a zinc-finger protein can be designed to bind with high affinity and specificity to essentially any target site in a cellular genome.

Transcription factors (TFs) of virtually all taxa utilize Cys2-His2 zinc finger (ZF) domains to solve the combinatorial problem of DNA recognition and binding. ZF engineering can be used to purposefully re-engineer ZF DNA binding specificities to recognize a wide variety of different sequences and to covalently link them together into multi-finger arrays capable of recognizing longer DNA sequences. Notably, with Oligomerized Pool Engineering (OPEN) and other "context-dependent" engineering methods, customized multi-finger arrays have been successfully generated to create ZF nucleases (ZFNs) for highly-targeted genome modification'" and artificial TFs for modulating endogenous gene targets.

ZFs represent conserved functional domains underlying the design and function of many TFs as well as versatile scaffolds for rational engineering. These properties make ZF domains attractive candidates as the basis for synthetic elements that can not only direct transcriptional connections, but also program higher-order transcriptional and cellular outputs.

In some embodiments, the at least one DNA binding domain comprises a zinc finger domain. In some embodiments, the synthetic transcription factors described herein comprise 1, 2, 3, 4, or even 5 zinc finger domains. In one embodiment, the at least one DNA binding domain comprises a zinc finger array (e.g., a triple zinc finger array). Zinc finger arrays that recognize a unique or specific site can be designed based on the specificity of each one of the e.g., three zinc fingers in the array. Thus, in certain embodiments, the at least one DNA binding domain comprises an engineered zinc finger binding domain or engineered zinc finger array. Engineered zinc finger domains or arrays can comprise one or more mutations compared to a wild-type zinc finger. In some embodiments, the synthetic transcription factors described herein comprise a triple repeat zinc finger array.

In some embodiments, each DBD of a synTF as disclosed herein can comprise six to eight ZF motifs. The ZF motif is a small protein structural motif consisting of an a helix and an antiparallel 13 sheet (413) and is characterized by the coordination of one zinc ion by two histidine residues and two cysteine residues in the motif in order to stabilize the finger-like protrusion fold, the "finger". In some embodiments, the ZF motif in the DBD of a synTF disclosed herein is a Cys2His2 zinc finger motif. In one embodiment, the ZF motif comprises, consists essentially of, or consists of a peptide of formula II: [XO-3CX1-5CX2-7-(helix)-HX3-6H] (SEQ ID NO: 23) wherein X is any amino acid, the subscript numbers indicate the possible number of amino acid residues, C is cysteine, H is histidine, and (helix) is a-six contiguous amino acid residue peptide that forms a short alpha helix. The helix is variable. This short alpha helix forms one facet of the finger formed by the coordination of the zinc ion by two histidine residues and two cysteine residues in the ZF motif. For each DBD, the six to eight ZF motifs therein are linked to each other, NH2- to COOH—terminus by a peptide linker having about four to six amino acid residues to form an array of ZF motifs or ZFs. The finger-like protrusion fold of each ZF motif interacts with and binds nucleic acid sequence. Approximately a peptide sequence for two ZF motif interacts with and binds a six-base pair (bp) nucleic acid sequence. The multiple ZF motifs in a DBD form finger-like protrusions that would make contact with an orthogonal target DNA sequence. Hence, for example, a DBD with six ZF motifs or finger-like protrusions (a six-finger ZFs) interacts and binds a ~18-20 bp nucleic acid sequence, and an eight-finger ZFA would bind a ~24-26 bp nucleic acid sequence.

In another embodiment of any aspect described herein, the ZF motif of the DBD comprises a peptide of formula III: [X3CX2CX5-(helix)-HX3H] (SEQ ID NO: 24) wherein X is any amino acid, the subscript numbers indicate the possible number of amino acid residues, C is cysteine, H is histidine, and (helix) is a-six contiguous amino acid residue peptide that forms a short alpha helix.

In one embodiment of any aspect described herein, for a DBD of a synTF disclosed herein comprises a single ZF motif, the ZF protein domain comprises, consists essentially of, or consists of a sequence: N'-PGERPFQCRICMRNFS-(Helix 1)-HTRTHTGEKPFQCRICMRNFS-(Helix 2)-HLRTHTGSQK PFQCRICMRNFS-(Helix 3)-HTRTHTGEK PFQCRICMRNFS-(Helix 4)-HLRTHTGSQKPFQCRICMRNFS-(Helix 5)-HTRTHTGEK PFQCRICMRNFS-(Helix 6)-HLRTHLR-C' (SEQ ID NO: 25, SEQ ID NO: 73, SEQ ID NO: 74, SEQ ID NO: 75, SEQ ID NO: 76, SEQ ID NO: 77, SEQ ID NO: 78) wherein the (Helix) is a-six contiguous amino acid residue peptide that forms a short alpha helix. In one embodiment, all six of the helix 1, 2, 3, 4, 5 and 6 are distinct and different from each other. In another embodiment, all six of the helix 1, 2, 3, 4, 5 and 6 are identical to each other. Alternatively, at least two of the six helices are identical and the same with each other. In other embodiments, at least three of the six helices in a DBD are identical and the same with each other, at least four of the six helices in a DBD are identical and the same with each other, or at least five of the six helices in a DBD of the synTF are identical and the same with each other.

In some embodiments of any aspect described herein, the helices of the six to eight ZF motifs of an individual DBD disclosed herein are selected from the six-amino acid residue peptide sequences disclosed in one of the Groups 1-11 of U.S. Pat. No. 10,138,493, which is incorporated herein in its entirety by reference. Combinations of arrangements of ZF motifs for DBD for synTF are also disclosed in U.S. Pat. No. 10,138,493, which is incorporated herein in its entirety by reference.

The DNA binding domains (DBD) of the synthetic transcription factors described herein bind and recognize targeted tandem DNA binding motifs, which are typically upstream of a promoter where the control of gene expression is desired. In some embodiments, the DNA binding domain binds to DNA binding motifs comprising any of: DBM1 op, DBM2 op, or DBM3 op. In some embodiments of any aspect described herein, in the DBD of the synTF as described herein are specifically designed to bind orthogonal target DNA sequences of SEQ ID NOS: 81-91 of U.S. Pat. No. 10,138,493, which is incorporated herein in its entirety by reference.

In some embodiments, the DBD is disclosed in U.S. Pat. No. 11,530,246, which is incorporated herein in its entirety by reference. In some embodiments, a DBD of a synTF useful in the methods, systems and compositions as disclosed herein, comprises at least one amino acid sequence selected from any of SEQ ID NO: 219, 220, 380, 377, 101, 76, or 122-151, 152-169, 170-180, or 192 as disclosed in U.S. Pat. No. 11,530,246, the sequences of which are incorporated herein in their entirety by reference. In some embodiments, a DBD of a synTF useful in the methods, systems and compositions as disclosed herein, comprises at least one amino acid sequence selected from any of SEQ ID NO: 1 (ZF-1), SEQ ID NO: 2 (ZF3), SEQ ID NO: 3 (ZF10), or any of SEQ ID NO: 221-228 as disclosed in U.S. Pat. No. 11,530,246. In some embodiments, a DBD of a synTF useful in the methods, systems and compositions as disclosed herein, binds to a target DNA sequence (or DBM) of any of SEQ ID NO: 181-191 or 229-240 as disclosed in U.S. Pat. No. 11,530,246, the sequences of which are incorporated herein in their entirety by reference.

In some embodiments of any aspect described herein, the ZF backbone or ZF framework can be mutated to modulate affinity. In some embodiments, the mutations can be in regions of the ZF framework that mediate non-specific interactions with the phosphate backbone of the nucleic acid target. As a non-limiting example, a ZF framework can comprise at least 1 mutation to at least 10 mutations. As a non-limiting example, a mutation can comprise an arginine to alanine mutation, also referred to herein as a Z-to-A mutation or a Z2A mutation. As a non-limiting example, a ZF framework can comprise 1 Z2A mutation, 2 Z2A mutations, 3 Z2A mutations, 4 Z2A mutations, 5 Z2A mutations, 6 Z2A mutations, 7 Z2A mutations, 8 Z2A mutations, 9 Z2A mutations, or at least 10 Z2A mutations. In some embodiments, high affinity ZF frameworks have 3 Arginine-to-Alanine (R2A) mutations. In some embodiments, low affinity ZF frameworks have 4 R2A mutations. (see e.g., Khalil et al., Cell. 150, 647-658 2012, which is incorporated by reference in its entirety). Any such mutation(s) can be introduced into any of the ZF compositions as described herein (e.g., synTFs).

Modulating the Interaction Between the DBD and the DBM to Modulate the Inducible-Repressor Effect.

In some embodiments, in addition to modulating the number of DBMs upstream of the second promoter, one can further fine-tune the regulation of gene expression (e.g., the repression of the TNA) by adjusting the binding affinities and/or strength of the binding of synTF to the DBMs. As such, by specifying the strength and/or the number of assembly of synTF subunits, it enables single and multiple-input control of gene expression, as well as predictive and fine-tuning of the expression of the GOI. Stated differently, adjusting either the number of DBD sites for binding to the synTF (i.e., the DBM repeats) and/or the affinity of the synTF-DBM interactions (Kt), one can modulate and fine-tune the cooperative assembly and resulting gene expression. In some embodiments, the interaction of the DBD of the synTF can have a high affinity or low affinity for binding to the DNA Binding motifs (DBM) (e.g., low or high Kt).

B. Transcription Activation Domains

Synthetic transcription factors as described herein, can essentially comprise a transcriptional regulator domain, (herein sometimes referred to as an "effector domain") that regulates transcription of a gene. Such transcriptional regulator domains include transcriptional activation (TA) domains. In some embodiments, the TA domain is fused or covalently attached (e.g., cross-linked) to a DBD of the synTF.

In one embodiment, the synthetic transcription factor is a transcription activator and comprises a transcription activator element (TAE). Transcriptional activators typically bind nearby to transcriptional promoters and recruit RNA polymerase to directly initiate transcription. Repressors bind to transcriptional promoters and sterically hinder transcriptional initiation by RNA polymerase. Other transcriptional regulators serve as either an activator or a repressor depending on where it binds and cellular conditions.

In one embodiment of any aspect described herein, in the synTF as described herein comprises a transcriptional activator (TA) domain. As used herein, the term "transcriptional activator" domain refers to an effector that increases gene expression. In some embodiments of any of the aspects, the TA is selected from the group consisting of: p65; Rta; miniVPR; full VPR; VP16; VP64; p300; p300 HAT Core; and a CBP HAT domain. See e.g., U.S. Pat. Nos. 10,138,493; 10,590,182; Khalil et al., Cell Volume 150, Issue 3, 3 Aug. 2012, Pages 647-658; Vora et al., Rational design of a compact CRISPR--Cas9 activator for AAV-mediated delivery, bioRxiv 2018 doi.org/10.1101/298620; Chavez et al., Nat Methods. 2015 Apr. 12(4): 326-328; Park et al., Cell. 2019 Jan. 10, 176(1-2):227-238, e20; Hilton et al., Nature Biotechnology volume 33, pages 510-517(2015); Sajwan et al., Sci Rep. 2019; 9: 18104; the contents of each of which are incorporated herein by reference in their entireties.

In one embodiment of any aspect described herein, in the synTF as described herein, the TA domain is selected from the group consisting of a Herpes Simplex Virus Protein 16 (VP16) activation domain; an activation domain consisting of four tandem copies of VP16, a VP64 activation domain; a p65 activation domain of NFKB; an Epstein-Barr virus R transactivator (Rta) activation domain; a tripartite activator consisting of the VP64, the p65, and the Rta activation domains, the tripartite activator is known as a VPR activation domain; and a histone acetyltransferase (HAT) core domain of the human E1A-associated protein p300, known as a p300 HAT core activation domain.

In one embodiment, the VP64 activation domain is used as a transcriptional activator (see, e.g., (Seipel et al., EMBO J. 11:4961-4968 (1996)). Exemplary DNA binding domains of VP16 include, but are not limited to, 43-8 (WT), 43-8 (3×), 43-8 (×4), 42-10 (WT), 42-10 (3×) or 42-10 (x4) of VP16. Other preferred transcription activator elements include, but are not limited to, the HSV VP16 activation domain (Hagmann et al., J. Virol. 71:5952-5962 (1997); nuclear hormone receptors (see, e.g., Torchia et al., Curr. Opin. Cell. Biol. 10:373-383 (1998)); the p65 subunit of nuclear factor kappa B (Bitko & Bank, J. Virol. 72:5610-5618 (1998) and Doyle & Hunt, Neuroreport 8:2937-2942 (1997)); and EGR-1 (early growth response gene product-1; Yan et al., Proc. Natl. Acad. Sci. U.S.A. 95:8298-8303 (1998); and Liu et al., Cancer Gene Ther. 5:3-28 (1998)).

In some embodiments of any of the aspects, the TA is p65, or a functional fragment thereof. Transcription factor p65 also known as nuclear factor NF-kappa-B p65 subunit is a protein that in humans is encoded by the RELA gene. In some embodiments of any of the aspects, p65 comprises SEQ ID NO: 37 or a protein having at least 85% sequence identity to SEQ ID NO: 37. In some embodiments of any of the aspects, p65 comprises SEQ ID NO: 38 or a protein having at least 85% sequence identity to SEQ ID NO: 38. In some embodiments of any of the aspects, p65 comprises SEQ ID NO: 39 or a portion of SEQ ID NO: 39, e.g., residues 150-261, 100-261, 200-261, 1-200, 1-50, 1-100, or 50-100 of SEQ ID NO: 39. In some embodiments of any of the aspects, p65 comprises one of SEQ ID NOs: 37-47 or a polypeptide comprising a sequence that is at least 60%, at least 65%, at least 70%, at least 75%, at least 80%, at least 85%, at least 90%, at least 95%, at least 96%, at least 97%, at least 98%, or at least 99% identical to one of SEQ ID NOs: 37-47 that maintains its function. In some embodiments of any of the aspects, p65 comprises SEQ ID NO: 41 (p65 100-261) or a polypeptide comprising a sequence that is at least 60%, at least 65%, at least 70%, at least 75%, at least 80%, at least 85%, at least 90%, at least 95%, at least 96%, at least 97%, at least 98%, or at least 99% identical to SEQ ID NO: 41 that maintains the same function.

p65 (amino acids 361-551 of NFkB) Activation Domain (191 aa)

SEQ ID NO: 37

DEFPTMVFPSGQISQASALAPAPPQVLPQAPAPAPAPAMV

SALAQAPAPVPVLAPGPPQAVAPPAPKPTQAGEGTLSEAL

LQLQFDDEDLGALLGNSTDPAVFTDLASVDNSEFQQLLNQ

GIPVAPHTTEPMLMEYPEAITRLVTGAQRPPDPAPAPLGA

PGLPNGLLSGDEDFSSIADMDFSALLSQISS, p65 (full sequence, 551 aa), transcription factor p65 isoform 1 [*Homo sapiens*], NCBI Reference Sequence: NP_068810.3

SEQ ID NO: 38

MDELFPLIFPAEPAQASGPYVEIIEQPKQRGMRFRYKCEG

RSAGSIPGERSTDTTKTHPTIKINGYTGPGTVRISLVTKD

PPHRPHPHELVGKDCRDGFYEAELCPDRCIHSFQNLGIQC

VKKRDLEQAISQRIQTNNNPFQVPIEEQRGDYDLNAVRLC

FQVTVRDPSGRPLRLPPVLSHPIFDNRAPNTAELKICRVN

RNSGSCLGGDEIFLLCDKVQKEDIEVYFTGPGWEARGSFS

QADVHRQVAIVFRTPPYADPSLQAPVRVSMQLRRPSDREL

SEPMEFQYLPDTDDRHRIEEKRKRTYETFKSIMKKSPFSG

PTDPRPPPRRIAVPSRSSASVPKPAPQPYPFTSSLSTINY

DEFPTMVFPSGQISQASALAPAPPQVLPQAPAPAPAPAMV

SALAQAPAPVPVLAPGPPQAVAPPAPKPTQAGEGTLSEAL

LQLQFDDEDLGALLGNSTDPAVFTDLASVDNSEFQQLLNQ

GIPVAPHTTEPMLMEYPEAITRLVTGAQRPPDPAPAPLGA

PGLPNGLLSGDEDFSSIADMDFSALLSQISS, p65 1-261 (261 aa)

SEQ ID NO: 39

SQYLPDTDDRHRIEEKRKRTYETFKSIMKKSPFSGPTDPR

PPPRRIAVPSRSSASVPKPAPQPYPFTSSLSTINYDEFPT

MVFPSGQISQASALAPAPPQVLPQAPAPAPAPAMVSALAQ

APAPVPVLAPGPPQAVAPPAPKPTQAGEGTLSEALLQLQF

DDEDLGALLGNSTDPAVFTDLASVDNSEFQQLLNQGIPVA

PHTTEPMLMEYPEAITRLVTGAQRPPDPAPAPLGAPGLPN

GLLSGDEDFSSIADMDFSALL, p65 150-261 (112 aa)

SEQ ID NO: 40

SLSEALLQLQFDDEDLGALLGNSTDPAVFTDLASVDNSEF

QQLLNQGIPVAPHTTEPMLMEYPEAITRLVTGAQRPPDPA

PAPLGAPGLPNGLLSGDEDFSSIADMDFSALL, p65 100-261 (162 aa)

SEQ ID NO: 41

SVLPQAPAPAPAPAMVSALAQAPAPVPVLAPGPPQAVAPP

APKPTQAGEGTLSEALLQLQFDDEDLGALLGNSTDPAVFT

DLASVDNSEFQQLLNQGIPVAPHTTEPMLMEYPEAITRLV

TGAQRPPDPAPAPLGAPGLPNGLLSGDEDFSSIADMDFSA

LL,

-continued p65 200-261 (62 aa)

SEQ ID NO: 42

SPHTTEPMLMEYPEAITRLVTGAQRPPDPAPAPLGAPGLP

NGLLSGDEDFSSIADMDFSALL, p65 1-200 (200 aa)

SEQ ID NO: 43

SQYLPDTDDRHRIEEKRKRTYETFKSIMKKSPFSGPTDPR

PPPRRIAVPSRSSASVPKPAPQPYPFTSSLSTINYDEFPT

MVFPSGQISQASALAPAPPQVLPQAPAPAPAPAMVSALAQ

APAPVPVLAPGPPQAVAPPAPKPTQAGEGTLSEALLQLQF

DDEDLGALLGNSTDPAVFTDLASVDNSEFQQLLNQGIPVA, p65 1-150 (150 aa)

SEQ ID NO: 44

SQYLPDTDDRHRIEEKRKRTYETFKSIMKKSPFSGPTDPR

PPPRRIAVPSRSSASVPKPAPQPYPFTSSLSTINYDEFPT

MVFPSGQISQASALAPAPPQVLPQAPAPAPAPAMVSALAQ

APAPVPVLAPGPPQAVAPPAPKPTQAGEGT, p65 1-100 (100 aa)

SEQ ID NO: 45

SQYLPDTDDRHRIEEKRKRTYETFKSIMKKSPFSGPTDPR

PPPRRIAVPSRSSASVPKPAPQPYPFTSSLSTINYDEFPT

MVFPSGQISQASALAPAPPQ, p65 50-150 (101 aa)

SEQ ID NO: 46

SRSSASVPKPAPQPYPFTSSLSTINYDEFPTMVFPSGQIS

QASALAPAPPQVLPQAPAPAPAPAMVSALAQAPAPVPVLA

PGPPQAVAPPAPKPTQAGEGT, p65 143-261 (119 aa)

SEQ ID NO: 47

PTQAGEGTLSEALLQLQFDDEDLGALLGNSTDPAVFTDLA

SVDNSEFQQLLNQGIPVAPHTTEPMLMEYPEAITRLVTGA

QRPPDPAPAPLGAPGLPNGLLSGDEDFSSIADMDFSALL,

In some embodiments of any of the aspects, the TA is Rta, or a functional fragment thereof. Rta is an Epstein-Barr virus R transactivator (Rta) activation domain. In some embodiments of any of the aspects, Rta comprises SEQ ID NO: 48 or a protein having at least 85% sequence identity to SEQ ID NO: 48. In some embodiments of any of the aspects, Rta comprises a portion of SEQ ID NO: 48, e.g., residues 75-190, 125-190, 50-175, 75-175, 100-175, or 125-175 of SEQ ID NO: 48. In some embodiments of any of the aspects, Rta comprises one of SEQ ID NOs: 48-54 or a polypeptide comprising a sequence that is at least 60%, at least 65%, at least 70%, at least 75%, at least 80%, at least 85%, at least 90%, at least 95%, at least 96%, at least 97%, at least 98%, or at least 99% identical to one of SEQ ID NOs: 48-54 that maintains its function. In some embodiments of any of the aspects, Rta comprises SEQ ID NO: 50 (Rta 125-190) or a polypeptide comprising a sequence that is at least 60%, at least 65%, at least 70%, at least 75%, at least 80%, at least 85%, at least 90%, at least 95%, at least 96%, at least 97%, at least 98%, or at least 99% identical to SEQ ID NO: 50 that maintains the same function.

Rta (full sequence, 1-190; 190 aa)

SEQ ID NO: 48
RDSREGMFLPKPEAGSAISDVFEGREVCQPKRIRPFHPPG
SPWANRPLPASLAPTPTGPVHEPVGSLTPAPVPQPLDPAP
AVTPEASHLLEDPDEETSQAVKALREMADTVIPQKEEAAI
CGQMDLSHPPPRGHLDELTTTLESMTEDLNLDSPLTPELN
EILDTFLNDECLLHAMHISTGLSIFDTSLF,

Rta (75-190; 116 aa)

SEQ ID NO: 49
PLDPAPAVTPEASHLLEDPDEETSQAVKALREMADTVIPQ
KEEAAICGQMDLSHPPPRGHLDELTTTLESMTEDLNLDSP
LTPELNEILDTFLNDECLLHAMHISTGLSIFDTSLF,

Rta (125-190; 66 aa)

SEQ ID NO: 50
DLSHPPPRGHLDELTTTLESMTEDLNLDSPLTPELNEILD
TFLNDECLLHAMHISTGLSIFDTSLF,

Rta (50-175; 126 aa)

SEQ ID NO: 51
SSLAPTPTGPVHEPVGSLTPAPVPQPLDPAPAVTPEASHL
LEDPDEETSQAVKALREMADTVIPQKEEAAICGQMDLSHP
PPRGHLDELTTTLESMTEDLNLDSPLTPELNEILDTFLND
ECLLHA,

Rta (75-175; 101 aa)

SEQ ID NO: 52
PLDPAPAVTPEASHLLEDPDEETSQAVKALREMADTVIPQ
KEEAAICGQMDLSHPPPRGHLDELTTTLESMTEDLNLDSP
LTPELNEILDTFLNDECLLHA,

Rta (100-175; 76 aa)

SEQ ID NO: 53
SVKALREMADTVIPQKEEAAICGQMDLSHPPPRGHLDELT
TTLESMTEDLNLDSPLTPELNEILDTFLNDECLLHA,

Rta (125-175; 51 aa)

SEQ ID NO: 54
DLSHPPPRGHLDELTTTLESMTEDLNLDSPLTPELNEILD
TFLNDECLLHA,

In some embodiments of any of the aspects, the TA is VPR, or a functional fragment thereof. VPR is a tripartite activator consisting of the VP64, the p65, and the Rta activation domains. In some embodiments of any of the aspects, VPR comprises VP64 (e.g., SEQ ID NO: 58), p65 (e.g., any one of SEQ ID NOs: 37-47 or a polypeptide with at least 85% sequence identity to any one of SEQ ID NOs: 37-47 that maintains the same function), and Rta (e.g., any one of SEQ ID NOs: 48-54 or a polypeptide with at least 85% sequence identity to any one of SEQ ID NOs: 58-54 that maintains the same function). In some embodiments of any of the aspects, VPR comprises one of SEQ ID NOs: 55, 56, or a polypeptide comprising a sequence that is at least 60%, at least 65%, at least 70%, at least 75%, at least 80%, at least 85%, at least 90%, at least 95%, at least 96%, at least 97%, at least 98%, or at least 99% identical to one of SEQ ID NOs: 55 or 56, that maintains its function.

miniVPR, comprising the p65 (100-261 aa; SEQ ID NO: 41) truncation and the RTA (125-190 aa; SEQ ID NO: 50) truncation; bold text indicates VP64 (SEQ ID NO: 58); italicized text indicates SV40 NLS (SEQ ID NO: 65); bold italicized text indicates p65 (100-261 aa; SEQ ID NO: 41); double underlined text indicates RTA (125-190 aa; SEQ ID NO: 50).

SEQ ID NO: 55
GRADALDDFDLDMLGSDALDDFDLDMLGSDALDDFDLDML
GSDALDDFDLDMLINSRSSGS*PKKKRKV*GSGGGSGGSGS*V*
*LPQAPAPAPAPAMVSALAQAPAPVPVLAPGPPQAVAPPAP*
*KPTQAGEGTLSEALLQLQFDDEDLGALLGNSTDPAVFTDL*
*ASVDNSEFQQLLNQGIPVAPHTTEPMLMEYPEAITRLVTG*
*AQRPPDPAPAPLGAPGLPNGLLSGDEDFSSIADMDFSALL*
SGGGSGGSGSDLSHPPPRGHLDELTTTLESMTEDLNLDSP
LTPELNEILDTFLNDECLLHAMHISTGLSIEDTSLE, full VPR; bold text indicates VP64 (SEQ ID NO: 58); italicized text indicates SV40 NLS (SEQ ID NO: 65); bold italicized text indicates p65 (SEQ ID NO: 118); double underlined text indicates RTA (SEQ ID NO: 48).

SEQ ID NO: 56
GRADALDDFDLDMLGSDALDDFDLDMLGSDALDDFDLDML
GSDALDDFDLDMLINSRSSGS*PKKKRKV*G*SQYLPDTDDRH*
*RIEEKRKRTYETFKSIMKKSPFSGPTDPRPPPRRIAVPSR*
*SSASVPKPAPQPYPFTSSLSTINYDEFPTMVFPSGQISQA*
*SALAPAPPQVLPQAPAPAPAPAMVSALAQAPAPVPVLAPG*
*PPQAVAPPAPKPTQAGEGTLSEALLQLQFDDEDLGALLGN*
*STDPAVFTDLASVDNSEFQQLLNQGIPVAPHTTEPMLMEY*
*PEAITRLVTGAQRPPDPAPAPLGAPGLPNGLLSGDEDFSS*
*IADMDFSALL*GSGSGSRDSREGMFLPKPEAGSAISDVFEG
REVCQPKRIRPFHPPGSPWANRPLPASLAPTPTGPVHEPV
GSLTPAPVPQPLDPAPAVTPEASHLLEDPDEETSQAVKAL
REMADTVIPQKEEAAICGQMDLSHPPPRGHLDELTTTLES
MTEDLNLDSPLTPELNEILDTFLNDECLLHAMHISTGLSI
EDTSLE,

In some embodiments of any of the aspects, the TA comprises the Herpes Simplex Virus Protein 16 (VP16) activation domain. In some embodiments of any of the aspects, the TA comprises the VP64 activation domain, which comprises four tandem copies of VP16. In some embodiments of any of the aspects, the TA comprises one of SEQ ID NOs: 207, 208, or a polypeptide comprising a sequence that is at least 60%, at least 65%, at least 70%, at least 75%, at least 80%, at least 85%, at least 90%, at least 95%, at least 96%, at least 97%, at least 98%, or at least 99% identical to one of SEQ ID NOs: 57 or 58, that maintains its function.

VP16 (11 aa)

SEQ ID NO: 57

DALDDFDLDML

VP64 (53 aa), with the VP16 domain indicated by bold text,

SEQ ID NO: 58

GRADALDDFDLDMLGSDALDDFDLDMLGSDALDDFDLDML

GSDALDDFDLDML,

In some embodiments of any of the aspects, the TA comprises p300 or a functional fragment thereof. The adenovirus E1A-associated cellular p300 transcriptional co-activator protein functions as histone acetyltransferase that regulates transcription via chromatin remodeling. In some embodiments of any of the aspects, p300 comprises SEQ ID NO: 59 or a protein having at least 85% sequence identity to SEQ ID NO: 59. In some embodiments of any of the aspects, p300 comprises a portion of SEQ ID NO: 59, e.g., residues 1048-1664 of SEQ ID NO: 59. In some embodiments of any of the aspects, the TA comprises the p300 HAT Core activation domain. In some embodiments of any of the aspects, p300 comprises SEQ ID NO: 60 or a protein having at least 85% sequence identity to SEQ ID NO: 60. In some embodiments of any of the aspects, the TA comprises one of SEQ ID NOs: 59, 60, or a polypeptide comprising a sequence that is at least 60%, at least 65%, at least 70%, at least 75%, at least 80%, at least 85%, at least 90%, at least 95%, at least 96%, at least 97%, at least 98%, or at least 99% identical to one of SEQ ID NOs: 59, 60, that maintains its function.

human acetyltransferase p300 (2414 aa), bold text indicates the core activation domain

SEQ ID NO: 59

MAENVVEPGPPSAKRPKLSSPALSASASDGTDFGSLFDLE

HDLPDELINSTELGLINGGDINQLQTSLGMVQDAASKHKQ

LSELLRSGSSPNLNMGVGGPGQVMASQAQQSSPGLGLINS

MVKSPMTQAGLTSPNMGMGTSGPNQGPTQSTGMMNSPVNQ

PAMGMNTGMNAGMNPGMLAAGNGQGIMPNQVMNGSIGAGR

GRQNMQYPNPGMGSAGNLLTEPLQQGSPQMGGQTGLRGPQ

PLKMGMMNNPNPYGSPYTQNPGQQIGASGLGLQIQTKTVL

SNNLSPFAMDKKAVPGGGMPNMGQQPAPQVQQPGLVTPVA

QGMGSGAHTADPEKRKLIQQQLVLLLHAHKCQRREQANGE

VRQCNLPHCRTMKNVLNHMTHCQSGKSCQVAHCASSRQII

SHWKNCTRHDCPVCLPLKNAGDKRNQQPILTGAPVGLGNP

SSLGVGQQSAPNLSTVSQIDPSSIERAYAALGLPYQVNQM

PTQPQVQAKNQQNQQPGQSPQGMRPMSNMSASPMGVNGGV

GVQTPSLLSDSMLHSAINSQNPMMSENASVPSLGPMPTAA

QPSTTGIRKQWHEDITQDLRNHLVHKLVQAIFPTPDPAAL

KDRRMENLVAYARKVEGDMYESANNRAEYYHLLAEKIYKI

QKELEEKRRTRLQKQNMLPNAAGMVPVSMNPGPNMGQPQP

GMTSNGPLPDPSMIRGSVPNQMMPRITPQSGLNQFGQMSM

AQPPIVPRQTPPLQHHGQLAQPGALNPPMGYGPRMQQPSN

-continued

QGQFLPQTQFPSQGMNVTNIPLAPSSGQAPVSQAQMSSSS

CPVNSPIMPPGSQGSHIHCPQLPQPALHQNSPSPVPSRTP

TPHHTPPSIGAQQPPATTIPAPVPTPPAMPPGPQSQALHP

PPRQTPTPPTTQLPQQVQPSLPAAPSADQPQQQPRSQQST

AASVPTPTAPLLPPQPATPLSQPAVSIEGQVSNPPSTSST

EVNSQAIAEKQPSQEVKMEAKMEVDQPEPADTQPEDISES

KVEDCKMESTETEERSTELKTEIKEEEDQPSTSATQSSPA

PGQSKKKIFKPEELRQALMPTLEALYRQDPESLPFRQPVD

PQLLGIPDYFDIVKSPMDLSTIKRKLDTGQYQEPWQYVDD

IWLMFNNAWLYNRKTSRVYKYCSKLSEVFEQEIDPVMQSL

GYCCGRKLEFSPQTLCCYGKQLCTIPRDATYYSYQNRYHF

CEKCENEIQGESVSLGDDPSQPQTTINKEQFSKRKNDTLD

PELFVECTECGRKMHQICVLHHEIIWPAGFVCDGCLKKSA

RTRKENKFSAKRLPSTRLGTFLENRVNDFLRRQNHPESGE

VTVRVVHASDKTVEVKPGMKARFVDSGEMAESFPYRTKAL

FAFEEIDGVDLCFFGMHVQEYGSDCPPPNQRRVYISYLDS

VHFFRPKCLRTAVYHEILIGYLEYVKKLGYTTGHIWACPP

SEGDDYIFHCHPPDQKIPKPKRLQEWYKKMLDKAVSERIV

HDYKDIFKQATEDRLTSAKELPYFEGDFWPNVLEESIKEL

EQEEEERKREENTSNESTDVTKGDSKNAKKKNNKKTSKNK

SSLSRGNKKKPGMPNVSNDLSQKLYATMEKHKEVFFVIRL

IAGPAANSLPPIVDPDPLIPCDLMDGRDAFLTLARDKHLE

FSSLRRAQWSTMCMLVELHTQSQDRFVYTCNECKHHVETR

WHCTVCEDYDLCITCYNTKNHDHKMEKLGLGLDDESNNQQ

AAATQSPGDSRRLSIQRCIQSLVHACQCRNANCSLPSCQK

MKRVVQHTKGCKRKTNGGCPICKQLIALCCYHAKHCQENK

CPVPFCLNIKQKLRQQQLQHRLQQAQMLRRRMASMQRTGV

VGQQQGLPSPTPATPTTPTGQQPTTPQTPQPTSQPQPTPP

NSMPPYLPRTQAAGPVSQGKAAGQVTPPTPPQTAQPPLPG

PPPAAVEMAMQIQRAAETQRQMAHVQIFQRPIQHQMPPMT

PMAPMGMNPPPMTRGPSGHLEPGMGPTGMQQQPPWSQGGL

PQPQQLQSGMPRPAMMSVAQHGQPLNMAPQPGLGQVGISP

LKPGTVSQQALQNLLRTLRSPSSPLQQQQVLSILHANPQL

LAAFIKQRAAKYANSNPQPIPGQPGMPQGQPGLQPPTMPG

QQGVHSNPAMQNMNPMQAGVQRAGLPQQQPQQQLQPPMGG

MSPQAQQMNMNHNTMPSQFRDILRRQQMMQQQQQGAGPG

IGPGMANHNQFQQPQGVGYPPQQQQRMQHHMQQMQQGNMG

QIGQLPQALGAEAGASLQAYQQRLLQQQMGSPVQPNPMSP

QQHMLPNQAQSPHLQGQQIPNSLSNQVRSPQPVPSPRPQS

QPPHSSPSPRMQPQPSPHHVSPQTSSPHPGLVAAQANPME

-continued

QGHFASPDQNSMLSQLASNPGMANLHGASATDLGLSTDNS

DLNSNLSQSTLDIH, p300 HAT Core activation domain (617 aa)

SEQ ID NO: 60

IFKPEELRQALMPTLEALYRQDPESLPFRQPVDPQLLGIP

DYFDIVKSPMDLSTIKRKLDTGQYQEPWQYVDDIWLMFNN

AWLYNRKTSRVYKYCSKLSEVFEQEIDPVMQSLGYCCGRK

LEFSPQTLCCYGKQLCTIPRDATYYSYQNRYHFCEKCFNE

IQGESVSLGDDPSQPQTTINKEQFSKRKNDTLDPELFVEC

TECGRKMHQICVLHHEIIWPAGFVCDGCLKKSARTRKENK

FSAKRLPSTRLGTFLENRVNDFLRRQNHPESGEVTVRVVH

ASDKTVEVKPGMKARFVDSGEMAESFPYRTKALFAFEEID

GVDLCFFGMHVQEYGSDCPPPNQRRVYISYLDSVHFFRPK

CLRTAVYHEILIGYLEYVKKLGYTTGHIWACPPSEGDDYI

FHCHPPDQKIPKPKRLQEWYKKMLDKAVSERIVHDYKDIF

KQATEDRLTSAKELPYFEGDFWPNVLEESIKELEQEEEER

KREENTSNESTDVTKGDSKNAKKKNNKKTSKNKSSLSRGN

KKKPGMPNVSNDLSQKLYATMEKHKEVFFVIRLIAGPAAN

SLPPIVDPDPLIPCDLMDGRDAFLTLARDKHLEFSSLRRA

QWSTMCMLVELHTQSQD,

In some embodiments of any of the aspects, the TA comprises CBP or a functional fragment thereof. CBP (CREB (Cyclic AMP-Responsive Element-Binding Protein) Binding Protein; CREBBP) is involved in the transcriptional coactivation of many different transcription factors and has intrinsic histone acetyltransferase activity. In some embodiments of any of the aspects, CBP is derived from *Homo sapiens, Drosophila melanogaster*, or any other organism expressing a homologous CBP protein. In some embodiments of any of the aspects, the TA comprises the CBP HAT Core activation domain. In some embodiments of any of the aspects, the TA comprises one of SEQ ID NOs: 61-63, or a polypeptide comprising a sequence that is at least 60%, at least 65%, at least 70%, at least 75%, at least 80%, at least 85%, at least 90%, at least 95%, at least 96%, at least 97%, at least 98%, or at least 99% identical to one of SEQ ID NOs: 61-63, that maintains its function.

*Homo sapiens* CBP, histone acetyltransferase (HAT)-domain; residues 1342-1649 of CREB-binding protein isoform a [*Homo sapiens*], NCBI Reference Sequence: NP_004371.2; residues 1304-1611 of CREB-binding protein isoform b [*Homo sapiens*], NCBI Reference Sequence: NP_001073315.1.

SEQ ID NO: 61

VNKFLRRQNHPEAGEVFVRVVASSDKTVEVKPGMKSRFVD

SGEMSESFPYRTKALFAFEEIDGVDVCFFGMHVQEYGSDC

PPPNTRRVYISYLDSIHFFRPRCLRTAVYHEILIGYLEYV

KKLGYVTGHIWACPPSEGDDYIFHCHPPDQKIPKPKRLQE

WYKKMLDKAFAERIIHDYKDIFKQATEDRLTSAKELPYFE

-continued

GDFWPNVLEESIKELEQEEEERKKEESTAASETTEGSQGD

SKNAKKKNNKKTNKNKSSISRANKKKPSMPNVSNDLSQKL

YATMEKHKEVFFVIHLHAGPVINTLPPI, residues 1954-2267 of nejire, isoform E [*Drosophilia melanogaster*], NCBI Reference Sequence: NP_001259387.1, HAT_KAT11, Histone acetylation protein

SEQ ID NO: 62

VNNFLKKKEAGAGEVHIRVVSSSDKCVEVKPGMRRRFVEQ

GEMMNEFPYRAKALFAFEEVDGIDVCFFGMHVQEYGSECP

APNTRRVYIAYLDSVHFFRPRQYRTAVYHEILLGYMDYVK

QLGYTMAHIWACPPSEGDDYIFHCHPTDQKIPKPKRLQEW

YKKMLDKGMIERIIQDYKDILKQAMEDKLGSAAELPYFEG

DFWPNVLEESIKELDQEEEEKRKQAEAAEAAAAANLFSIE

ENEVSGDGKKKGQKKAKKSNKSKAAQRKNSKKSNEHQSGN

DLSTKIYATMEKHKEVFFVIRLHSAQSAASLAPI, aa 1696-2329 from *Drosophila* CBP (nejire), NCBI Reference Sequence: NP_001259387.1, including the bromodomain, PHD domain, and HAT domain

SEQ ID NO: 63

NGKYSDPWEYVDDVWLMFDNAWLYNRKTSRVYRYCTKLSE

VFEAEIDPVMQALGYCCGRKYTFNPQVLCCYGKQLCTIPR

DAKYYSYQNRYTYCQKCFNDIQGDTVTLGDDPLQSQTQIK

KDQFKEMKNDHLELEPFVNCQECGRKQHQICVLWLDSIWP

GGFVCDNCLKKKNSKRKENKFNAKRLPTTKLGVYIETRVN

NFLKKKEAGAGEVHIRVVSSSDKCVEVKPGMRRRFVEQGE

MMNEFPYRAKALFAFEEVDGIDVCFFGMHVQEYGSECPAP

NTRRVYIAYLDSVHFFRPRQYRTAVYHEILLGYMDYVKQL

GYTMAHIWACPPSEGDDYIFHCHPTDQKIPKPKRLQEWYK

KMLDKGMIERIIQDYKDILKQAMEDKLGSAAELPYFEGDF

WPNVLEESIKELDQEEEEKRKQAEAAEAAAAANLFSIEEN

EVSGDGKKKGQKKAKKSNKSKAAQRKNSKKSNEHQSGNDL

STKIYATMEKHKEVFFVIRLHSAQSAASLAPIQDPDPLLT

CDLMDGRDAFLTLARDKHFEFSSLRRAQFSTLSMLYELHN

QGQDKFVYTCNHCKTAVETRYHCTVCDDFDLCIVCKEKVG

HQHKMEKLGFDIDDGSALADHKQANPQEARKQSI,

Repressors:

In some embodiments, where the synthetic transcription factor is desired to repress gene expression, such a synTF can be made without a transcription activator element such that the synTF binds to the GOI promoter and directly represses expression or sterically hinders the binding of the basal transcription machinery. Alternatively, in some embodiments, a synTF useful in the methods, systems and composition as disclosed herein comprises a repressor regulatory element (TR), such as the KRAB repressor form the human KOX-1 gene (Thiesen et al., New Biologist 2:363-374 (1990); Margolin et al., Proc. Natl. Acad. Sci. U.S.A. 91:4509-4513 (1994); Pengue et al., Nucl. Acids Res. 22:2908-2914 (1994); Witzgall et al., Proc. Natl. Acad. Sci. U.S.A. 91:4514-4518 (1994)). In another embodiment, KAP-1, a KRAB co-repressor, is used with KRAB (Friedman et al., Genes Dev. 10:2067-2078 (1996)). Alternatively, KAP-1 can be used alone with a zinc finger protein. Other preferred transcription factor domains that act as transcriptional repressors include MAD (see, e.g., Sommer et al., J. Biol. Chem. 273:6632-6642 (1998); Gupta et al., Oncogene 16:1149-1159 (1998); Queva et al., Oncogene 16:967-977 (1998); Larsson et al., Oncogene 15:737-748 (1997); Laherty et al., Cell 89:349-356 (1997); and Cultraro et al., Mol Cell. Biol. 17:2353-2359 (19977)); FKHR (forkhead in rhabdosarcoma gene; Ginsberg et al., Cancer Res. 15:3542-3546 (1998); Epstein et al., Mol. Cell. Biol. 18:4118-4130 (1998)); EGR-1 (early growth response gene product-1; Yan et al., Proc. Natl. Acad Sci. U.S.A. 95:8298-8303 (1998); and Liu et al., Cancer Gene Ther. 5:3-28 (1998)); the ets2 repressor factor repressor domain (ERD; Sgouras et al., EMBO J. 14:4781-4793 ((19095)); p65; and the MAD smSIN3 interaction domain (SID; Ayer et al., Mol. Cell. Biol. 16:5772-5781 (1996)).

Transcriptional regulators for use in accordance with the invention include any transcriptional regulator described herein or known to one of ordinary skill in the art. Examples of genes encoding transcriptional regulators that may be used in accordance with the invention include, without limitation, those regulators provided in Table 63 of U.S. Patent Application No. 2012/0003630, which is incorporated herein in its entirety by reference.

In some embodiments of any of the aspects, the transcriptional ED is a transcriptional repressor (TR) domain. As used herein, the term "transcriptional repressor" domain refers to an effector that decreases gene expression. In some embodiments of any of the aspects, the TR is selected from the group consisting of: KRAB; KRAB-MeCP2; Hp1a; DNMT3B; EED; and HDAC4. See e.g., U.S. Pat. Nos. 10,138,493; 10,590,182; Khalil et al., Cell Volume 150, Issue 3, 3 Aug. 2012, Pages 647-658; Park et al., Cell. 2019 Jan. 10, 176(1-2):227-238, e20; Yeo et al., Nature Methods volume 15, pages 611-616(2018); Bintu et al., Science. 2016 Feb. 12; 351(6274): 720-724; the contents of each of which are incorporated herein by reference in their entireties.

In some embodiments of any of the aspects, the TR comprises KRAB, or a functional fragment thereof. The Krüppel associated box (KRAB) domain is a category of transcriptional repression domains present in approximately 400 human zinc finger protein-based transcription factors (KRAB zinc finger proteins), and it associates with other chromatin regulators that write or read H3K9me3. In some embodiments of any of the aspects, the TR comprises KRAB-MeCP2, a bipartite repressor domain. In some embodiments of any of the aspects, KRAB domain comprises one of SEQ ID NOs: 72, 97, 214-215 as disclosed in U.S. Pat. No. 11,530,246, or a polypeptide comprising a sequence that is at least 60%, at least 65%, at least 70%, at least 75%, at least 80%, at least 85%, at least 90%, at least 95%, at least 96%, at least 97%, at least 98%, or at least 99% identical to one of SEQ ID NOs: 72, 97, or 214-215 as disclosed in U.S. Pat. No. 11,530,246, that maintains its function. In some embodiments of any of the aspects, the TR comprises the transcription repression domain (TRD) domain of MeCP2, or a functional fragment thereof. In some embodiments of any of the aspects, the transcription repression domain (TRD) domain of MeCP2 comprises SEQ ID NO: 216 as disclosed in U.S. Pat. No. 11,530,246 or a polypeptide comprising a sequence that is at least 60%, at least 65%, at least 70%, at least 75%, at least 80%, at least 85%, at least 90%, at least 95%, at least 96%, at least 97%, at least 98%, or at least 99% identical to SEQ ID NO: 216 as disclosed in U.S. Pat. No. 11,530,246, that maintains its function.

In one embodiment, the TA domain of the synTF as disclosed herein is the VP64 activation domain comprising the sequence:

(SEQ. ID. NO: 58)
```
GRADALDDFDLDMLGSDALDDFDLDMLGSDALDDFDLDML

GSDALDDFDLDML.
```

In one embodiment, the effector domain of the synTF as disclosed herein is the p65 activation domain of NFKB comprising the sequence:

(SEQ ID NO: 37)
```
DEFPTMVFPSGQISQASALAPAPPQVLPQAPAPAPAPAMV

SALAQAPAPVPVLAPGPPQAVAPPAPKPTQAGEGTLSEAL

LQLQFDDEDLGALLGNSTDPAVFTDLASVDNSEFQQLLNQ

GIPVAPHTTEPMLMEYPEAITRLVTGAQRPPDPAPAPLGA

PGLPNGLLSGDEDFSSIADMDFSALLSQISS.
```

In one embodiment, the effector domain of the synTF as disclosed herein is the KRAB repressive domain comprising the sequence:

(SEQ ID NO. 64)
```
MDAKSLTAWSRTLVTFKDVFVDFTREEWKLLDTAQQILYR

NVMLENYKNLVSLGYQLTKPDVILRLEKGEEPWLVEREIH

QETHPDSETAFEIKSSV.
```

C. Nuclear Localization Domain

Aspects of the technology relate to synTF that is activated by an inducer molecule, e.g., a small molecule inducer, where the inducer results in the translocation of the synTF to the nucleus of the cell where it can imitate expression from the second promoter. In some embodiments, the ligand binds to a nuclear translocation domain (which is also referred to herein as a cytosolic sequestering domain). In some embodiments, a synTF useful in the methods, system and composition as disclosed herein is a synTF comprising a cytosolic sequestering domain as is disclosed in U.S. Pat. No. 11,530,246, which is incorporated herein in its reference. Disclosed in U.S. Pat. No. 11,530,246, are synTFs that comprise a regulator protein, and thus the synTF is activated by an inducer molecule by a variety of different mechanisms depending on the attached regulator protein, where the regulator protein can be selected from any of: a repressible protease activation domain, a Dregon domain, a induced-degradation domain, a induced-proximity domains, or a cytosolic sequestering domains. Any synTFs disclosed in U.S. Pat. No. 11,530,246 is encompassed for use in the methods, compositions and systems as disclosed herein for inducible and reversible repression of a GOI.

In some embodiments, a synTF useful in the methods, system and composition as disclosed herein comprises a cytosolic sequestering domains (also referred to herein as a nuclear translocation domain), e.g., such as those disclosed in U.S. Pat. No. 11,530,246.

In several aspects, a synTF useful in the methods, system and composition as disclosed herein comprises a cytosolic sequestering domain or protein, also referred to herein as a translocation domain. As used herein, the term "cytosolic sequestering domain" refers to a domain that influences the subcellular location of the synTF to which it is linked, e.g., through the binding of a ligand. In certain embodiments, the cytosolic sequestering domain sequesters the synTF in the cytosol in the absence of the ligand, and in the presence of the ligand the synTF can translocate to the cell's nucleus for inducing gene expression.

In some embodiments, and without wishing to be bound by theory, a synTF useful in the methods, system and composition as disclosed herein comprises a regulator protein that is a translocation domain. In some embodiments, a translocation domain is a cytosolic sequestering protein, for example, one exemplary cytosolic sequestering protein is ERT2 and variants thereof. SynTFs comprising a translocation domain, e.g., a cytosolic sequestering protein can also be referred to herein as "Translocation Domain SynTF". In such embodiments of the systems, compositions and methods disclosed herein, the DBD is directly linked or indirectly linked (or coupled) to the effector domain (ED) (e.g., the transactivation domain or TA), and TA is linked to the cytosolic sequestering protein regulator protein. In alternative embodiments, the cytosolic sequestering protein can be attached to either to the ED, or DBD or located between the DBD and ED. The cytosolic sequestering protein controls the cellular localization of the synTF. In such an embodiment, in the absence of a ligand that binds to the cytosolic sequestering protein, the cytosolic sequestering protein sequesters the activation domain (e.g., ED) and coupled DBD in the cytosol, and therefore the synTF remains in the cytosol, and the TA of the synTF is not brought into proximity of the transcription start site of the gene (or the ED dissociates from the start site), and therefore the TA can not initiate gene expression from the second promoter. In contrast, in the in the presence of a ligand that binds to the cytosolic sequestering protein, the cytosolic sequestering protein is inhibited, allowing the DBD-TA of the synTF can translocate from the cytosol to the nucleus where the DBD can bind to the DNA binding motif (DBM) of the synthetic inducer repressor construct, and the transactivation domain (TA), can control gene expression from the second promoter in the synthetic inducible-repressor construct (i.e., inducing the transcription of the synTF-MNAS).

In some embodiments of any of the aspects, a synTF polypeptide as described herein (or a synTF polypeptide system collectively) comprises 1, 2, 3, 4, 5, or more cytosolic sequestering domain(s). In some embodiments of any of the aspects, the synTF polypeptide or system comprises one cytosolic sequestering domain. In embodiments comprising multiple cytosolic sequestering domains, the multiple cytosolic sequestering domains can be different individual cytosolic sequestering domains or multiple copies of the same cytosolic sequestering domain, or a combination of the foregoing.

In some embodiments of any of the aspects, the cytosolic sequestering protein comprises a ligand binding domain (LBD), wherein in the presence of the ligand, the sequestering of the protein to the cytosol is inhibited. In some embodiments of any of the aspects, cytosolic sequestering protein further comprises a nuclear localization signal (NLS), wherein in the absence of the ligand the NLS is inhibited thereby preventing translocation of the sequestering protein to the nucleus, and wherein in the presence of the ligand the nuclear localization signal is exposed enabling translocation of the sequestering protein to the nucleus. Accordingly, when the ligand is absent, the synTF is sequestered to the cytosol. When the ligand is present, the synTF is translocated to the nucleus.

In some embodiments of any of the aspects, the sequestering protein comprises at least a portion of the estrogen receptor (ER). The ER naturally associates with cytoplasmic factors in the cell in the absence of cognate ligands, effectively sequestering itself in the cytoplasm. Binding of cognate ligands, such as estrogen or other steroid hormone derivatives, cause a conformational change to the receptor that allow dissociation from the cytoplasmic complexes and expose a nuclear localization signal, permitting translocation into the nucleus.

In some embodiments of any of the aspects, the sequestering protein comprises SEQ ID NO: 334 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NO: 334 as disclosed in U.S. Pat. No. 11,530,246, that maintains the same function. In some embodiments of any of the aspects, the sequestering protein comprises a portion of the ER (e.g., SEQ ID NO: 334 as disclosed in U.S. Pat. No. 11,530,246), e.g., the C-terminal ligand-binding and nuclear localization domains of ER. In some embodiments of any of the aspects, the sequestering protein comprises residues 282-595 of SEQ ID NO: 334 as disclosed in U.S. Pat. No. 11,530,246, or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to residues 282-595 of SEQ ID NO: 334 as disclosed in U.S. Pat. No. 11,530,246.

```
SEQ ID NO: 66 as disclosed in
U.S. Pat. No. 11,530,246 is
estrogen receptor isoform 1
[Homo sapiens]; NCBI Reference
Sequence: NP_000116.2 (595 aa)
MTMTLHTKASGMALLHQIQGNELEPLNRPQLKIPLERPLG

EVYLDSSKPAVYNYPEGAAYEFNAAAAANAQVYGQTGLPY

GPGSEAAAFGSNGLGGFPPLNSVSPSPLMLLHPPPQLSPF

LQPHGQQVPYYLENEPSGYTVREAGPPAFYRPNSDNRRQG

GRERLASTNDKGSMAMESAKETRYCAVCNDYASGYHYGVW

SCEGCKAFFKRSIQGHNDYMCPATNQCTIDKNRRKSCQAC

RLRKCYEVGMMKGGIRKDRRGGRMLKHKRQRDDGEGRGEV

GSAGDMRAANLWPSPLMIKRSKKNSLALSLTADQMVSALL

DAEPPILYSEYDPTRPFSEASMMGLLTNLADRELVHMINW

AKRVPGFVDLTLHDQVHLLECAWLEILMIGLVWRSMEHPG

KLLFAPNLLLDRNQGKCVEGMVEIFDMLLATSSRFRMMNL

QGEEFVCLKSIILLNSGVYTFLSSTLKSLEEKDHIHRVLD

KITDTLIHLMAKAGLTLQQQHQRLAQLLLILSHIRHMSNK

GMEHLYSMKCKNVVPLYDLLLEMLDAHRLHAPTSRGGASV

EETDQSHLATAGSTSSHSLQKYYITGEAEGFPATV
```

In some embodiments of any of the aspects, the estrogen receptor comprises at least one mutation that decreases its ability to bind to its natural ligands (e.g., estradiol) but maintains the ability to bind to synthetic ligands such as tamoxifen and analogs thereof. In some embodiments of any of the aspects, the estrogen receptor comprises at least one of the following mutations: G400V, G521R, L539A, L540A, M543A, L544A, V595A or any combination thereof. In some embodiments of any of the aspects, a triple G400V/MS43A/L544A ER mutant is referred to herein as ERT2. In some embodiments of any of the aspects, the sequestering protein further comprises a V595A mutation from ER (e.g., SEQ ID NO: 334). In some embodiments of any of the aspects, the sequestering protein comprises an estrogen ligand binding domain (ERT2) or a variant thereof. In some embodiments of any of the aspects, the sequestering protein comprises ERT, ERT2, ERT3, or a variant thereof. In some embodiments of any of the aspects, the sequestering protein comprises one of SEQ ID NOs: 74, 335-337 as disclosed in U.S. Pat. No. 11,530,246, or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 74, 335-337, that maintains the same function. See e.g., U.S. Pat. No. 7,112,715; Feil et al., Biochemical and Biophysical Research Communications, Volume 237, Issue 3, 28 Aug. 1997, Pages 752-757; Felker et al., PLoS One. 2016 Apr. 14; 11(4):e0152989; the contents of each of which are incorporated herein by reference in their enteritis.

SEQ ID NO: 67 as disclosed in U.S. Pat. No. 11,530,246 is ERT2 (314 aa), G400V, M543A, L544A, and V595A mutations from ER (e.g., SEQ ID NO: 334) shown in bold, double underlined text

```
SAGDMRAANLWPSPLMIKRSKKNSLALSLTADQMVSALLD
AEPPILYSEYDPTRPFSEASMMGLLTNLADRELVHMINWA
KRVPGFVDLTLHDQVHLLECAWLEILMIGLVWRSMEHPVK
LLFAPNLLLDRNQGKCVEGMVEIFDMLLATSSRFRMMNLQ
GEEFVCLKSIILLNSGVYTFLSSTLKSLEEKDHIHRVLDK
ITDTLIHLMAKAGLTLQQQHQRLAQLLLILSHIRHMSNKG
MEHLYSMKCKNVVPLYDLLLEAADAHRLHAPTSRGGASVE
ETDQSHLATAGSTSSHSLQKYYITGEAEGFPATA
```

SEQ ID NO: 68 as disclosed in U.S. Pat. No. 11,530,246 is ERT (314 aa), G521R mutation from ER (e.g., SEQ ID NO: 334) shown in bold, double underlined text

```
SAGDMRAANLWPSPLMIKRSKKNSLALSLTADQMVSALLD
AEPPILYSEYDPTRPFSEASMMGLLTNLADRELVHMINWA
KRVPGFVDLTLHDQVHLLECAWLEILMIGLVWRSMEHPGK
LLFAPNLLLDRNQGKCVEGMVEIFDMLLATSSRFRMMNLQ
GEEFVCLKSIILLNSGVYTFLSSTLKSLEEKDHIHRVLDK
ITDTLIHLMAKAGLTLQQQHQRLAQLLLILSHIRHMSNKR
MEHLYSMKCKNVVPLYDLLLEMLDAHRLHAPTSRGGASVE
ETDQSHLATAGSTSSHSLQKYYITGEAEGFPATV
```

-continued

SEQ ID NO: 69 as disclosed in U.S. Pat. No. 11,530,246 is ERT3 (314 aa), M543A, L544A, and V595A mutations from ER (e.g., SEQ ID NO: 334) shown in bold, double underlined text

```
SAGDMRAANLWPSPLMIKRSKKNSLALSLTADQMVSALLD
AEPPILYSEYDPTRPFSEASMMGLLTNLADRELVHMINWA
KRVPGFVDLTLHDQVHLLECAWLEILMIGLVWRSMEHPGK
LLFAPNLLLDRNQGKCVEGMVEIFDMLLATSSRFRMMNLQ
GEEFVCLKSIILLNSGVYTFLSSTLKSLEEKDHIHRVLDK
ITDTLIHLMAKAGLTLQQQHQRLAQLLLILSHIRHMSNKG
MEHLYSMKCKNVVPLYDLLLEAADAHRLHAPTSRGGASVE
ETDQSHLATAGSTSSHSLQKYYITGEAEGFPATA
```

SEQ ID NO: 70 as disclosed in U.S. Pat. No. 11,530,246 is ERT (314 aa), G400V, L539A, L540A mutations from ER (e.g., SEQ ID NO: 334) shown in bold, double underlined text

```
SAGDMRAANLWPSPLMIKRSKKNSLALSLTADQMVSALLD
AEPPILYSEYDPTRPFSEASMMGLLTNLADRELVHMINWA
KRVPGFVDLTLHDQVHLLECAWLEILMIGLVWRSMEHPVK
LLFAPNLLLDRNQGKCVEGMVEIFDMLLATSSRFRMMNLQ
GEEFVCLKSIILLNSGVYTFLSSTLKSLEEKDHIHRVLDK
ITDTLIHLMAKAGLTLQQQHQRLAQLLLILSHIRHMSNKG
MEHLYSMKCKNVVPLYDAALEMLDAHRLHAPTSRGGASVE
ETDQSHLATAGSTSSHSLQKYYITGEAEGFPATV
```

In some embodiments of any of the aspects, the cytosol sequestering protein (or nuclear localization domain) of the synTF polypeptide is in combination with 1, 2, 3, 4, 5, or more ligands. In some embodiments of any of the aspects, the sequestering protein of the synTF polypeptide is in combination with one ligand. In embodiments comprising multiple ligands, the multiple ligands can be different individual ligands or multiple copies of the same ligands, or a combination of the foregoing.

In some embodiments of any of the aspects, the ligand is estradiol (PubChem CID: 5757), or an analog thereof. In some embodiments of any of the aspects, the ligand is a synthetic ligand of the estrogen receptor, such as tamoxifen or a derivative thereof the ligand is selected from: tamoxifen, 4-hydroxytamoxifen (4OHT), endoxifen, and Fulvestrant, wherein binding of the ligand to the ERT (e.g., ERT2) exposes the NLS and results in nuclear translocation of the ERT. In some embodiments of any of the aspects, the ligand is 4-hydroxytamoxifen (4-OHT), shown below (PubChem CID: 449459), which can also be referred to as afimoxifene. In some embodiments of any of the aspects, the ligand is 4-Hydroxy-N-desmethyltamoxifen, shown below (PubChem CID: 10090750), which can also be referred to as endoxifen. In some embodiments of any of the aspects, the ligand is Fulvestrant shown below (PubChem CID 104741), which can

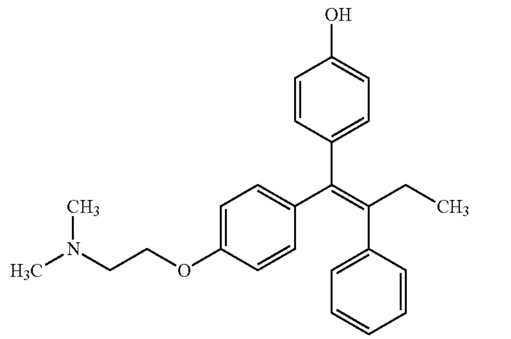

trans-4-OHT

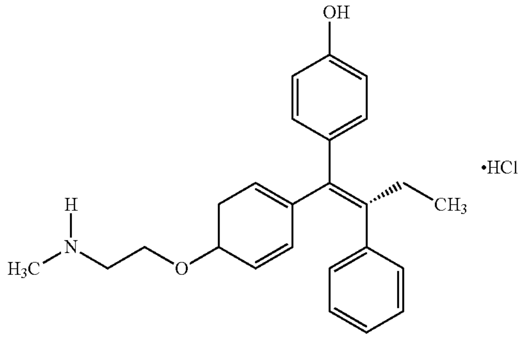

Endoxifen also be referred to as ICI 182,780.

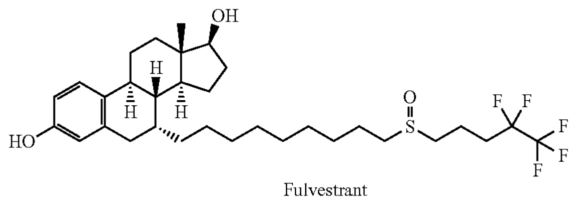

Fulvestrant

In some embodiments of any of the aspects, the sequestering protein of the synTF is a transmembrane receptor sequestering protein, and the DNA-binding domain (DBD) and transcriptional effector (TE) domain of the synTF are linked to the cytosolic side of the transmembrane domain of the receptor. In the absence of a specific ligand for the transmembrane protein, the DBD and TA of the synTF are sequestered to the cellular membrane. In the presence of a specific ligand for the transmembrane protein, the transmembrane protein cleaves itself such that the DBD and TA of the synTF are released into the cytosol to be transported to the nucleus. Non-limiting examples of transmembrane receptor sequestering protein include a synthetic notch receptor or first and second exogenous extracellular sensors, described further herein.

In some embodiments of any the aspects, the cytosolic sequestering protein comprises a Notch receptor or a variant of endogenous Notch receptor, such as a synthetic Notch (synNotch) receptor. In some embodiments of any the aspects, the synTF comprising a synNotch comprises: (a) an extracellular domain comprising a first member of a specific binding pair that is heterologous to the Notch receptor; (b) a Notch receptor regulatory region; and (c) an intracellular domain comprising the DNA binding domain and transcriptional effector domain of the synTF. In the presence of a second member of the specific binding pair, binding of the first member of the specific binding pair to the second member of the specific binding pair induces cleavage of the binding-induced proteolytic cleavage site to activate the intracellular domain, thereby permitting the synTF to translocate to the nucleus. In the absence of a second member of the specific binding pair, the synTF remains sequestered at the cellular membrane. In some embodiments of any of the aspects, the sequestering protein comprises one of SEQ ID NOs: 338-339 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 74, 335-337, that maintains the same function. See e.g., U.S. Pat. No. 10,590,182; Morsut et al., Cell. 2016 Feb. 11; 164(4):780-91; the contents of which are incorporated herein by reference in their entireties. In some embodiments of any of the aspects, the Notch receptor regulatory region comprises Lin-12 Notch repeats A-C, heterodimerization domains HD-N and HD-C, a binding-induced proteolytic cleavage site, and a transmembrane domain. In some embodiments of any the aspects, the Notch variant is a Notch receptor where the Notch extracellular subunit (NEC) (which includes the negative regulatory region (NRR)) is partially or completely removed. In some embodiments of any of the aspects, the Notch receptor regulatory region is a truncated or modified variant of synNotch, e.g., lacking one or more of the following domains: Lin-12 Notch repeats A-C, heterodimerization domains HD-N and HD-C, a binding-induced proteolytic cleavage site, the Notch extracellular domain (NEC), the negative regulatory region (NRR), or a transmembrane domain.

SEQ ID NO: 71 as disclosed in
U.S. Pat. No. 11,530,246 is
synNotch (306 aa)
PPQIEEACELPECQVDAGNKVCNLQCNNHACGWDGGDCSL

NFNDPWKNCTQSLQCWKYFSDGHCDSQCNSAGCLFDGFDC

QLTEGQCNPLYDQYCKDHFSDGHCDQGCNSAECEWDGLDC

AEHVPERLAAGTLVLVVLLPPDQLRNNSFHFLRELSHVLH

TNVVFKRDAQGQQMIFPYYGHEEELRKHPIKRSTVGWATS

SLLPGTSGGRQRRELDPMDIRGSIVYLEIDNRQCVQSSSQ

CFQSATDVAAFLGALASLGSLNIPYKIEAVKSEPVEPPLP

SQLHLMYVAAAAFVLLFFVGCGVLLS

SEQ ID NO: 72 as disclosed in
U.S. Pat. No. 11,530,246 is
synNotch (358 aa)
PCVGSNPCYNQGTCEPTSENPFYRCLCPAKFNGLLCHILD

YSFTGGAGRDIPPPQIEEACELPECQVDAGNKVCNLQCNN

HACGWDGGDCSLNFNDPWKNCTQSLQCWKYFSDGHCDSQC

NSAGCLFDGFDCQLTEGQCNPLYDQYCKDHFSDGHCDQGC

NSAECEWDGLDCAEHVPERLAAGTLVLVVLLPPDQLRNNS

FHFLRELSHVLHTNVVFKRDAQGQQMIFPYYGHEEELRKH

PIKRSTVGWATSSLLPGTSGGRQRRELDPMDIRGSIVYLE

IDNRQCVQSSSQCFQSATDVAAFLGALASLGSLNIPYKIE

-continued

AVKSEPVEPPLPSQLHLMYVAAAAFVLLFFVGCGVLLS

Suitable first members of a specific binding pairs (e.g., of the synNotch) include, but are not limited to, antibody-based recognition scaffolds; antibodies (i.e., an antibody-based recognition scaffold, including antigen-binding antibody fragments); non-antibody-based recognition scaffolds; antigens (e.g., endogenous antigens; exogenous antigens; etc.); a ligand for a receptor; a receptor; a target of a non-antibody-based recognition scaffold; an Fc receptor (e.g., FcγRIIIa; FcγRIIIb; etc.); an extracellular matrix component; and the like.

Specific binding pairs (e.g., of the synNotch) include, e.g., antigen-antibody specific binding pairs, where the first member is an antibody (or antibody-based recognition scaffold) that binds specifically to the second member, which is an antigen, or where the first member is an antigen and the second member is an antibody (or antibody-based recognition scaffold) that binds specifically to the antigen; ligand-receptor specific binding pairs, where the first member is a ligand and the second member is a receptor to which the ligand binds, or where the first member is a receptor, and the second member is a ligand that binds to the receptor; non-antibody-based recognition scaffold-target specific binding pairs, where the first member is a non-antibody-based recognition scaffold and the second member is a target that binds to the non-antibody-based recognition scaffold, or where the first member is a target and the second member is a non-antibody-based recognition scaffold that binds to the target; adhesion molecule-extracellular matrix binding pairs; Fc receptor-Fc binding pairs, where the first member comprises an immunoglobulin Fc that binds to the second member, which is an Fc receptor, or where the first member is an Fc receptor that binds to the second member which comprises an immunoglobulin Fc; and receptor-co-receptor binding pairs, where the first member is a receptor that binds specifically to the second member which is a co-receptor, or where the first member is a co-receptor that binds specifically to the second member which is a receptor.

In some embodiments of any the aspects, the transmembrane receptor sequestering protein comprises first and second exogenous extracellular sensors, wherein said first exogenous extracellular sensor comprises: (a) a ligand binding domain, (b) a transmembrane domain, (c) a protease cleavage site, and (d) the DBD and TA of the synTF; and wherein said second exogenous extracellular sensor comprises: (e) a ligand binding domain, (f) a transmembrane domain, and (g) a protease domain. Such a system can also be referred to as a modular extracellular sensor architecture (MESA) system. In the presence of a ligand for the first and second exogenous extracellular sensors, the two receptors are brought into proximity, permitting the protease to cleave the protease cleavage site and release the DBD and TA of the synTF into the cytosol to be translocated to the nucleus. In the absence of a ligand for the first and second exogenous extracellular sensors, the DBD and TA of the synTF remains sequestered at the cell membrane. In some embodiments of any of the aspects, the protease comprises any protease as described herein (e.g., NS3), and the protease cleavage site comprises an NS3 protease cleavage site as described herein. See e.g., US Patent Application 2014/0234851; Daringer et al., ACS Synth. Biol. 2014, 3, 12, 892-902.

Any type of suitable ligand binding domain (LB) can be employed with transmembrane receptor sequestering protein. Ligand binding domains can, for example, be derived from either an existing receptor ligand-binding domain or from an engineered ligand binding domain. Existing ligand-binding domains could come, for example, from cytokine receptors, chemokine receptors, innate immune receptors (TLRs, etc.), olfactory receptors, steroid and hormone receptors, growth factor receptors, mutant receptors that occur in cancer, neurotransmitter receptors. Engineered ligand-binding domains can be, for example, single-chain antibodies (see scFv constructs discussion below), engineered fibronectin based binding proteins, and engineered consensus-derived binding proteins (e.g., based upon leucine-rich repeats or ankyrin-rich repeats, such as DARPins). The ligand can be any cognate ligand of such ligand-binding domains.

In alternative embodiments, the synTF useful in the methods, systems and compositions as disclosed herein comprise a regulator protein that is a self-cleaving protease, for example, one exemplary protease is NS3. A SynTFs comprising a self-cleaving protease can also be referred to herein as "repressible proteases SynTF", and is disclosed in U.S. Pat. No. 11,530,246, which is incorporated herein in its reference. In such embodiments of the systems, compositions and methods disclosed herein, the DBD is directly linked or indirectly linked (or coupled) to the effector domain, e.g., transactivation domain, and the protease regulator protein (typically located between the DBD and TA) controls the coupling of the DBD to the TA. In such an embodiment, in the presence of an agent which inhibits the regulator protein (i.e., NS3 protein), the DBD and TA remain coupled or intact (either directly or indirectly) and the TA can control gene expression from the second promoter (i.e., turning on gene expression of the synTF-MNAS if the ED is a TA, or, in some embodiments, repressing gene expression if the effector domain (ED) is a repressor). In such an embodiment, in the absence of an agent which inhibits the regulator protein (i.e., NS3 protein), the linkage between the DBD and TA is broken or cleaved, and therefore the TA is not brought into proximity of the transcription start site of the gene (or the TA dissociates from the start site), and therefore the TA can no longer initiate gene expression of the synTF-MNAS, or alternatively, a repressor domain can no longer repress gene expression of the synTF-MNAS.

In another embodiment of the systems, compositions and methods as disclosed herein, the synTF comprises a regulator protein that is a pair of inducer proximity domains (referred to as an "IPD pair") which is located between the DBD and TA, where each domain of the IPD come together in the presence of an inducer agent, and therefore linking the DBD and TA and controlling gene expression of the synTF-MNAS. SynTFs comprising an IPD pair can also be referred to herein as a "heterodimerization domain SynTF" and are disclosed in U.S. Pat. No. 11,530,246, which is incorporated herein in its reference. For example, in such embodiments, where the regulator protein is an IPD pair, each domain of the IPD pair is attached to either the DBD or the TA, such that in the presence of an inducer agent, each domain of the IPD bind to the inducer agent, thereby indirectly coupling the DBD with the TA, such that when the DBD binds to a second promoter region, the TA can control gene expression of the synTF-MNAS from the second promoter (i.e., turning on gene expression if the ED is a TA, or repressing gene expression if the ED is a TR). In alternative embodiments where the RP is an IPD pair, in the absence of the inducer agent, the DBD and TA remain uncoupled, and therefore the TA is not in a position to regulate gene transcription of synTF-MNAS from the second promoter. Exemplary IPD pairs and their inducing agents are disclosed in U.S. Pat. No. 11,530,246, which is incorporated herein in its reference.

IV. Vectors

In some embodiments, vectors comprising the synthetic inducible repressor construct as disclosed herein can be delivered to a cell, in some embodiments, to a subject.

Further still, the present disclosure provides delivering to a subject synthetic inducible repressor construct as disclosed herein, where the synthetic inducible repressor construct is present in a vector, and the subject can be administered an inducer as disclosed herein to regulate (e.g., repress) the expression of the GOI, or edit the GOI transcript expressed from the synthetic inducible repressor construct in the subject.

In some embodiments, vectors comprising synthetic inducible repressor construct as disclosed herein can also be delivered to a subject. In some embodiments, a subject is a mammalian subject. In some embodiments, a subject is a human subject. In some embodiments, the subject has a disease or disorder, and the GOI is a therapeutic molecule and/or prophylactic molecule as disclosed herein.

Methods of the present disclosure may include (use of) any of the synthetic inducible repressor construct as disclosed herein.

In some embodiments, a synthetic inducible repressor construct as disclosed herein can be delivered to cells using a viral delivery system (e.g., retroviral, adenoviral, adeno-association, helper-dependent adenoviral systems, hybrid adenoviral systems, herpes simplex, pox virus, lentivirus, Epstein-Barr virus) or a non-viral delivery system (e.g., physical: naked DNA, DNA bombardment, electroporation, hydrodynamic, ultrasound or magnetofection; or chemical: cationic lipids, different cationic polymers or lipid polymer) (Nayerossadat N et al. Adv Biomed Res. 2012; 1: 27, incorporated herein by reference). In some embodiments, the non-viral based deliver system is a hydrogel-based delivery system (see, e.g., Brandl F, et al. Journal of Controlled Release, 2010, 142(2): 221-228, incorporated herein by reference).

In some embodiments, a synthetic inducible repressor construct as disclosed herein and/or cells comprising a synthetic inducible repressor construct as disclosed herein, can be delivered to a subject (e.g., a mammalian subject, such as a human subject) by any in vivo delivery method known in the art. For example, engineered genetic constructs and/or cells may be delivered intravenously. In some embodiments, engineered genetic constructs and/or cells are delivered in a delivery vehicle (e.g., non-liposomal nanoparticle or liposome). In some embodiments, a synthetic inducible repressor construct as disclosed herein and/or cells comprising the same are delivered systemically to a subject having a cancer or other disease and activated (transcription is activated) specifically in cancer cells or diseased cells of the subject.

Essentially any expression vector including, but not limited to, plasmids and viral vectors can be used to express the components of the system for regulating gene expression as described herein. The vectors described herein can include any number of sequences known to those of skill in the art, such as promoters (e.g., constitutive or inducible), enhancers, long-terminal repeats (LTRs), multiple cloning sites, restriction sequences, and the like. It will be appreciated by those of ordinary skill in the art that a vector can be designed to include any number of optional sequences. Some non-limiting examples of these sequences, referred to herein as "viral components" are described herein.

The vectors described herein can contain zero, one or more of the following components: promoters and/or enhancers, untranslated regions (UTRs), Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, and polynucleotides encoding self-cleaving polypeptides, or epitope tags.

Promoters used with the vector compositions described herein can be constitutive, or inducible.

As used herein, the term "constitutive promoter" refers to a promoter that continually or continuously allows for transcription of an operably linked sequence. Constitutive promoters may be a "ubiquitous promoter" that allows expression in a wide variety of cell and tissue types or a "tissue-specific promoter" that allows expression in a restricted variety of cell and tissue types. Illustrative ubiquitous promoters include, but are not limited to, a cytomegalovirus (CMV) immediate early promoter, a viral simian virus 40 (SV40) (e.g., early or late), a Moloney murine leukemia virus (MoMLV) LTR promoter, a Rous sarcoma virus (RSV) LTR, a herpes simplex virus (HSV) (thymidine kinase) promoter, H5, P7.5, and P11 promoters from vaccinia virus, an elongation factor 1-alpha (EF1a) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPA5), heat shock protein 90 kDa beta, member 1 (HSP90B1), heat shock protein 70 kDa (HSP70), β-kinesin (β-KIN), the human ROSA 26 locus (Irions et al., Nature Biotechnology 25, 1477-1482 (2007)), a Ubiquitin C promoter (UBC), a phosphoglycerate kinase-1 (PGK) promoter, a cytomegalovirus enhancer/chicken β-actin (CAG) promoter, and a β-actin promoter.

As used herein, "conditional expression" may refer to any type of conditional expression including, but not limited to, inducible expression; repressible expression; expression in cells or tissues having a particular physiological, biological, or disease state, etc. Certain embodiments of the methods and compositions herein provide conditional expression of a synTF e.g., expression is controlled by subjecting a host cell, to a treatment or condition that causes the polynucleotide to be expressed or that causes an increase or decrease in expression of the synTF encoded by the nucleic acid. The concept of inducible expression of a polypeptide is well known in the art and/or could be envisioned by one of skill in the art. As such, the mechanisms of inducible gene expression are not described at length herein.

An inducible promoter/system useful in the methods and systems as disclosed herein can be induced by one or more physiological conditions, such as changes in pH, temperature, cell surface binding, and the concentration of one or more extrinsic or intrinsic inducing agents. The extrinsic inducer or inducing agent can comprise amino acids and amino acid analogs, nucleic acids, protein transcriptional activators and repressors, cytokines, hormones, and combinations thereof.

Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al., 2003, Gene, 323:67), the cumate inducible gene switch (WO 2002/088346), tetracycline-dependent regulatory systems, etc.

In some embodiments, the administration or removal of an inducer or repressor as described herein results in a switch between the "on" or "off" states of the transcription of one or more components of the gene expression system described herein. Thus, as defined herein, the "on" state of a promoter operably linked to a nucleic acid sequence, refers to the state when the promoter is actively driving transcription of the operably linked nucleic acid sequence, i.e., the linked nucleic acid sequence is expressed. Several small molecule ligands have been shown to mediate regulated gene expressions, either in tissue culture cells and/or in transgenic animal models. These include the FK1012 and rapamycin immunosuppressive drugs (Spencer et al., 1993; Magari et al., 1997), the progesterone antagonist mifepristone (RU486) (Wang, 1994; Wang et al., 1997), the tetracycline antibiotic derivatives (Gossen and Bujard, 1992; Gossen et al., 1995; Kistner et al., 1996), and the insect steroid hormone ecdysone (No et al., 1996). All of these references are herein incorporated by reference. By way of further example, Yao discloses in U.S. Pat. No. 6,444,871, which is incorporated herein by reference, prokaryotic elements associated with the tetracycline resistance (tet) operon, a system in which the tet repressor protein is fused with polypeptides known to modulate transcription in mammalian cells. The fusion protein is then directed to specific sites by the positioning of the tet operator sequence. For example, the tet repressor has been fused to a transactivator (VP16) and targeted to a tet operator sequence positioned upstream from the promoter of a selected gene (Gussen et al., 1992; Kim et al., 1995; Hennighausen et al., 1995). The tet repressor portion of the fusion protein binds to the operator thereby targeting the VP16 activator to the specific site where the induction of transcription is desired. An alternative embodiment can fuse the tet repressor to the KRAB repressor domain and target this protein to an operator placed several hundred base pairs upstream of a gene. Using this system, it has been found that the chimeric protein, but not the tet repressor alone, is capable of producing a 10 to 15-fold suppression of CMV-regulated gene expression (Deuschle et al., 1995).

An exemplary repressible promoter useful in the synthetic transcription factors as disclosed herein is the Lac repressor (lacR)/operator/inducer system of *E. coli* that has been used to regulate gene expression by three different approaches: (1) prevention of transcription initiation by properly placed lac operators at promoter sites (Hu and Davidson, 1987; Brown et al., 1987; Figge et al., 1988; Fuerst et al., 1989; Deuschle et al., 1989; (2) blockage of transcribing RNA polymerase II during elongation by a LacR/operator complex (Deuschle et al. (1990); and (3) activation of a promoter responsive to a fusion between LacR and the activation domain of herpes simples virus (HSV) virion protein 16 (VP16) (Labow et al., 1990; Baim et al., 1991). In one version of the Lac system, expression of lac operator-linked sequences is constitutively activated by a LacR-VP16 fusion protein and is turned off in the presence of isopropyl-β-D-1-thiogalactopyranoside (IPTG) (Labow et al. (1990), cited supra). In another version of the system, a lacR-VP16 variant is used that binds to lac operators in the presence of IPTG, which can be enhanced by increasing the temperature of the cells (Baim et al. (1991), cited supra). Thus, in some embodiments of the aspects described herein, components of the Lac system are utilized. For example, a lac operator (LacO) can be operably linked to tissue specific promoter, and control the transcription and expression of a desired protein and another repressor protein, such as the TetR. Accordingly, the expression of the heterologous target gene is inversely regulated as compared to the expression or presence of Lac repressor in the system.

In one embodiment, the vectors described herein can include an "internal ribosome entry site" or "IRES," which refers to an element that promotes direct internal ribosome entry to the initiation codon, such as ATG, of a cistron (a protein encoding region), thereby leading to the cap-independent translation of the gene. In particular embodiments, the vectors contemplated herein may include one or more nucleic acid sequences encoding a synthetic transcription factor. To achieve efficient translation of each of the plurality of polypeptides, the polynucleotide sequences can be separated by one or more IRES sequences or polynucleotide sequences encoding self-cleaving polypeptides.

As used herein, the term "Kozak sequence" refers to a short nucleotide sequence that greatly facilitates the initial binding of mRNA to the small subunit of the ribosome and increases translation. The consensus Kozak sequence is (GCC)RCCATGG, where R is a purine (A or G) (SEQ ID NO: 29; Kozak, 1986. Cell. 44(2):283-92, and Kozak, 1987. Nucleic Acids Res. 15(20):8125-48).

In particular embodiments, vectors comprise a polyadenylation sequence 3' of a polynucleotide encoding a polypeptide to be expressed. Polyadenylation sequences can promote mRNA stability by addition of a polyA tail to the 3' end of the coding sequence and thus, contribute to increased translational efficiency. Recognized polyadenylation sites include an ideal polyA sequence (e.g., ATTAAA (SEQ ID NO: 30), ATTAAA, AGTAAA (SEQ ID NO: 32)), a bovine growth hormone polyA sequence (BGHpA), a rabbit β-globin polyA sequence (rpgpA), or another suitable heterologous or endogenous polyA sequence known in the art.

If desired, the vectors described herein can comprise a selection gene, also termed a selectable marker. Typical selection genes encode proteins that (a) confer resistance to antibiotics or other toxins, e.g., ampicillin, neomycin, hygromycin, methotrexate, Zeocin, Blastocidin, or tetracycline, (b) complement auxotrophic deficiencies, or (c) supply critical nutrients not available from complex media, e.g., the gene encoding D-alanine racemase for Bacilli. Any number of selection systems may be used to recover transformed cell lines. These include, but are not limited to, the herpes simplex virus thymidine kinase (Wigler et al., 1977. Cell 11:223-232) and adenine phosphoribosyltransferase (Lowy et al., 1990. Cell 22:817-823) genes which can be employed in tk- or aprt-cells, respectively.

The term 'nucleic acid cassette" as used herein refers to genetic sequences within the vector which can express an RNA, and subsequently a protein of interest (e.g., a synTF). The nucleic acid cassette is positionally and sequentially oriented within the vector such that the nucleic acid in the cassette can be transcribed into RNA, and when necessary, translated into a protein or a polypeptide, undergo appropriate post-translational modifications required for activity in the transformed cell, and be translocated to the appropriate compartment for biological activity by targeting to appropriate intracellular compartments or secretion into extracellular compartments. Preferably, the cassette has its 3' and 5' ends adapted for ready insertion into a vector, e.g., it has restriction endonuclease sites at each end.

When a nuclear localization signal peptide is desired on one or more of the components of the gene expression system described herein, a vector can include a nucleic acid sequence encoding such a nuclear localization sequence on the synTF.

As used herein, the term "constitutive promoter" refers to a promoter that continually or continuously allows for transcription of an operably linked sequence. Constitutive promoters may be a "ubiquitous promoter" that allows expression in a wide variety of cell and tissue types or a "tissue-specific promoter" that allows expression in a restricted variety of cell and tissue types. Illustrative ubiquitous promoters include, but are not limited to, a cytomegalovirus (CMV) immediate early promoter, a viral simian virus 40 (SV40) (e.g., early or late), a Moloney murine leukemia virus (MoMLV) LTR promoter, a Rous sarcoma virus (RSV) LTR, a herpes simplex virus (HSV) (thymidine kinase) promoter, H5, P7.5, and P11 promoters from vaccinia virus, an elongation factor 1-alpha (EF1a) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPA5), heat shock protein 90 kDa beta, member 1 (HSP90B1), heat shock protein 70 kDa (HSP70), β-kinesin (β-KIN), the human ROSA 26 locus (Irions et al., Nature Biotechnology 25, 1477-1482 (2007)), a Ubiquitin C promoter (UBC), a phosphoglycerate kinase-1 (PGK) promoter, a cytomegalovirus enhancer/chicken β-actin (CAG) promoter, and a β-actin promoter.

As used herein, "conditional expression" may refer to any type of conditional expression including, but not limited to, inducible expression; repressible expression; expression in cells or tissues having a particular physiological, biological, or disease state, etc. Certain embodiments of the methods and compositions herein provide conditional expression of a synTF e.g., expression is controlled by subjecting a host cell, to a treatment or condition that causes the polynucleotide to be expressed or that causes an increase or decrease in expression of the synTF encoded by the nucleic acid. The concept of inducible expression of a polypeptide is well known in the art and/or could be envisioned by one of skill in the art. As such, the mechanisms of inducible gene expression are not described at length herein.

An inducible promoter/system useful in the methods and systems as disclosed herein can be induced by one or more physiological conditions, such as changes in pH, temperature, cell surface binding, and the concentration of one or more extrinsic or intrinsic inducing agents. The extrinsic inducer or inducing agent can comprise amino acids and amino acid analogs, nucleic acids, protein transcriptional activators and repressors, cytokines, hormones, and combinations thereof.

Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al., 2003, Gene, 323:67), the cumate inducible gene switch (WO 2002/088346), tetracycline-dependent regulatory systems, etc.

In some embodiments, the administration or removal of an inducer or repressor as described herein results in a switch between the "on" or "off" states of the transcription of one or more components of the gene expression system described herein. Thus, as defined herein, the "on" state of a promoter operably linked to a nucleic acid sequence, refers to the state when the promoter is actively driving transcription of the operably linked nucleic acid sequence, i.e., the linked nucleic acid sequence is expressed. Several small molecule ligands have been shown to mediate regulated gene expressions, either in tissue culture cells and/or in transgenic animal models. These include the FK1012 and rapamycin immunosuppressive drugs (Spencer et al., 1993; Magari et al., 1997), the progesterone antagonist mifepristone (RU486) (Wang, 1994; Wang et al., 1997), the tetracycline antibiotic derivatives (Gossen and Bujard, 1992; Gossen et al., 1995; Kistner et al., 1996), and the insect steroid hormone ecdysone (No et al., 1996). All of these references are herein incorporated by reference. By way of further example, Yao discloses in U.S. Pat. No. 6,444,871, which is incorporated herein by reference, prokaryotic elements associated with the tetracycline resistance (tet) operon, a system in which the tet repressor protein is fused with polypeptides known to modulate transcription in mammalian cells. The fusion protein is then directed to specific sites by the positioning of the tet operator sequence. For example, the tet repressor has been fused to a transactivator (VP16) and targeted to a tet operator sequence positioned upstream from the promoter of a selected gene (Gussen et al., 1992; Kim et al., 1995; Hennighausen et al., 1995). The tet repressor portion of the fusion protein binds to the operator thereby targeting the VP16 activator to the specific site where the induction of transcription is desired. An alternative embodiment can fuse the tet repressor to the KRAB repressor domain and target this protein to an operator placed several hundred base pairs upstream of a gene. Using this system, it has been found that the chimeric protein, but not the tet repressor alone, is capable of producing a 10 to 15-fold suppression of CMV-regulated gene expression (Deuschle et al., 1995).

An exemplary repressible promoter useful in the synthetic transcription factors as disclosed herein is the Lac repressor (lacR)/operator/inducer system of *E. coli* that has been used to regulate gene expression by three different approaches: (1) prevention of transcription initiation by properly placed lac operators at promoter sites (Hu and Davidson, 1987; Brown et al., 1987; Figge et al., 1988; Fuerst et al., 1989; Deuschle et al., 1989; (2) blockage of transcribing RNA polymerase II during elongation by a LacR/operator complex (Deuschle et al. (1990); and (3) activation of a promoter responsive to a fusion between LacR and the activation domain of herpes simples virus (HSV) virion protein 16 (VP16) (Labow et al., 1990; Baim et al., 1991). In one version of the Lac system, expression of lac operator-linked sequences is constitutively activated by a LacR-VP16 fusion protein and is turned off in the presence of isopropyl-β-D-1-thiogalactopyranoside (IPTG) (Labow et al. (1990), cited supra). In another version of the system, a lacR-VP16 variant is used that binds to lac operators in the presence of IPTG, which can be enhanced by increasing the temperature of the cells (Baim et al. (1991), cited supra). Thus, in some embodiments of the aspects described herein, components of the Lac system are utilized. For example, a lac operator (LacO) can be operably linked to tissue specific promoter, and control the transcription and expression of a desired protein and another repressor protein, such as the TetR. Accordingly, the expression of the heterologous target gene is inversely regulated as compared to the expression or presence of Lac repressor in the system.

In one embodiment, the vectors described herein can include an "internal ribosome entry site" or "RZ" or "IRES," which refers to an element that promotes direct internal ribosome entry to the initiation codon, such as ATG, of a cistron (a protein encoding region), thereby leading to the cap-independent translation of the gene. In particular embodiments, the vectors contemplated herein may include one or more nucleic acid sequences encoding a synthetic transcription factor. To achieve efficient translation of each of the plurality of polypeptides, the polynucleotide sequences can be separated by one or more IRES sequences or polynucleotide sequences encoding self-cleaving polypeptides.

As used herein, the term "Kozak sequence" refers to a short nucleotide sequence that greatly facilitates the initial binding of mRNA to the small subunit of the ribosome and increases translation. The consensus Kozak sequence is (GCC)RCCATGG, where R is a purine (A or G) (SEQ ID NO: 33; Kozak, 1986. Cell. 44(2):283-92, and Kozak, 1987. Nucleic Acids Res. 15(20):8125-48).

In particular embodiments, vectors comprise a polyadenylation sequence 3' of a polynucleotide encoding a polypeptide to be expressed. Polyadenylation sequences can promote mRNA stability by addition of a polyA tail to the 3' end of the coding sequence and thus, contribute to increased translational efficiency. Recognized polyadenylation sites include an ideal polyA sequence (e.g., ATTAAA (SEQ ID NO: 30), ATTAAA (SEQ ID NO: 30), AGTAAA (SEQ ID NO: 31)), a bovine growth hormone polyA sequence (BGHpA), a rabbit β-globin polyA sequence (rpgpA), or another suitable heterologous or endogenous polyA sequence known in the art.

If desired, the vectors described herein can comprise a selection gene, also termed a selectable marker. Typical selection genes encode proteins that (a) confer resistance to antibiotics or other toxins, e.g., ampicillin, neomycin, hygromycin, methotrexate, Zeocin, Blastocidin, or tetracycline, (b) complement auxotrophic deficiencies, or (c) supply critical nutrients not available from complex media, e.g., the gene encoding D-alanine racemase for Bacilli. Any number of selection systems may be used to recover transformed cell lines. These include, but are not limited to, the herpes simplex virus thymidine kinase (Wigler et al., 1977. Cell 11:223-232) and adenine phosphoribosyltransferase (Lowy et al., 1990. Cell 22:817-823) genes which can be employed in tk- or aprt-cells, respectively.

The term 'nucleic acid cassette" as used herein refers to genetic sequences within the vector which can express an RNA, and subsequently a protein of interest (e.g., a synTF). The nucleic acid cassette is positionally and sequentially oriented within the vector such that the nucleic acid in the cassette can be transcribed into RNA, and when necessary, translated into a protein or a polypeptide, undergo appropriate post-translational modifications required for activity in the transformed cell, and be translocated to the appropriate compartment for biological activity by targeting to appropriate intracellular compartments or secretion into extracellular compartments. Preferably, the cassette has its 3' and 5' ends adapted for ready insertion into a vector, e.g., it has restriction endonuclease sites at each end.

When a nuclear localization signal peptide is desired on one or more of the components of the gene expression system described herein, a vector can include a nucleic acid sequence encoding such a nuclear localization sequence on the synTF.

IV. Cells

In some embodiments, the engineered or synthetic inducible repressor constructs as disclosed herein may be delivered systemically and activated (transcription of the constructs are activated) conditionally (based on the presence or absence of input signals) in a particular target cell.

In some embodiments, a target cell can be, for example, a target cell of a particular disease state (e.g., disease v. non-disease), a particular cell type (e.g., neuronal cell v. glial cell), or cell in a particular environmental state (e.g., T cell in a pro-inflammatory state or a T cell in an anti-inflammatory state). As provided herein, the choice of target cells is not limited to a particular type of cell or condition.

In some embodiments, a target cell is a cancerous cell, a benign tumor cell or other disease cell. Thus, in some embodiments, a synthetic inducible repressor construct as disclosed herein is delivered to a subject having tumor cells or cancer cells, and the engineered or synthetic inducible repressor constructs is present in the tumor cells or cancer cells.

A cancerous cell may be any type of cancerous cell, including, but not limited to, premalignant neoplasms, malignant tumors, metastases, or any disease or disorder characterized by uncontrolled cell growth such that it would be considered cancerous or precancerous. The cancer may be a primary or metastatic cancer. Cancers include, but are not limited to, ocular cancer, biliary tract cancer, bladder cancer, pleura cancer, stomach cancer, ovary cancer, meninges cancer, kidney cancer, brain cancer including glioblastomas and medulloblastomas, breast cancer, cervical cancer, choriocarcinoma, colon cancer, endometrial cancer, esophageal cancer, gastric cancer, hematological neoplasms including acute lymphocytic and myelogenous leukemia, multiple myeloma, AIDS-associated leukemias and adult T-cell leukemia lymphoma, intraepithelial neoplasms including Bowen's disease and Paget's disease, liver cancer, lung cancer, lymphomas including Hodgkin's disease and lymphocytic lymphomas, neuroblastomas, oral cancer including squamous cell carcinoma, ovarian cancer including those arising from epithelial cells, stromal cells, germ cells and mesenchymal cells, pancreatic cancer, prostate cancer, rectal cancer, sarcomas including leiomyosarcoma, rhabdomyosarcoma, liposarcoma, fibrosarcoma, and osteosarcoma, skin cancer including melanoma, Kaposi's sarcoma, basocellular cancer, and squamous cell cancer, testicular cancer including germinal tumors such as seminoma, non-seminoma, teratomas, choriocarcinomas, stromal tumors and germ cell tumors, thyroid cancer including thyroid adenocarcinoma and medullar carcinoma, and renal cancer including adenocarcinoma and Wilms' tumor. Commonly encountered cancers include breast, prostate, lung, ovarian, colorectal, and brain cancer. In some embodiments, the tumor is a melanoma, carcinoma, sarcoma, or lymphoma.

In some embodiments, a synthetic inducible repressor construct as disclosed can be expressed in a broad range of host cell types. In some embodiments, engineered genetic constructs are expressed in mammalian cells (e.g., human cells). In some embodiments, a synthetic inducible repressor construct as disclosed herein can be expressed in vivo, e.g., in a subject such as a human subject.

In some embodiments, engineered genetic constructs are expressed in mesenchymal stem cells (MSCs), induced pluripotent stem cells (iPSCs), embryonic stem cells (ESCs), natural killer (NK) cells, T cells, hematopoietic stem cells (HSCs), and/or other immune cells (e.g., for cells engineered ex vivo). In some embodiments, engineered genetic constructs are expressed in immune cells, muscle cells, liver cells, neurons, eye cells, ear cells, skin cells, heart cells, pancreatic cells, and/or fat cells (e.g., for cells targeted in vivo).

In some embodiments, a synthetic inducible repressor construct as disclosed herein is present in a mammalian cell. For example, in some embodiments, a synthetic inducible repressor construct as disclosed herein can be present in any of: human cells, primate cells (e.g., vero cells), rat cells (e.g., GH3 cells, OC23 cells) or mouse cells (e.g., MC3T3 cells). There are a variety of human cell lines, including, without limitation, human embryonic kidney (HEK) cells, HeLa cells, cancer cells from the National Cancer Institute's 60 cancer cell lines (NCI60), DU145 (prostate cancer) cells, Lncap (prostate cancer) cells, MCF-7 (breast cancer) cells, MDA-MB-438 (breast cancer) cells, PC3 (prostate cancer) cells, T47D (breast cancer) cells, THP-1 (acute myeloid leukemia) cells, U87 (glioblastoma) cells, SHSY5Y human neuroblastoma cells (cloned from a myeloma) and Saos-2 (bone cancer) cells. In some embodiments, a synthetic inducible repressor construct as disclosed herein is present in human embryonic kidney (HEK) cells (e.g., HEK 293 or HEK 293T cells). In some embodiments, a synthetic inducible repressor construct as disclosed herein is present in a stem cell (e.g., human stem cells) such as, for example, pluripotent stem cells (e.g., human pluripotent stem cells including human induced pluripotent stem cells (hiPSCs)). A "stem cell" refers to a cell with the ability to divide for indefinite periods in culture and to give rise to specialized cells. In some embodiments, a stem cell as defined herein does not involve the destruction of a human embryo. A "pluripotent stem cell" refers to a type of stem cell that is capable of differentiating into all tissues of an organism, but not alone capable of sustaining full organismal development. A "human induced pluripotent stem cell" refers to a somatic (e.g., mature or adult) cell that has been reprogrammed to an embryonic stem cell-like state by being forced to express genes and factors important for maintaining the defining properties of embryonic stem cells (see, e.g., Takahashi and Yamanaka, Cell 126 (4): 663-76, 2006, incorporated by reference herein). Human induced pluripotent stem cell cells express stem cell markers and are capable of generating cells characteristic of all three germ layers (ectoderm, endoderm, mesoderm).

Additional non-limiting examples of cell lines that may be used in accordance with the present disclosure include 293-T, 293-T, 3T3, 4T1, 721, 9L, A-549, A172, A20, A253, A2780, A2780ADR, A2780cis, A431, ALC, B16, B35, BCP-1, BEAS-2B, bEnd.3, BHK-21, BR 293, BxPC3, C2C12, C3H-10T1/2, C6, C6/36, Cal-27, CGR8, CHO, CML T1, CMT, COR-L23, COR-L23/5010, COR-L23/CPR, COR-L23/R23, COS-7, COV-434, CT26, D17, DH82, DU145, DuCaP, E14Tg2a, EL4, EM2, EM3, EMT6/AR1, EMT6/AR10.0, FM3, H1299, H69, HB54, HB55, HCA2, Hepalclc7, High Five cells, HL-60, HMEC, HT-29, HUVEC, J558L cells, Jurkat, JY cells, K562 cells, KCL22, KG1, Ku812, KYO1, LNCap, Ma-Mel 1, 2, 3 . . . 48, MC-38, MCF-10A, MCF-7, MDA-MB-231, MDA-MB-435, MDA-MB-468, MDCK II, MG63, MONO-MAC 6, MOR/0.2R, MRC5, MTD-1A, MyEnd, NALM-1, NCI-H69/CPR, NCI-H69/LX10, NCI-H69/LX20, NCI-H69/LX4, NIH-3T3, NW-145, OPCN/OPCT Peer, PNT-1A/PNT 2, PTK2, Raji, RBL cells, RenCa, RIN-5F, RMA/RMAS, S2, Saos-2 cells, Sf21, Sf9, SiHa, SKBR3, SKOV-3, T-47D, T2, T84, THP1, U373, U87, U937, VCaP, WM39, WT-49, X63, YAC-1 and YAR cells.

V. Uses of Engineered Inducible-Repressor System

The system for cooperative synTF assemblies as described herein is useful for engineering complex behavioral phenotypes in cellular systems, such as prokaryotic, eukaryotic, or synthetic cells, or in non-cellular systems, including test tubes, viruses and phages. The novel system for cooperative synTF assemblies as described herein combine the power of nucleic acid-based engineering methods with systems biology approaches to elicit specific levels of gene expression in cellular and non-cellular systems, such as the ability for fine-tuning single and multiple inputs for controlled gene expression.

In some embodiments of any of the aspects, the second transcriptional module further comprises a SynTF-mediated nucleic acid sequence (SynTF-MNAS). The SynTF-MNAS is operatively linked to the second promoter and encodes at least one antisense nucleic acid sequence directed against at least a portion of the TNA, and wherein the SynTF-MNAS is located 3' of the TNA and 5' of the second promoter.

In some embodiments, when the synTF is activated by the inducer molecule as described herein, the synthetic inducible repressor construct and synTF function cooperatively to reduce the expression of the GOI transcript from the first promoter as compared to the expression of the GOI from the first promoter in the absence of the inducer.

In some embodiments, when the synTF is activated in the presence of the inducer molecule as discussed herein, the synTF binds to the DBD present in the synthetic inducible repressor circuit as disclosed herein, and induces the expression of an antisense nucleic acid sequence of a portion of the GOI, or a synTF-MNAS, where the antisense nucleic acid sequence of a portion of the GOI, or a synTF-MNAS represses, or decreases, the expression of the GOI transcript expressed from the first transcription unit by at least 0.5-fold, or at least 1-fold, or at least 1.5-fold, or at least 2-fold, or at least 2.25-fold, or at least 2.5-fold, or at least 5-fold, or at least 10-fold, or at least 25-fold, or at least 50-fold or more than 50-fold, as compared to in the absence of the inducer molecule. Accordingly, as disclosed herein, the GOI is expressed in a cell from the first transcription unit of the synthetic inducible repressor circuit (where expression is initially dependent on the operatively linked first promoter), and in the presence of an inducer molecule, the synTF is activated and induces the expression an antisense molecule to the GOI or a synTF-MNAS and represses the expression of the GOI by at least 0.5-fold, or at least 1-fold, or at least 1.5-fold, or at least 2-fold, or at least 2.25-fold, or at least 2.5-fold, or at least 5-fold, or at least 10-fold, or at least 25-fold, or at least 50-fold or more than 50-fold. Accordingly, the system as disclosed herein enables gene expression, e.g., high-level gene expression of the GOI only in the absence of the inducer molecule.

As used herein, a Ribosome entry site (RZ) is an RNA element that allows for translation initiation in a cap-independent manner, as part of the greater process of protein synthesis.

The RZ can be located 3' of the TNA and 5' of the second promoter sequence.

ERT2 nuclear translocation domain, which is responsive to a small molecule (4-hydroxytamoxifen=40HT), can be used to regulate a synTF as described herein (see e.g., Indra et a. Nucleic Acids Res (1999)). The human estrogen receptor (ER) contains a ligand responsive domain that, when fused to other protein domains, can yield ligand-dependent control over activity. The domain naturally associates with cytoplasmic factors in the cell in the absence of cognate ligands, effectively sequestering itself in the cytoplasm. Binding of cognate ligands, such as estrogen or other steroid hormone derivatives, cause a conformational change to the receptor that allow dissociation from the cytoplasmic complexes and expose a nuclear localization signal, permitting translocation into the nucleus. A mutated variant of this estrogen receptor ligand binding domain (ERT2) has enhanced sensitivity to certain "orthogonal" ligands (e.g. tamoxifen, 4-hydroxytamoxifen) and decreased sensitivity to endogenous ligands (e.g. estradiol). 4-hydroxytamoxifen (40HT) is a selective modulator of the estrogen receptor that has been FDA-approved as a treatment for certain breast cancers.

VI. Definitions

Without wishing to be bound by theory, an engineered or nucleic acid (e.g., an engineered genetic construct or engineered synthetic inducer repressor construct as disclosed herein) is a nucleic acid that does not occur in nature. It should be understood, however, that while an engineered nucleic acid as a whole is not naturally-occurring, it may include nucleotide sequences that occur in nature. In some embodiments, an engineered nucleic acid comprises nucleotide sequences from different organisms (e.g., from different species). For example, in some embodiments, an engineered nucleic acid includes a murine nucleotide sequence, a bacterial nucleotide sequence, a human nucleotide sequence, and/or a viral nucleotide sequence. The term "engineered nucleic acids" includes recombinant nucleic acids and synthetic nucleic acids. A "recombinant nucleic acid" refers to a molecule that is constructed by joining nucleic acid molecules and, in some embodiments, can replicate in a live cell. A "synthetic nucleic acid" refers to a molecule that is amplified or chemically, or by other means, synthesized. Synthetic nucleic acids include those that are chemically modified, or otherwise modified, but can base pair with naturally-occurring nucleic acid molecules. Recombinant nucleic acids and synthetic nucleic acids also include those molecules that result from the replication of either of the foregoing. Engineered nucleic acid of the present disclosure may be encoded by a single molecule (e.g., included in the same plasmid or other vector) or by multiple different molecules (e.g., multiple different independently-replicating molecules).

An engineered nucleic acid (e.g., a "synthetic inducible repressor construct") of the present disclosure may be produced using standard molecular biology methods (see, e.g., Green and Sambrook, Molecular Cloning, A Laboratory Manual, 2012, Cold Spring Harbor Press). In some embodiments, engineered nucleic acid constructs are produced using GIBSON ASSEMBLY® Cloning (see, e.g., Gibson, D. G. et al. Nature Methods, 343-345, 2009; and Gibson, D. G. et al. Nature Methods, 901-903, 2010, each of which is incorporated by reference herein). GIBSON ASSEMBLY® typically uses three enzymatic activities in a single-tube reaction: 5' exonuclease, the 'Y extension activity of a DNA polymerase and DNA ligase activity. The 5' exonuclease activity chews back the 5' end sequences and exposes the complementary sequence for annealing. The polymerase activity then fills in the gaps on the annealed regions. A DNA ligase then seals the nick and covalently links the DNA fragments together. The overlapping sequence of adjoining fragments is much longer than those used in Golden Gate Assembly, and therefore results in a higher percentage of correct assemblies. In some embodiments, engineered nucleic acid constructs are produced using IN-FUSION® cloning (Takara Bio USA).

As used herein, "a target nucleic acid" or TNA can be single-stranded or double-stranded. Further, the target nucleic acids can be DNA or RNA.

As used herein, the term "DNA binding domain" or "DBD" refers to an independently folded protein domain that contains at least one structural motif that recognizes double- or single-stranded DNA. A DBD can recognize a specific DNA sequence (a recognition sequence or DNA binding motif (DBM) or have a general affinity to DNA. Some DNA-binding domains may also include nucleic acids in their folded structure. Examples for DBDs include the helix-turn-helix motif, the zinc finger (ZF) domain, the basic leucine zipper (bZIP) domain, the winged helix (WH) domain, the winged helix-turn-helix (wHTH) domain, the High Mobility Group box (HMG)-box domains, White-Opaque Regulator 3 domains and oligonucleotide/oligosaccharide folding domains. The helix-turn-helix motif is commonly found in repressor proteins and is about 20 amino acids long. The zinc finger domain is generally between 23 and 28 amino acids long and is stabilized by coordinating zinc ions with regularly spaced zinc-coordinating residues (either histidines or cysteines).

As used herein, a "synthetic transcription factor" or "synTF" or "sTF" refers to an engineered DNA binding protein that targets specific DNA sequences and can activate or repress gene expression. In one embodiment, as used herein, a "synthetic transcription factor" or "synTF" or "sTF" refers to an engineered chimeric protein comprising a DNA binding domain (DBD) that binds to a target specific DNA sequences referred to as a DNA binding motif (DBM), at least one transaction domain (TA), and at least one nuclear localization domain.

The term "transcriptional activator domain" or "TA domain" refers to a polypeptide or peptide that binds to promoters and recruits RNA polymerase to directly initiate transcription.

The term "DNA binding motif" or "DBM" or a nucleic acid "target", "target site" or "target sequence" or "DNA target sequence", or "DBM sequence" as used herein, is a nucleic acid sequence to which a DNA binding domain (DBD) (often one or more ZF motifs) of a synTF of the disclosure will bind, provided that conditions of the binding reaction are not prohibitive. A DBM sequence may be a nucleic acid molecule or a portion of a larger polynucleotide. In accordance with the disclosure, a DBM sequence for a DBD of a synTF of the disclosure may comprise a single contiguous nucleic acid sequence. These terms may also be substituted or supplemented with the terms "binding site", "binding sequence", "recognition site" or recognition sequence", which are used interchangeably.

As used herein, the term "conjugate" or "conjugation" refers to the attachment of two or more entities to form one entity. The attachment can be by means of linkers, chemical modification, peptide linkers, chemical linkers, covalent or non-covalent bonds, or protein fusion or by any means known to one skilled in the art. The joining can be permanent or reversible. In some embodiments, several linkers can be included in order to take advantage of desired properties of each linker and each protein in the conjugate. Flexible linkers and linkers that increase the solubility of the conjugates are contemplated for use alone or with other linkers as disclosed herein. Peptide linkers can be linked by expressing DNA encoding the linker to one or more proteins in the conjugate. Linkers can be acid cleavable, photocleavable and heat sensitive linkers. Methods for conjugation are well known by persons skilled in the art and are not described in detail herein.

The term "linker" refers to a polymer of amino acids to form a peptide that attaches or facilitates the functional connection of two moieties together. Linkers can have virtually any amino acid sequence, and can be rigid or flexible. Additionally, as disclosed herein, linkers can be used to join a ligand to a DBD of the synTF, and/or for joining an effector domain (e.g., TA domain, TR domain or EE domain) to a DBD of the synTF. In some embodiments, linkers will have a sequence that results in a generally flexible peptide. Small amino acids, such as glycine and alanine, are of use in creating a flexible peptide. A peptide linker or typically ranges from about 2 to about 50 amino acids in length, which is designed to facilitate the functional connection of two polypeptides into a linked fusion polypeptide. The term "functional connection" denotes a connection that maintains proper folding of the polypeptides in a three-dimensional structure that allows the linked fusion polypeptide to mimic some or all of the functional aspects or biological activities of the protein(s) from which its polypeptide constituents are derived. The term functional connection also denotes a connection that confers a degree of stability required for the resulting linked fusion polypeptide to function as desired. The creation of linker sequences is routine to those of skill in the art. A variety of different linkers are commercially available and are considered suitable for use according to the present invention.

As used herein, the term "interaction" when used in the context of the DNA binding domain (DBD) and the DNA binding motif (DBM) sequence, it refers to the binding between the DBD and its target nucleic acid sequence (DBM) as a result of the non-covalent bonds between the DNA-binding site (or fragment) of the DBD and the protein-binding site of the nucleic acid sequence of the DBM. In the context of two entities, e.g., molecules or proteins, having some binding affinity for each other, the term "interaction" refers to the binding of the two entities as a result of the non-covalent bonds between the two entities.

As used herein, "binding" refers to a non-covalent interaction between macromolecules (e.g. between DBD of the synTF and a DBM nucleic acid target site or sequence). In some cases, binding will be sequence-specific, and can be specific for one or more specific nucleotides (or base pairs) (e.g., such as between the binding of the DBD of the synTF and the DBM sequence). In some cases, binding will be specific on one or more specific amino acids. It will be appreciated, however, that not all components of a binding interaction need to be sequence-specific (e.g. non-covalent interactions with phosphate residues in a DNA backbone). Binding interactions between a DBM nucleic acid sequence and DBD of the synTF of the disclosure may be characterized by binding affinity and/or dissociation constant (Kt). Binding interactions between a ligand binding domain (LBD) and ligand of the synTF of the disclosure may be characterized by binding affinity and/or dissociation constant (Kp). A suitable dissociation constant for a DBD of the disclosure binding to its target DBM sequence may be in the order of 1 μM or lower, 1 nM or lower, or 1 pM or lower.

The term "affinity" refers to the strength of binding of two binding partners, such as a synTF to a given DNA binding motif (Kt). Typically, as the binding affinity increases, the Kt or Kp will reduce in value Affinity can refer to the strength of binding of a synTF as described herein to DNA, RNA, and/or even proteins. In some embodiments, a synTF of the disclosure is designed or selected to have sequence-specific dsDNA-binding activity. For example, the DBM site for a particular DBD is a sequence to which the DBD concerned is capable of nucleotide-specific binding. It will be appreciated, however, that depending on the amino acid sequence of a DBM, the DBD of the synTF may bind to or recognize more than one target DBM sequence, although typically one sequence will be bound in preference to any other recognized sequences, depending on the relative specificity of the individual non-covalent interactions. Thus, in some embodiments, the synTF will bind the preferred sequence with high affinity and non-target sites with low affinity (or will not bind at all: "lack of affinity"). In some embodiments, the synTFs as described herein can be designed or selected to have a desirable affinity for a given target (e.g., high affinity vs. low affinity sequence specific dsDNA-binding). It will be appreciated that high affinity binding of a synTF to a DNA binding site will deter other endogenous or synthetic transcription factors with lower affinity from displacing the high affinity binding partner to the site. Thus, selecting for high affinity binding vs. low affinity binding between two binding partners can be used to fine-tune the desired modulation of gene expression and/or the reversibility of the gene expression by modulating the strength of interaction between the two binding partners. Generally, high affinity binding comprises a dissociation constant (Kt or Kp) of 1 nM or lower, 100 pM or lower; or 10 pM or lower. In some embodiments, a DBD of a synTF of the disclosure binds to a specific DBM target sequence with a dissociation constant (Kt) of 500 nM or lower, or 100 nM or lower, or 1 nM or lower, or 1 pM or lower, or 0.1 pM or lower, or even 10 fM or lower.

By "non-target" it is meant that the nucleic acid sequence concerned is not appreciably bound by the relevant DBD of the synTF. In some embodiments it may be considered that, where a DBD of the synTF as described herein has a known sequence-specific target sequence, all other nucleic acid sequences may be considered to be non-target sequences. From a practical perspective it can be convenient to define an interaction between a non-target sequence and a particular DBD of the synTF as being sub-physiological (i.e. not capable of creating a physiological response under physiological target sequence/DBD concentrations). For example, if any binding can be measured between the DBD of the synTF and the non-target sequence, the dissociation constant (Kd) is typically weaker than 1 μM, such as 10 μM or weaker, 100 μM or weaker, or at least 1 mM.

The term "high affinity" refers to a binding affinity correlating with a lower value range Kd (e.g., Kt or Kp) value, e.g., a lower Kd value than that for a low-affinity binding agent. In some embodiments, a high-affinity DBD of a synTF of the disclosure binds to a specific DBM target sequence with a dissociation constant (Kt) of 50 nM or lower, or 40 nM or lower, or 30 nM or lower, or 20 nM or lower, or 10 nM or lower, or 5 nM or lower, or 4 nM or lower, or 3 nM or lower, or 2 nM or lower, or 1 nM or lower, or 0.5 nM or lower, or 0.1 nM or lower, or 0.01 nM or lower. In one embodiment, a synTF that binds to a DBD with high affinity comprises a Kt in the range of 0.5-50 nM (e.g., 0.5-40 nM, 0.5-30 nM, 0.5-20 nM, 0.5-10 nM, 0.5-5 nM, 0.5-4 nM, 0.5-3 nM, 0.5-2 nM, 1-50 nM, 1-40 nM, 1-30 nM, 1-20 nM, 1-10 nM, 1-5 nM, 1-4 nM, 1-3 nM, 1-2 nM, 5-50 nM, 5-40 nM, 5-30 nM, 5-20 nM, 5-10 nM, 10-50 nM, 10-40 nM, 10-30 nM, 10-20 nM, 25-50 nM, 25-40 nM, 25-30 nM, 30-50 nM, 30-40 nM, 40-50 nM or any range therebetween.

The term "low affinity" refers to a binding affinity correlating with a higher Kd value or range of values (e.g., Kt or Kp) value, e.g., a higher Kd value than a that of a synTF that binds with high-affinity to its binding partner. In some embodiments, a low-affinity DBD of a synTF of the disclosure binds to a specific DBM target sequence with a dissociation constant (Kt) of 5 nM or higher, or 10 nM or higher, or 50 nM or higher, or 100 nM or higher, or 200 nM or higher, or 300 nM or higher, or 400 nM or higher, or 500 nM or higher (see e.g., Example 8, Table 6). In one embodiment, a synTF that binds a DBD with low affinity comprises a Kt in the range of 5-500 nM (e.g., between 10-500 nM, 10-400 nM, 10-300 nM, 10-200 nM, 10-100 nM, 10-50 nM, 10-25 nM, 25-500 nM, 25-400 nM, 25-300 nM, 25-200 nM, 25-100 nM, 25-50 nM, 50-500 nM, 50-400 nM, 50-300 nM, 50-200 nM, 50-100 nM, 100-500 nM, 100-400 nM, 100-300 nM, 100-200 nM, 200-500 nM, 200-400 nM, 200-300 nM, 300-500 nM, 300-400 nM, 400-500 nM or any range therebetween.

The term “amino acid” in the context of the present disclosure is used in its broadest sense and is meant to include naturally occurring L α-amino acids or residues. The commonly used one and three letter abbreviations for naturally occurring amino acids are used herein: A=Ala: C=Cys; D=Asp; E=Glu; F=Phe; G=Gly; H=His; I=Ile; K=Lys; L=Leu; M=Met; N=Asn; P=Pro; Q=Gln; R=Arg; S=Ser; T=Thr; V=Val; W=Trp; and Y=Tyr (Lehninger, A. L., (1975) Biochemistry, 2d ed., pp. 71-92, Worth Publishers, New York). The general term “amino acid” further includes D-amino acids, retro-inverso amino acids as well as chemically modified amino acids such as amino acid analogues, naturally occurring amino acids that are not usually incorporated into proteins such as norleucine, and chemically synthesized compounds having properties known in the art to be characteristic of an amino acid, such as β-amino acids. For example, analogues or mimetics of phenylalanine or proline, which allow the same conformational restriction of the peptide compounds as do natural Phe or Pro, are included within the definition of amino acid. Such analogues and mimetics are referred to herein as “functional equivalents” of the respective amino acid. Other examples of amino acids are listed by Roberts and Vellaccio, The Peptides: Analysis, Synthesis, Biology, Gross and Meiehofer, eds., Vol. 5 p. 341, Academic Press, Inc., N.Y. 1983, which is incorporated herein by reference.

The term “peptide” as used herein (e.g., in the context of a synTF or ligand) refers to a plurality of amino acids joined together in a linear or circular chain. The term oligopeptide is typically used to describe peptides having between 2 and about 50 or more amino acids. Peptides larger than about 50 amino acids are often referred to as polypeptides or proteins. For purposes of the present disclosure, however, the term “peptide” is not limited to any particular number of amino acids, and is used interchangeably with the terms “polypeptide” and “protein”.

The terms “nucleic acids” and “nucleotides” refer to naturally occurring or synthetic or artificial nucleic acid or nucleotides. The terms “nucleic acids” and “nucleotides” comprise deoxyribonucleotides or ribonucleotides or any nucleotide analogue and polymers or hybrids thereof in either single- or double-stranded, sense or antisense form. As will also be appreciated by those in the art, many variants of a nucleic acid can be used for the same purpose as a given nucleic acid. Thus, a nucleic acid also encompasses substantially identical nucleic acids and complements thereof. Nucleotide analogues include nucleotides having modifications in the chemical structure of the base, sugar and/or phosphate, including, but not limited to, 5-position pyrimidine modifications, 8-position purine modifications, modifications at cytosine exocyclic amines, substitution of 5-bromo-uracil, and the like; and 2'-position sugar modifications, including but not limited to, sugar-modified ribonucleotides in which the 2'-OH is replaced by a group selected from H, OR, R, halo, SH, SR, NH2, NHR, NR2, or CN. shRNAs also can comprise non-natural elements such as non-natural bases, e.g., inosine and xanthine, non-natural sugars, e.g., 2'-methoxy ribose, or non-natural phosphodiester linkages, e.g., methylphosphonates, phosphorothioates and peptides.

The term “nucleic acid sequence” or “oligonucleotide” or “polynucleotide” are used interchangeably herein and refers to at least two nucleotides covalently linked together. The term “nucleic acid sequence” is also used inter-changeably herein with “gene”, “cDNA”, and “mRNA”. As will be appreciated by those in the art, the depiction of a single nucleic acid sequence also defines the sequence of the complementary nucleic acid sequence. Thus, a nucleic acid sequence also encompasses the complementary strand of a depicted single strand. Unless otherwise indicated, a particular nucleic acid sequence also implicitly encompasses conservatively modified variants thereof (e.g., degenerate codon substitutions) and complementary sequences, as well as the sequence explicitly indicated. As will also be appreciated by those in the art, a single nucleic acid sequence provides a probe that can hybridize to the target sequence under stringent hybridization conditions. Thus, a nucleic acid sequence also encompasses a probe that hybridizes under stringent hybridization conditions. The term “nucleic acid sequence” refers to a single or double-stranded polymer of deoxyribonucleotide or ribonucleotide bases read from the 5'- to the 3'-end. It includes chromosomal DNA, self-replicating plasmids, infectious polymers of DNA or RNA and DNA or RNA that performs a primarily structural role. “Nucleic acid sequence” also refers to a consecutive list of abbreviations, letters, characters or words, which represent nucleotides. Nucleic acid sequences can be single stranded or double stranded, or can contain portions of both double stranded and single stranded sequence. The nucleic acid sequence can be DNA, both genomic and cDNA, RNA, or a hybrid, where the nucleic acid sequence can contain combinations of deoxyribo- and ribo-nucleotides, and combinations of bases including uracil, adenine, thymine, cytosine, guanine, inosine, xanthine hypoxanthine, isocytosine and isoguanine. Nucleic acid sequences can be obtained by chemical synthesis methods or by recombinant methods. A nucleic acid sequence will generally contain phosphodiester bonds, although nucleic acid analogs can be included that can have at least one different linkage, e.g., phosphoramidate, phosphorothioate, phosphorodithioate, or O-methylphosphoroamidite linkages and peptide nucleic acid backbones and linkages in the nucleic acid sequence. Other analog nucleic acids include those with positive backbones; non-ionic backbones, and non-ribose backbones, including those described in U.S. Pat. Nos. 5,235,033 and 5,034,506, which are incorporated by reference. Nucleic acid sequences containing one or more non-naturally occurring or modified nucleotides are also included within one definition of nucleic acid sequences. The modified nucleotide analog can be located for example at the 5'-end and/or the 3'-end of the nucleic acid sequence. Representative examples of nucleotide analogs can be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino) propyl uridine, 5-bromo uridine; adenosines and guanosines modified at the 8-position, e.g. 8-bromo guanosine; deaza nucleotides, e.g. 7 deaza-adenosine; 0- and N-alkylated nucleotides, e.g. N6-methyl adenosine are suitable. The 2' OH— group can be replaced by a group selected from H. OR, R. halo, SH, SR, NH2, NHR, NR2 or CN, wherein R is C-C6 alkyl, alkenyl or alkynyl and halo is F, Cl, Br or I. Modifications of the ribose-phosphate backbone can be done for a variety of reasons, e.g., to increase the stability and half-life of such molecules in physiological environments or as probes on a biochip. Mixtures of naturally occurring nucleic acids and analogs can be used; alternatively, mixtures of different nucleic acid analogs, and mixtures of naturally occurring nucleic acids and analogs can be used. Nucleic acid sequences include but are not limited to, nucleic acid sequence encoding proteins, for example that act as transcriptional repressors, antisense molecules, ribozymes, small inhibitory nucleic acid sequences, for example but not limited to RNAi, shRNAi, siRNA, micro RNAi (mRNAi), antisense oligonucleotides etc.

The term "oligonucleotide" as used herein refers to an oligomer or polymer of ribonucleic acid (RNA) or deoxyribonucleic acid (DNA) or mimetics thereof, as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. An oligonucleotide preferably includes two or more nucleomonomers covalently coupled to each other by linkages (e.g., phosphodiesters) or substitute linkages.

In its broadest sense, the term "substantially complementary", when used herein with respect to a nucleotide sequence in relation to a reference or target nucleotide sequence, means a nucleotide sequence having a percentage of identity between the substantially complementary nucleotide sequence and the exact complementary sequence of said reference or target nucleotide sequence of at least 60%, at least 70%, at least 80% or 85%, at least 90%, at least 93%, at least 95% or 96%, at least 97% or 98%, at least 99% or 100% (the latter being equivalent to the term "identical" in this context). For example, identity is assessed over a length of at least 10 nucleotides, or at least 11, 12, 13, 14, 15, 16, 17, 18, 19, 20, 21, 22 or up to 50 nucleotides of the entire length of the nucleic acid sequence to said reference sequence (if not specified otherwise below). Sequence comparisons are carried out using default GAP analysis with the University of Wisconsin GCG, SEQWEB application of GAP, based on the algorithm of Needleman and Wunsch (Needleman and Wunsch (1970) J Mol. Biol. 48: 443-453; as defined above). A nucleotide sequence "substantially complementary" to a reference nucleotide sequence hybridizes to the reference nucleotide sequence under low stringency conditions, preferably medium stringency conditions, most preferably high stringency conditions (as defined above).

In its broadest sense, the term "substantially identical", when used herein with respect to a nucleotide sequence, means a nucleotide sequence corresponding to a reference or target nucleotide sequence, wherein the percentage of identity between the substantially identical nucleotide sequence and the reference or target nucleotide sequence is at least 60%, at least 70%, at least 80% or 85%, at least 90%, at least 93%, at least 95% or 96%, at least 97% or 98%, at least 99% or 100% (the latter being equivalent to the term "identical" in this context). For example, identity is assessed over a length of 10-22 nucleotides, such as at least 10, 11, 12, 13, 14, 15, 16, 17, 18, 19, 20, 21, 22 or up to 50 nucleotides of a nucleic acid sequence to said reference sequence (if not specified otherwise below). Sequence comparisons are carried out using default GAP analysis with the University of Wisconsin GCG, SEQWEB application of GAP, based on the algorithm of Needleman and Wunsch (Needleman and Wunsch (1970) J Mol. Biol. 48: 443-453; as defined above). A nucleotide sequence that is "substantially identical" to a reference nucleotide sequence hybridizes to the exact complementary sequence of the reference nucleotide sequence (i.e. its corresponding strand in a double-stranded molecule) under low stringency conditions, preferably medium stringency conditions, most preferably high stringency conditions (as defined above). Homologues of a specific nucleotide sequence include nucleotide sequences that encode an amino acid sequence that is at least 24% identical, at least 35% identical, at least 50% identical, at least 65% identical to the reference amino acid sequence, as measured using the parameters described above, wherein the amino acid sequence encoded by the homolog has the same biological activity as the protein encoded by the specific nucleotide. The term "substantially non-identical" refers to a nucleotide sequence that does not hybridize to the nucleic acid sequence under stringent conditions.

As used herein, the term "gene" refers to a nucleic acid sequence comprising an open reading frame encoding a polypeptide, including both exon and (optionally) intron sequences. A "gene" refers to coding sequence of a gene product, as well as non-coding regions of the gene product, including 5'UTR and 3'UTR regions, introns and the promoter of the gene product. A "gene", as used herein, is the segment of nucleic acid (typically DNA) that is involved in producing a polypeptide or ribonucleic acid gene product. It includes regions preceding and following the coding region (leader and trailer) as well as intervening sequences (introns) between individual coding segments (exons). Conveniently, this term also includes the necessary control sequences for gene expression (e g enhancers, silencers, promoters, terminators etc.), which may be adjacent to or distant to the relevant coding sequence, as well as the coding and/or transcribed regions encoding the gene product. These definitions generally refer to a single-stranded molecule, but in specific embodiments will also encompass an additional strand that is partially, substantially or fully complementary to the single-stranded molecule. Thus, a nucleic acid sequence can encompass a double-stranded molecule or a double-stranded molecule that comprises one or more complementary strand(s) or "complement(s)" of a particular sequence comprising a molecule. As used herein, a single stranded nucleic acid can be denoted by the prefix "ss", a double stranded nucleic acid by the prefix "ds", and a triple stranded nucleic acid by the prefix "ts."

As used herein, the term "vector" is used interchangeably with "plasmid" to refer to a nucleic acid molecule capable of transporting another nucleic acid to which it has been linked. Vectors capable of directing the expression of genes and/or nucleic acid sequence to which they are operatively linked are referred to herein as "expression vectors." In general, expression vectors of utility in the methods and engineered genetic counters described herein are often in the form of "plasmids," which refer to circular double stranded DNA loops which, in their vector form are not bound to the chromosome.

The terms "synthetic gene circuit" or "response promoter element" are used interchangeably herein and refer to a nucleic acid construct containing a promoter sequence that has at least one target DNA binding motif (DBM) sequence operably linked upstream of the promoter sequence such that the target DBM sequence confer a responsive property to the promoter when the DBM sequence is bound by its respective DNA binding domain (DBD) of the synthetic transcription factor, the responsive property being whether gene transcription initiation from that promoter is enhanced or repressed when the upstream nearby DBM target sequences are bound by a DBD of the synthetic transcription factor. There may be more than one DBM target sequence operably linked upstream of the promoter sequence. When there is one DBM target sequence, the promoter is referred to a "1×" promoter, where the "1×" refers to the number of DBM target sequence present in the promoter construct. For example, a 4× responsive promoter would be identified as having four DBM target sequences in the engineered response promoter construct, and the four DBM target sequences are upstream of the promoter sequence.

As used herein, a "promoter" refers to a control region of a nucleic acid sequence at which initiation and rate of transcription of the remainder of a nucleic acid sequence are controlled. A promoter may also contain sub-regions at which regulatory proteins and molecules may bind, such as RNA polymerase and other transcription factors. Promoters may be constitutive, inducible, activatable, repressible, tissue-specific or any combination thereof. In some embodiments, the promoter is constitutive. In some embodiments, the promoter is inducible. In some embodiments, the promoter is a mammalian promoter. As discussed herein, a promoter can be applied in any type of cassettes. Promoters are located near the transcription start sites of genes, on the same strand and upstream on the DNA.

As used herein, an "inducible promoter" is one that is characterized by initiating or enhancing transcriptional activity when in the presence of, influenced by or contacted by an inducer or inducing agent. An "inducer" or "inducing agent" with respect to an inducible promoter, may be endogenous or a normally exogenous compound or protein that is administered in such a way as to be active in inducing transcriptional activity from the inducible promoter.

If a promoter is an "inducible promoter", as defined herein, then the rate of transcription is modified in response to an inducing agent or inducer. In contrast, the rate of transcription is not regulated by an inducer if the promoter is a constitutive promoter. The term "constitutive" when made in reference to a promoter means that the promoter is capable of directing transcription of an operably linked nucleic acid sequence in the absence of a stimulus (e.g., heat shock, chemicals, agents, light, etc.). Typically, constitutive promoters are capable of directing expression of a nucleic acid sequence in substantially any cell and any tissue. In contrast, the term "regulatable" or "inducible" promoter referred to herein is one which is capable of directing a level of transcription of an operably linked nucleic acid sequence in the presence of a stimulus (e.g., heat shock, chemicals, light, agent etc.) which is different from the level of transcription of the operably linked nucleic acid sequence in the absence of the stimulus.

The term "operatively linked" or "operable linkage" are used interchangeably herein, are to be understood as meaning, for example, the sequential arrangement of a regulatory element (e.g. a promoter) with a nucleic acid sequence to be expressed and, if appropriate, further regulatory elements (such as, e.g., a terminator) in such a way that each of the regulatory elements can fulfill its intended function to allow, modify, facilitate or otherwise influence expression of the linked nucleic acid sequence. The expression may result depending on the arrangement of the nucleic acid sequences in relation to sense or antisense RNA. To this end, direct linkage in the chemical sense is not necessarily required. Genetic control sequences such as, for example, enhancer sequences, can also exert their function on the target sequence from positions which are further away, or indeed from other DNA molecules. In some embodiments, arrangements are those in which the nucleic acid sequence to be expressed recombinantly is positioned behind the sequence acting as promoter, so that the two sequences are linked covalently to each other. The distance between the promoter sequence and the nucleic acid sequence to be expressed recombinantly can be any distance, and in some embodiments is less than 200 base pairs, especially less than 100 base pairs, less than 50 base pairs. In some embodiments, the nucleic acid sequence to be transcribed is located behind the promoter in such a way that the transcription start is identical with the desired beginning of the chimeric RNA of the invention. Operable linkage, and an expression construct, can be generated by means of customary recombination and cloning techniques as described (e.g., in Maniatis T, Fritsch E F and Sambrook J (1989) Molecular Cloning: A Laboratory Manual, $2^{nd}$ Ed., Cold Spring Harbor Laboratory, Cold Spring Harbor (N.Y.); Silhavy et al. (1984) Experiments with Gene Fusions, Cold Spring Harbor Laboratory, Cold Spring Harbor (N.Y.); Ausubel et al. (1987) Current Protocols in Molecular Biology, Greene Publishing Assoc and Wiley Interscience; Gelvin et al. (Eds) (1990) Plant Molecular Biology Manual; Kluwer Academic Publisher, Dordrecht, The Netherlands). However, further sequences may also be positioned between the two sequences. The insertion of sequences may also lead to the expression of fusion proteins, or serve as Ribosome binding sites. In some embodiments, the expression construct, consisting of a linkage of promoter and nucleic acid sequence to be expressed, can exist in a vector integrated form and be inserted into a plant genome, for example by transformation.

As used herein, the term "operably linked" when used in context of the DBM target sequences described herein or the promoter sequence (RNA polymerase binding site) in a nucleic acid construct or synthetic gene circuit, a responsive reporter, and in an engineered transcription unit means that the DBM target sequences and the promoters are in-frame and in proper spatial and distance away from a nucleic acid coding for a protein or peptide or an RNA to permit the effects of the respective binding by transcription factors or RNA polymerase on transcription.

As used herein, the term "responsive" in the context of a promoter of a synthetic gene circuit, the term refers to whether gene transcription initiation from the promoter is enhanced or repressed when upstream nearby DBM target sequences are bound by their DBD of the synthetic transcription factors.

The terms "promoter," "promoter element," or "promoter sequence" are equivalents and as used herein, refer to a DNA sequence which when operatively linked to a nucleotide sequence of interest is capable of controlling the transcription of the nucleotide sequence of interest into mRNA. A promoter is typically, though not necessarily, located 5' (i.e., upstream) of a nucleotide sequence of interest (e.g., proximal to the transcriptional start site of a structural gene) whose transcription into mRNA it controls, and provides a site for specific binding by RNA polymerase and other transcription factors for initiation of transcription. A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety). Suitable promoters can be derived from genes of the host cells where expression should occur or from pathogens for the host cells (e.g., tissue promoters or pathogens like viruses).

A promoter may be regulated in a tissue-specific or tissue preferred manner such that it is only active in transcribing the associated coding region in a specific tissue type(s). The term “tissue specific” as it applies to a promoter refers to a promoter that is capable of directing selective expression of a nucleotide sequence of interest to a specific type of tissue (e.g., liver) in the relative absence of expression of the same nucleotide sequence of interest in a different type of tissue (e.g., kidney). Tissue specificity of a promoter may be evaluated by, for example, operably linking a reporter gene to the promoter sequence to generate a reporter construct, introducing the reporter construct into the genome of an organism, e.g. an animal model such that the reporter construct is integrated into every tissue of the resulting transgenic animal, and detecting the expression of the reporter gene (e.g., detecting mRNA, protein, or the activity of a protein encoded by the reporter gene) in different tissues of the transgenic animal. The detection of a greater level of expression of the reporter gene in one or more tissues relative to the level of expression of the reporter gene in other tissues shows that the promoter is specific for the tissues in which greater levels of expression are detected. The term “cell type specific” as applied to a promoter refers to a promoter, which is capable of directing selective expression of a nucleotide sequence of interest in a specific type of cell in the relative absence of expression of the same nucleotide sequence of interest in a different type of cell within the same tissue. The term “cell type specific” when applied to a promoter also means a promoter capable of promoting selective expression of a nucleotide sequence of interest in a region within a single tissue. Cell type specificity of a promoter may be assessed using methods well known in the art, e.g., GUS activity staining or immunohistochemical staining. The term “minimal promoter” as used herein refers to the minimal nucleic acid sequence comprising a promoter element while also maintaining a functional promoter. A minimal promoter may comprise an inducible, constitutive or tissue-specific promoter.

The term “expression” as used herein refers to the biosynthesis of a gene product, preferably to the transcription and/or translation of a nucleotide sequence, for example an endogenous gene or a heterologous gene, in a cell. For example, in the case of a heterologous nucleic acid sequence, expression involves transcription of the heterologous nucleic acid sequence into mRNA and, optionally, the subsequent translation of mRNA into one or more polypeptides. Expression also refers to biosynthesis of an RNAi molecule, which refers to expression and transcription of an RNAi agent such as siRNA, shRNA, and antisense DNA but does not require translation to polypeptide sequences. The term “expression construct” and “nucleic acid construct” as used herein are synonyms and refer to a nucleic acid sequence capable of directing the expression of a particular nucleotide sequence, such as the heterologous target gene sequence in an appropriate host cell (e.g., a prokaryotic cell, eukaryotic cell, or mammalian cell). If translation of the desired heterologous target gene is required, it also typically comprises sequences required for proper translation of the nucleotide sequence. The coding region may code for a protein of interest but may also code for a functional RNA of interest, for example antisense RNA, dsRNA, or a nontranslated RNA, in the sense or antisense direction. The nucleic acid construct as disclosed herein can be chimeric, meaning that at least one of its components is heterologous with respect to at least one of its other components.

The term “leakiness” or “leaky” as used in reference to “promoter leakiness” refers to some level of expression of the nucleic acid sequence which is operatively linked to the promoter, even when the promoter is not intended to result in expression of the nucleic acid sequence (i.e., when the promoter is in the “off” state, a background level of expression of the nucleic acid sequence which is operatively linked to such promoter exists). In one illustrative example using inducible promoters, for example a Tet-on promoter, a leaky promoter is where some level of the nucleic acid sequence expression (which is operatively linked to the Tet-on promoter) still occurs in the absence of the inducer agent, tetracycline. Typically, most inducible promoters and tissue-specific promoters have approximately 10%-30% or 10-20% unintended or background nucleic acid sequence expression when the promoter is not active, for example, the background of leakiness of nucleic acid sequence expression is about 10%-20% or about 10-30%. As an illustrative example using a tissue-specific promoter, a “leaky promoter” is one in which expression of the nucleic acid sequence occurs in tissue where a tissue-specific promoter is not active, i.e. expression occurs in a non-specific tissue. Stated in another way using a kidney-specific promoter as an example; if at least some level of the nucleic acid sequence expression occurs in at least one tissue other than the kidney, where the nucleic acid sequence is operably linked to a kidney specific promoter, the kidney specific promoter would be considered a leaky promoter.

The term “enhancer” refers to a cis-acting regulatory sequence involved in the transcriptional activation of a nucleic acid sequence. An enhancer can function in either orientation and can be upstream or downstream of the promoter. As used herein, the term “gene product(s)” is used to refer to include RNA transcribed from a gene, or a polypeptide encoded by a gene or translated from RNA. A protein and/or peptide or fragment thereof can be any protein of interest, for example, but not limited to; mutated proteins; therapeutic proteins; truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, tribodies, humanized proteins, humanized antibodies, chimeric antibodies, modified proteins and fragments thereof.

The terms “nucleic acid construct” or “engineered construct” or “synthetic gene circuit” as used herein refer to a nucleic acid at least partly created by recombinant methods. The term “DNA construct” refers to a polynucleotide construct consisting of deoxyribonucleotides. The construct can be single or double stranded. The construct can be circular or linear. A person of ordinary skill in the art is familiar with a variety of ways to obtain and generate a DNA construct. Constructs can be prepared by means of customary recombination and cloning techniques as are described, for example, in Maniatis T, Fritsch EF and Sambrook J (1989) Molecular Cloning: A Laboratory Manual, 2$^{nd}$ Ed., Cold Spring Harbor Laboratory, Cold Spring Harbor (N.Y.); Silhavy et al. (1984) Experiments with Gene Fusions, Cold Spring Harbor Laboratory, Cold Spring Harbor (N.Y.); Ausubel et al. (1987) Current Protocols in Molecular Biology, Greene Publishing Assoc and Wiley Interscience; Gelvin et al. (Eds) (1990) Plant Molecular Biology Manual; Kluwer Academic Publisher, Dordrecht, The Netherlands.

The terms “polypeptide”, “peptide”, “oligopeptide”, “polypeptide”, “gene product”, “expression product” and “protein” are used interchangeably herein to refer to a polymer or oligomer of consecutive amino acid residues.

The term “in vivo” refers to assays or processes that occur in or within an organism, such as a multicellular animal. In some of the aspects described herein, a method or use can be said to occur “in vivo” when a unicellular organism, such as bacteria, is used. The term “ex vivo” refers to methods and uses that are performed using a living cell with an intact membrane that is outside of the body of a multicellular animal or plant, e.g., explants, cultured cells, including primary cells and cell lines, transformed cell lines, and extracted tissue or cells, including blood cells, among others. The term “in vitro” refers to assays and methods that do not require the presence of a cell with an intact membrane, such as cellular extracts, and can refer to the introducing an engineered genetic counter in a non-cellular system, such as a media not comprising cells or cellular systems, such as cellular extracts.

The terms “decrease”, “reduced”, “reduction”, or “inhibit” are all used herein to mean a decrease by a statistically significant amount. In some embodiments, “reduce,” “reduction” or “decrease” or “inhibit” typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, “reduction” or “inhibition” does not encompass a complete inhibition or reduction as compared to a reference level. “Complete inhibition” is a 100% inhibition as compared to a reference level.

The terms “increased”, “increase”, “enhance”, or “activate” are all used herein to mean an increase by a statically significant amount. In some embodiments, the terms “increased”, “increase”, “enhance”, or “activate” can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

Other than in the operating examples, or where otherwise indicated, all numbers expressing quantities of ingredients or reaction conditions used herein should be understood as modified in all instances by the term “about.” The term “about” when used in connection with percentages can mean 1%.

As used herein the term “comprising” or “comprises” is used in reference to compositions, methods, and respective component(s) thereof, that are essential to the method or composition, yet open to the inclusion of unspecified elements, whether essential or not.

The term “consisting of” refers to compositions, methods, and respective components thereof as described herein, which are exclusive of any element not recited in that description of the embodiment.

As used herein the term “consisting essentially of” refers to those elements required for a given embodiment. The term permits the presence of elements that do not materially affect the basic and novel or functional characteristic(s) of that embodiment.

The singular terms “a,” “an,” and “the” include plural referents unless context clearly indicates otherwise. Similarly, the word “or” is intended to include “and” unless the context clearly indicates otherwise. Although methods and materials similar or equivalent to those described herein can be used in the practice or testing of this disclosure, suitable methods and materials are described below. The abbreviation, “e.g.” is derived from the Latin exempli gratia, and is used herein to indicate a non-limiting example. Thus, the abbreviation “e.g.” is synonymous with the term “for example.”

The technology may be as described in any one of the following numbered Embodiments:

Embodiment 1: An engineered genetic construct comprising a heterologous nucleic acid construct comprising, in the 5' to 3' direction; a first transcription module comprising: a first promoter, a nucleotide sequence encoding a target nucleic acid (TNA) operatively linked to the first promoter; and a second transcriptional module, comprising: a second promoter in the antisense direction to the first promoter, a DNA binding motif (DBM) orientated in the antisense direction to the GOI, wherein the DBM comprises a target nucleic acid for binding of the at least one DBD of a synthetic transcription factor (synTF), the SynTF comprising: i) at least one DNA-binding domain (DBD), ii) at least one Transcription activation (TA) domain, and iii) at least one nuclear localization domain, wherein the nuclear localization domain sequesters the synTF in the cytosol in the absence of an inducer, and wherein in the presence of an inducer, the nuclear localization domain moves to the cytosol in the presence of the inducer.

Embodiment 2: The engineered genetic construct of Embodiment 1, wherein the second transcriptional module further comprises a SynTF-mediated nucleic acid sequence (SynTF-MNAS), wherein the SynTF-MNAS is operatively linked to the second promoter and encodes at least one antisense nucleic acid sequence directed against at least a portion of the TNA, and wherein the SynTF-MNAS is located 3' of the TNA and 5' of the second promoter.

Embodiment 3: The engineered genetic construct of Embodiment 2, wherein antisense nucleic acid sequence is selected from any of: a RNAi molecule, shRNA, siRNA, and miRNA.

Embodiment 4: The engineered genetic construct of Embodiment 2, wherein the second transcriptional module further comprises a SynTF-mediated nucleic acid sequence (SynTF-MNAS), wherein the SynTF-MNAS is operatively linked to the second promoter and encodes a nucleic acid sequence that encodes a double stranded RNA (dsRNA) molecule that hybridizes with at least a portion of the target nucleic acid sequence, wherein the dsRNA molecule comprises at least one nucleic acid change as compared to the nucleic acid sequence of the TNA.

Embodiment 5: The engineered genetic construct of any of Embodiments 2-4, further comprising a Ribosome entry (RZ) site located 3' of the TNA and 5' of the second promoter sequence.

Embodiment 6: The engineered genetic construct of any of Embodiments 1-5, wherein the first and second promoters are selected from any of: constitutive promoters, inducible promoters or tissue specific promoters.

Embodiment 7: The engineered genetic construct of Embodiment 6, wherein the first and second promoters are selected from a group consisting of SV40, CMV, UBC, EF1A, PGK and CAGG.

Embodiment 8: The engineered genetic construct of Embodiment 6, wherein the first and second promoters are the same promoter.

Embodiment 9: The engineered genetic construct of Embodiment 6, wherein the first and second promoters are different promoters.

Embodiment 10: The engineered genetic construct of any of Embodiments 1-9, wherein the DBD is selected from a group consisting of helix-turn-helix domain, zinc-finger binding domain, leucine zipper, winged helix domain, winged helix-turn-helix domain, helix-loop-helix domain, HMG-box domain, Wor3 domain, or OB-fold domain.

Embodiment 11: The engineered genetic construct of Embodiment 10, wherein the DBD is a zinc-finger binding domain.

Embodiment 12: The engineered genetic construct of any of Embodiments 1-11, wherein the TA domain is selected from a group consisting of acidic domains, glutamine-rich domains, proline-rich domains, and isoleucine-rich domains.

Embodiment 13: The engineered genetic construct of Embodiment 12, wherein the TA domain is selected from acidic domains.

Embodiment 14: The engineered genetic construct of Embodiment 13, wherein the TA domain is VP64.

Embodiment 15: The engineered genetic construct of any of Embodiments 1-14, wherein the nuclear localization domain is ERT2.

Embodiment 16: The engineered genetic construct of any of Embodiments 1-15, wherein the inducer is 4-OHT.

Embodiment 17: A vector comprising the engineered genetic construct of any of Embodiments 1-16.

Embodiment 18: The vector of Embodiment 17, further comprising a third promoter operatively linked to a heterologous nucleic acid encoding a synthetic transcription factor (synTF), wherein the synTF comprises; at least one DNA-binding domain (DBD), at least one Transcription activation (TA) domain, and at least one nuclear localization domain, and wherein when the synTF is expressed, the nuclear localization domain sequesters the synTF in the cytosol in the absence of an inducer, and wherein in the presence of an inducer, the nuclear localization domain moves to the cytosol in the presence of the inducer.

Embodiment 19: The vector of Embodiments 17 or 18, wherein the third promoter is selected from any of: constitutive promoters, inducible promoters or tissue specific promoters.

Embodiment 20: The vector of any of Embodiments 17-19, wherein the third promoter is selected from a group consisting of SV40, CMV, UBC, EF1A, PGK and CAGG.

Embodiment 21: The vector of any of Embodiments 17-20, wherein the first, second, and third promoters are the same promoter.

Embodiment 22: The vector of any of Embodiments 17-21, wherein the first, second, and third promoters are different promoters.

Embodiment 23: The vector of any of Embodiments 17-22, wherein the inducer is 4-OHT.

Embodiment 24: A cell comprising the engineered construct of any of Embodiments 1-16 or the vector of Embodiments 17 or 18.

Embodiment 25: The cell of Embodiment 24, wherein the cell further comprises at least one synthetic transcription factor (synTF), or a nucleic acid construct encoding a synTF, wherein the synTF comprises; at least one DNA-binding domain (DBD), at least one Transcription activation (TA) domain, and at least one nuclear localization domain, wherein the nuclear localization domain sequesters the synTF in the cytosol in the absence of an inducer, and wherein in the presence of an inducer, the nuclear localization domain moves to the cytosol in the presence of the inducer.

Embodiment 26: The cell of Embodiment 21, wherein the inducer is 4-OHT.

Embodiment 27: A composition comprising then engineered genetic construct of any of Embodiments 1-16, the vector of Embodiment 17, or the cell of Embodiment 24.

Embodiment 28: A system for regulating the expression of a target nucleic acid sequence (TNA) comprising: a) a synthetic transcription factor (synTF) comprising: i) at least one DNA-binding domain (DBD), ii) at least one Transcription activation (TA) domain, and iii) at least one nuclear localization domain, wherein the nuclear localization domain sequesters the synTF in the cytosol in the absence of an inducer, and wherein in the presence of an inducer, the nuclear localization domain moves to the cytosol in the presence of the inducer; and b) an engineered genetic construct comprising, in the 5' to 3' direction a first transcription module and a second transcription module, i) the first transcription module comprising: a first promoter and a nucleotide sequence encoding a target nucleic acid sequence (TNA) operatively linked to the first promoter, and ii) the second transcriptional module, comprising: a second promoter in the antisense direction to the first promoter, a DNA binding motif (DBM) orientated in the antisense direction to the TNA, wherein the DBM comprises a target nucleic acid for binding of the at least one DBD of the SynTF; wherein, in the absence of the inducer, the synTF is sequestered in the cytosol, preventing the DBD of the synTF from binding to the DBM, and preventing the TA domain from being in proximity to the second promoter sequence, preventing repression of the TNA ("antisense-OFF"), and wherein, in the presence of the inducer, the synTF moves to the nucleus, enabling the DBD to bind to the DNA binding motif (DBM) and enabling the TA domain (ED) to be in proximity to the second promoter sequence to enable the expression of the antisense sequence of the TNA ("antisense-ON").

Embodiment 29: The system of Embodiment 28, wherein in the presence of an inducer, the SynTF-mediated nucleic acid sequence (SynTF-MNAS) is expressed and hybridizes with a portion of the nucleic acid sequence of the TNA, forming a double stranded nucleic acid which is degraded.

Embodiment 30: The system of Embodiment 29, wherein the double stranded nucleic acid allows RNA editing of the TNA and/or a heterologous gene having a sequence at least 98% similar to the TNA.

Embodiment 31: The system of Embodiment 28, wherein the second transcriptional module further comprises a SynTF-mediated nucleic acid sequence (SynTF-MNAS), wherein SynTF-MNAS is operatively linked to the second promoter and encodes at least one antisense nucleic acid sequence directed against at least a portion of the TNA, and wherein the SynTF-MNAS sequence is located 3' of the TNA and 5' of the second promoter.

Embodiment 32: The system of any of Embodiments 28-29, wherein the antisense nucleic acid sequence is selected from any of: a RNAi molecule, shRNA, siRNA, and miRNA.

Embodiment 33: The system of any of Embodiments 28-29, wherein the second transcriptional module further comprises a SynTF-mediated nucleic acid sequence (SynTF-MNAS), wherein the SynTF-MNAS is operatively linked to the second promoter and encodes a nucleic acid sequence that hybridizes with at least a portion of the TNA, wherein the SynTF-MNAS has a nucleic acid change as compared to the TNA.

Embodiment 34: The system of any of Embodiments 28-33, further comprising a Ribosome entry (RZ) site located 3' of the TNA and 5' of the SynTF-MNAS.

Embodiment 35: The system of any of Embodiments 28-34, wherein the first and second promoters are constitutive promoters.

Embodiment 36: The system of any of Embodiments 28-35, wherein the first and second promoters are selected from a group consisting of SV40, CMV, UBC, EF1A, PGK and CAGG.

Embodiment 37: The system of any of Embodiments 28-36, wherein the first and second promoters selected are the same constitutive promoter.

Embodiment 38: The system of any of Embodiments 28-37, wherein the first and second promoter selected are different constitutive promoters.

Embodiment 39: The system of any of Embodiments 28-38, wherein the DBD is selected from a group consisting of helix-turn-helix domain, zinc-finger binding domain, leucine zipper, winged helix domain, winged helix-turn-helix domain, helix-loop-helix domain, HMG-box domain, Wor3 domain, or OB-fold domain.

Embodiment 40: The system of any of Embodiments 28-39, wherein the DBD is a zinc-finger binding domain.

Embodiment 41: The system of any of Embodiments 28-40, wherein the TA domain is selected from a group consisting of acidic domains, glutamine-rich domains, proline-rich domains, and isoleucine-rich domains.

Embodiment 42: The system of any of Embodiments 28-41, wherein the TA domain is selected from acidic domains.

Embodiment 43: The system of any of Embodiments 28-42, wherein the TA domain is VP64.

Embodiment 44: The system of any of Embodiments 28-43, wherein the nuclear localization domain is ERT2.

Embodiment 45: The system of any of Embodiments 28-44, wherein the inducer is 4-OHT.

Embodiment 46: The system of any of Embodiments 28-45, using the engineered genetic construct of any of Embodiments 1-16.

Embodiment 47: The system of any of Embodiments 28-46, wherein the system is performed in a cell according to any of Embodiments 24-26.

Embodiment 48: A method for transiently and reversibly regulating the expression of a gene of interest, the method comprising contacting the cell according to Embodiment 24 or 25 with an inducer molecule.

Embodiment 49: The method of Embodiment 48, wherein the inducer molecule is 4-OHT or variant or homologue thereof.

Definitions of common terms in cell biology and molecular biology can be found in "The Merck Manual of Diagnosis and Therapy", $19^{th}$ Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San diego, USA (1987); current Protocols in Protein Science (CPPS) (John E. Coligan, et. Al., ed., John Wiley and Sons, Inc.), Current Protocols in Cell Biology (CPCB) (Juan S. Bonifacino et. Al. ed., John Wiley and Sons, Inc.), and Culture of Animal Cells: A Manual of Basic Technique by R. Ian Freshney, Publisher: Wiley-Liss; $5^{th}$ edition (2005), Animal Cell Culture Methods (Methods in Cell Biology, Vol. 57, Jennie P. Mather and David Barnes editors, Academic Press, 1' edition, 1998) which are all incorporated by reference herein in their entireties.

EXAMPLES

Regulated Transcriptional Repressor System

Synthetic transcriptional circuits have advanced the capabilities and safety of cell-based therapeutics. In order to advance the precision and tunability of these circuits, the inventors have developed a small-molecule inducible mRNA anti-sense repressor switch or 'off switch'. Here, the inventors demonstrate functional compositions and methods encompassing a synthetic transcription factor (synTF) comprising a human genome orthogonal zinc-finger array and a drug-inducible translocation system, which was demonstrated to be able to achieve robust and temporary repression of a transgene.

While there are several synthetic transcriptional repressor systems which exist (https://doi.org/10.1038/s41592-020-0966-x, https://doi.org/10.1030/nprot.2013.132), the inventors have improved upon such systems in that the current technology described herein is unique due to at least the following: (i) the ability to control this gene repression with an inducible molecule, e.g., a small molecules, (ii) ease and modular nature of repressor design, and (ii) the transient and reversible nature of the inducible gene repression.

Technical Description

Herein, by way of an example only, a small-molecule inducible transcriptional repressor system was developed which was demonstrated to be able to robustly and transiently silence transgene expression in mammalian cells. The exemplary system works as follows: In the absence of the inducer molecule 4-OHT, the ERT2 keeps the synTF in the cytoplasm, therefore preventing the occurrence of anti-sense repression of the GOI (FIG. 3A). However in the presence of the inducer molecule, 4-OHT, the cytoplasmic sequestering domain, ERT2 enables the synTF to shuttle to the nucleus where it binds to the DNA binding motif (DBM) and induces transcription of anti-sense mRNA to the gene of interest (GOI) (AS-GOI) (FIG. 3B). The anti-sense transcript (AS-GOI) mediates mRNA silencing via mRNA degradation or mRNA decay leading to repression of the expression of the GOI (FIG. 3C).

Figure 1:
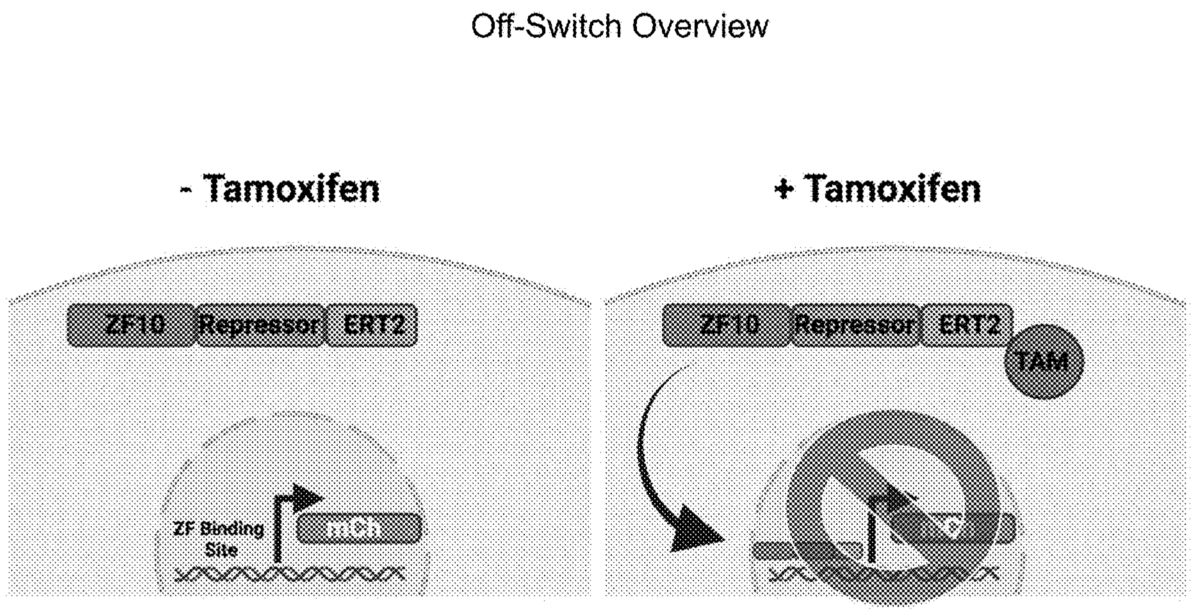
FIG. 1 is a schematics of previous prior-art "off-switch's in the presence and absence of an inducer tamoxifen.
Figure 2A:
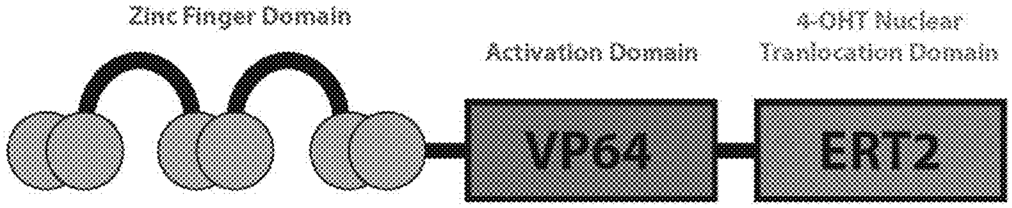
FIG. 2A-2B depicts one embodiment of the synthetic transcription factor (SynTF) and inducible repressor synthetic construct and system.
Figure 2B:

To assess the inducible transcriptional repressor system, the inventors initially used two vectors. One vector comprises a synthetic inducible repressor construct as defined herein, which compromises a gene of interest (GOI) operatively linked to a constitutive promoter, and downstream, a second transcription unit comprising, in brief, a second promoter, and a binding site for the synTF (e.g., DBM or the DNA binding domain). The second vector encoding the inducible synTF (e.g., small molecule induced synTF) comprising a transcriptional activation domain, DNA-binding domain (DBD) and a nuclear localization domain (or cytosolic domain). First, to construct the nucleic acid encoding the small-molecule inducer synTF, one of our artificial zinc finger proteins was attached (see U.S. Pat. No. 10,138,493 B2 and Patent Application No. US 2020/0377564 A1, incorporated herein by reference) to both a VP64 transcriptional domain and ERT2 domain (FIG. 2A). To assess the inducer-dependent, synTF mediated transcriptional repression of the GOI, an engineered construct comprising a constitutively expressed mCherry fluorescent reporter, operatively connected to a constitutive promoter was created, which had, downstream a minimal promoter and an inverted zinc finger binding array (ZF-BD) (also referred to as a DNA binding motif (DBM) (FIG. 4A).

To evaluate the kinetics of this inducible antisense repressor switch, 293T cells were transduced with the vector encoding the synTF and the inducible transcriptional repressor construct to generate a reporter cell line that stably expresses both the inducible synTF and fluorescent reporter. To determine whether the repressor switch was able to transiently silence the GOI mRNA, the cells were treated with three concentrations of 4-OHT and mCherry reporter was measured fluorescence at 1 day, 2 days, and 3 days (FIG. 5A-5B). Next, to determine whether the inducible synTF repressor switch could transiently represses the expression of the GOI, 4-OHT was removed and measured fluorescence expression after 2 days, 4 days, 6 days, and 8 days (FIG. 5B). It was demonstrated that the activation of the synTF by the 4-OT inducer molecule resulted in strong repression (approx. 80% repression) of mCherry expression at all concentrations after 3 days (FIG. 5A) and that mCherry expression was fully restored back to 100% of baseline levels by 8 days post 4-OHT removal with 0.1 M 4-OHT treatment (FIG. 5B). These data validate the anti-sense inducible repressor circuit and system as a robust, and inducible transient repression system.

As discussed herein, the inducible transcriptional repressor constructs used in the Examples and shown in FIG. 4A are exemplary systems. As the inducible transcriptional repressor system is modular in nature, the elements can be readily substituted for alternative elements known in the art. For example, the heterologous nucleic acid can further comprise a nucleic acid comprising a third promoter (e.g., a constitutive promoter) operatively linked to a nucleic acid encoding the synTF as defined herein, thus enabling an all-in-one construct, rather than using two vectors as described in the Examples. The first promoter and the third promoters can be constitutive promoters, and can, in some embodiments, be the same promoter.

Moreover, the Examples demonstrate use of a heterologous nucleic acid construct as an exemplary inducible transcriptional repressor construct comprising, in the 5' to 3' direction; a first transcription module comprising: a first constitutive promoter, a nucleotide sequence encoding a target nucleic acid (TNA) operatively linked to the first promoter; and a second transcriptional module, comprising: a second promoter (e.g., a minimal promoter) in the antisense direction to the first promoter, a DNA binding motif (DBM) for binding of the (inducer) activated synTF that is also orientated in the antisense direction to the GOI. Encompassed herein are modifications to the inducible transcriptional repressor construct used in the Examples to comprise features described in the specification, including, for example, but not limited to (i) one or more GOI (where the GOI can be, e.g., any therapeutic and/or prophylactic molecule), (ii) substitution of the first and/or second promoter for a different promoter, (iii) addition of a nucleic acid encoding one or more an antisense molecule to the GOI (AS-GOI) or synTF-mediated nucleic acid sequence (synTF-MNAS), (iv) more than one DBM to one or more synTF, where the synTF can be activated by different inducer molecules, (v) insertion of spacers and or ribosome entry sites (RZ) between the GOI and the AS-GOI or synTF-MNAS, and other modifications that can be readily made by a person of ordinary skill in the art.

Other exemplary modifications to the synthetic inducible-repressor construct are shown in FIGS. 13A, 13B, and 13C. For example, in some embodiments, a synthetic inducible-repressor construct can comprise a second transcription unit comprising, in the following order: (i) a synTF binding site (e.g., DBM), which is located downstream of the GOI and in the same orientation as the GOI, and (ii) a promoter (e.g., a minimal promoter) also in the same orientation as the first promoter, which is operatively linked to a (iii) a nucleic acid sequence encoding a RNA polymerase III and (iv) a nucleic acid encoding either a RNAi molecule (e.g., GOI shRNA) and/or a RNA editing molecule (e.g., GOI RNA editing molecule), see, e.g., FIG. 12A-12B. Without wishing to be bound by theory, such an embodiment where the second transcription unit is in tandem, and in same orientation as the first transcription unit enables the synTF-induced expression of the GOI shRNA or GOI RNA editing molecule (both of which effectively function as SynTF-MNAS) to form a dsRNA molecule with a portion of the GOI mRNA expressed from the first transcription unit, which can be recognized by a RNA gene editing molecule for RNA editing, e.g., using the CRISPR interference (CRISPi) editing mechanism for sequence specific control of gene expression, as disclosed in International Patent application WO2022/032397, and Larson et al., 2013, Nat Protocols, 2180-2196 and Alerasool et al., Nat. Methods 2020, 1093-1096 (each of which are incorporated herein in their entirety by reference).

As disclosed herein, an inducible synTF for use in the methods, compositions and systems herein comprises at least one DNA-binding domain (DBD), at least one Transcription activation (TA) domain, and at least regulator protein (e.g., at least one nuclear localization domain), wherein the nuclear localization domain sequesters the synTF in the cytosol in the absence of an inducer, and in the presence of an inducer, the nuclear localization domain moves to the cytosol in the presence of the inducer. Herein in the Examples, an exemplary synTF is used comprising a chimeric fusion protein comprising in the following order (i) ZF BD as the DBD, (ii) VP64 as an exemplary transactivation domain (TA) and (iii) ERT2 as an exemplary inducible regulator protein, e.g. a cytosolic sequestering domain (also referred to as a nuclear localization domain). It is envisioned that a person of ordinary skill can readily substitute each of these elements and still maintain the function of the inducible synTF. For example, the ZF can substituted and readily bind to DMB. In some embodiments, VP64 can be readily substituted for alternative transactivation domains (TA) as described herein in the specification, including, but not limited to p65 and/or VPR or any disclosed in Section III(B) herein. Similarly, ERT3 can be readily substituted by one of ordinary skill in the art for a different inducible regulator protein, as disclosed in section III(C) herein, including any regulatable protein disclosed in U.S. Pat. No. 11,530,246, which is incorporated in its entirety herein. As such, the synTF can be modified to be activated by a variety of different inducer molecules, e.g., additional small molecule inducers (e.g., but not limited to Tetracycline, Caffeine, Abscisic Acid), light gated activation (e.g., but not limited to Optogenetic CRY2/CIB1), cellular environment factor induction (e.g., but not limited to HIF1a, NFkB, ARG1), GPCR activation induced (e.g., but not limited to TANGO), and surface receptor activation (e.g., but not limited to TCR activation, SynNotch). Other transaction domains are also encompassed, including RNA pol III transaction domain (RNA Pol III TAD) as disclosed in FIGS. 12C and 12D.

Figure 12C:
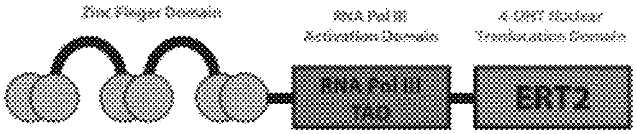
Figure 12D:
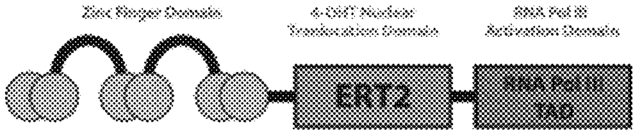

Furthermore, in some embodiments, the order of the domains in the synTF can be modified, for example a synTF as shown in FIG. 12C comprises a synTF that comprises the elements: DBD-TA-regulator protein (RP), which is embodied as DBD-[RNA Pol III TAD]-ERT2. FIG. 12D shows an alternative configuration for the synTF, comprising the elements: DBD-RP-TA, which is embodied as DBD-ERT2-[RNA Pol III TAD].

POSSIBLE VARIATIONS

There are many variants which could be developed from this initial design such as alterations to the transcriptional machinery, genetic payload and induction system. For the transcriptional machinery, variants could encompass use of mammalian transcriptional activation domains in place of VP64 (p65, VPR) stronger or weaker constitutive promoters (hPGK, CAG, SFFV), and DNA binding domain variants (Zinc Fingers, Gal4, Tetracycline Responsive Element). For the genetic payload, variants could include secreted cytokine (IL-2, IL-12, IL-18, Interferon Gamma), antibodies (anti-CD19, anti-CD47, anti-PD1), or additional genetic switches (Transcription Factors). For the induction system, additional small molecule inducers (Tetracycline, Caffeine, Abscisic Acid), light gated activation (Optogenetic CRY2/CIB1), cellular environment factor induction (HIF1a, NFkB, ARG1), GPCR activation induced (TANGO), and surface receptor activation (TCR activation, SynNotch) could be tailored to induce anti-sense mediated repression of the genetic payload.

REFERENCES

All references disclosed herein in the specification and Examples are incorporated in their entirety by reference.

1. Alerasool, N., Segal, D., Lee, H. et al. An efficient KRAB domain for CRISPRi applications in human cells. *Nat Methods* 17, 1093-1096 (2020). doi.org/10.1038/s41592-020-0966-x.
2. Larson, M., Gilbert, L., Wang, X. et al. CRISPR interference (CRISPRi) for sequence-specific control of gene expression. *Nat Protoc* 8, 2180-2196 (2013). doi.org/10.1038/nprot.2013.132
3. U.S. patent Ser. No. 11/530,246
4. WO2022/032397
5. US2019/0233844
6. US2020/000271
7. U.S. Pat. No. 10,138,493

SEQUENCE LISTING

```
Sequence total quantity: 78
SEQ ID NO: 1            moltype = DNA  length = 11
FEATURE                 Location/Qualifiers
source                  1..11
                        mol_type = other DNA
                        organism = synthetic construct
SEQUENCE: 1
agagtgagga c                                                      11

SEQ ID NO: 2            moltype = DNA  length = 11
FEATURE                 Location/Qualifiers
source                  1..11
                        mol_type = other DNA
                        organism = synthetic construct
SEQUENCE: 2
acagtgagga c                                                      11

SEQ ID NO: 3            moltype = DNA  length = 11
FEATURE                 Location/Qualifiers
source                  1..11
                        mol_type = other DNA
                        organism = synthetic construct
SEQUENCE: 3
atagtgagga c                                                      11

SEQ ID NO: 4            moltype = DNA  length = 11
FEATURE                 Location/Qualifiers
source                  1..11
                        mol_type = other DNA
                        organism = synthetic construct
SEQUENCE: 4
agacgctgct c                                                      11

SEQ ID NO: 5            moltype = DNA  length = 11
FEATURE                 Location/Qualifiers
source                  1..11
                        mol_type = other DNA
                        organism = synthetic construct
SEQUENCE: 5
tgacgctgct c                                                      11

SEQ ID NO: 6            moltype = DNA  length = 11
FEATURE                 Location/Qualifiers
```

-continued

```
source                1..11
                      mol_type = other DNA
                      organism = synthetic construct
SEQUENCE: 6
agacggtgct c                                                          11

SEQ ID NO: 7          moltype = DNA  length = 11
FEATURE               Location/Qualifiers
source                1..11
                      mol_type = other DNA
                      organism = synthetic construct
SEQUENCE: 7
acacgctgct c                                                          11

SEQ ID NO: 8          moltype = DNA  length = 11
FEATURE               Location/Qualifiers
source                1..11
                      mol_type = other DNA
                      organism = synthetic construct
SEQUENCE: 8
agacgctact c                                                          11

SEQ ID NO: 9          moltype = DNA  length = 11
FEATURE               Location/Qualifiers
source                1..11
                      mol_type = other DNA
                      organism = synthetic construct
SEQUENCE: 9
agacgctgct a                                                          11

SEQ ID NO: 10         moltype = DNA  length = 11
FEATURE               Location/Qualifiers
source                1..11
                      mol_type = other DNA
                      organism = synthetic construct
SEQUENCE: 10
agactctgct c                                                          11

SEQ ID NO: 11         moltype = DNA  length = 11
FEATURE               Location/Qualifiers
source                1..11
                      mol_type = other DNA
                      organism = synthetic construct
SEQUENCE: 11
cgaagacgct g                                                          11

SEQ ID NO: 12         moltype = DNA  length = 11
FEATURE               Location/Qualifiers
source                1..11
                      mol_type = other DNA
                      organism = synthetic construct
SEQUENCE: 12
agagtgagga c                                                          11

SEQ ID NO: 13         moltype = DNA  length = 11
FEATURE               Location/Qualifiers
source                1..11
                      mol_type = other DNA
                      organism = synthetic construct
SEQUENCE: 13
acagtgagga c                                                          11

SEQ ID NO: 14         moltype = DNA  length = 11
FEATURE               Location/Qualifiers
source                1..11
                      mol_type = other DNA
                      organism = synthetic construct
SEQUENCE: 14
atagtgagga c                                                          11

SEQ ID NO: 15         moltype = DNA  length = 11
FEATURE               Location/Qualifiers
source                1..11
                      mol_type = other DNA
                      organism = synthetic construct
SEQUENCE: 15
agacgctgct c                                                          11

SEQ ID NO: 16         moltype = DNA  length = 11
```

-continued

```
FEATURE               Location/Qualifiers
source                1..11
                      mol_type = other DNA
                      organism = synthetic construct
SEQUENCE: 16
tgacgctgct t                                                  11

SEQ ID NO: 17         moltype = DNA  length = 11
FEATURE               Location/Qualifiers
source                1..11
                      mol_type = other DNA
                      organism = synthetic construct
SEQUENCE: 17
agacggtgct c                                                  11

SEQ ID NO: 18         moltype = DNA  length = 11
FEATURE               Location/Qualifiers
source                1..11
                      mol_type = other DNA
                      organism = synthetic construct
SEQUENCE: 18
acacgctgct c                                                  11

SEQ ID NO: 19         moltype = DNA  length = 11
FEATURE               Location/Qualifiers
source                1..11
                      mol_type = other DNA
                      organism = synthetic construct
SEQUENCE: 19
agacgctact c                                                  11

SEQ ID NO: 20         moltype = DNA  length = 11
FEATURE               Location/Qualifiers
source                1..11
                      mol_type = other DNA
                      organism = synthetic construct
SEQUENCE: 20
agacgctgct a                                                  11

SEQ ID NO: 21         moltype = DNA  length = 11
FEATURE               Location/Qualifiers
source                1..11
                      mol_type = other DNA
                      organism = synthetic construct
SEQUENCE: 21
agactctgct c                                                  11

SEQ ID NO: 22         moltype = DNA  length = 11
FEATURE               Location/Qualifiers
source                1..11
                      mol_type = other DNA
                      organism = synthetic construct
SEQUENCE: 22
attatgggag a                                                  11

SEQ ID NO: 23         moltype = AA  length = 11
FEATURE               Location/Qualifiers
source                1..11
                      mol_type = protein
                      organism = synthetic construct
SEQUENCE: 23
XCCCXCCCCC X                                                  11

SEQ ID NO: 24         moltype = AA  length = 17
FEATURE               Location/Qualifiers
source                1..17
                      mol_type = protein
                      organism = synthetic construct
VARIANT               1..3
                      note = X can be any amino acid
VARIANT               5..6
                      note = X can be any amino acid.
VARIANT               8..12
                      note = X can be any amino acid.
VARIANT               14..16
                      note = X can be any amino acid
SEQUENCE: 24
XXXCXXCXXX XXHXXXH                                            17
```

-continued

```
SEQ ID NO: 25          moltype = AA  length = 16
FEATURE                Location/Qualifiers
source                 1..16
                       mol_type = protein
                       organism = synthetic construct
SEQUENCE: 25
PGERPFQCRI CMRNFS                                          16

SEQ ID NO: 26          moltype =   length =
SEQUENCE: 26
000

SEQ ID NO: 27          moltype =   length =
SEQUENCE: 27
000

SEQ ID NO: 28          moltype =   length =
SEQUENCE: 28
000

SEQ ID NO: 29          moltype = DNA  length = 10
FEATURE                Location/Qualifiers
source                 1..10
                       mol_type = other DNA
                       organism = synthetic construct
SEQUENCE: 29
gccrccatgg                                                 10

SEQ ID NO: 30          moltype =   length =
SEQUENCE: 30
000

SEQ ID NO: 31          moltype =   length =
SEQUENCE: 31
000

SEQ ID NO: 32          moltype =   length =
SEQUENCE: 32
000

SEQ ID NO: 33          moltype = DNA  length = 10
FEATURE                Location/Qualifiers
source                 1..10
                       mol_type = other DNA
                       organism = synthetic construct
SEQUENCE: 33
gccrccatgg                                                 10

SEQ ID NO: 34          moltype =   length =
SEQUENCE: 34
000

SEQ ID NO: 35          moltype =   length =
SEQUENCE: 35
000

SEQ ID NO: 36          moltype =   length =
SEQUENCE: 36
000

SEQ ID NO: 37          moltype = AA  length = 191
FEATURE                Location/Qualifiers
source                 1..191
                       mol_type = protein
                       organism = synthetic construct
SEQUENCE: 37
DEFPTMVFPS GQISQASALA PAPPQVLPQA PAPAPAPAMV SALAQAPAPV PVLAPGPPQA  60
VAPPAPKPTQ AGEGTLSEAL LQLQFDDEDL GALLGNSTDP AVFTDLASVD NSEFQQLLNQ  120
GIPVAPHTTE PMLMEYPEAI TRLVTGAQRP PDPAPAPLGA PGLPNGLLSG DEDFSSIADM  180
DFSALLSQIS S                                               191

SEQ ID NO: 38          moltype = AA  length = 551
FEATURE                Location/Qualifiers
source                 1..551
                       mol_type = protein
                       organism = Homo sapiens
SEQUENCE: 38
MDELFPLIFP AEPAQASGPY VEIIEQPKQR GMRFRYKCEG RSAGSIPGER STDTTKTHPT  60
IKINGYTGPG TVRISLVTKD PPHRPHPHEL VGKDCRDGFY EAELCPDRCI HSFQNLGIQC  120
```

-continued

```
VKKRDLEQAI SQRIQTNNNP FQVPIEEQRG DYDLNAVRLC FQVTVRDPSG RPLRLPPVLS  180
HPIFDNRAPN TAELKICRVN RNSGSCLGGD EIFLLCDKVQ KEDIEVYFTG PGWEARGSFS  240
QADVHRQVAI VFRTPPYADP SLQAPVRVSM QLRRPSDREL SEPMEFQYLP DTDDRHRIEE  300
KRKRTYETFK SIMKKSPFSG PTDPRPPPRR IAVPSRSSAS VPKPAPQPYP FTSSLSTINY  360
DEFPTMVFPS GQISQASALA PAPPQVLPQA PAPAPAPAMV SALAQAPAPV PVLAPGPPQA  420
VAPPAPKPTQ AGEGTLSEAL LQLQFDDEDL GALLGNSTDP AVFTDLASVD NSEFQQLLNQ  480
GIPVAPHTTE PMLMEYPEAI TRLVTGAQRP PDPAPAPLGA PGLPNGLLSG DEDFSSIADM  540
DFSALLSQIS S                                                       551

SEQ ID NO: 39          moltype = AA  length = 261
FEATURE                Location/Qualifiers
source                 1..261
                       mol_type = protein
                       organism = synthetic construct
SEQUENCE: 39
SQYLPDTDDR HRIEEKRKRT YETFKSIMKK SPFSGPTDPR PPPRRIAVPS RSSASVPKPA  60
PQPYPFTSSL STINYDEFPT MVFPSGQISQ ASALAPAPPQ VLPQAPAPAP APAMVSALAQ  120
APAPVPVLAP GPPQAVAPPA PKPTQAGEGT LSEALLQLQF DDEDLGALLG NSTDPAVFTD  180
LASVDNSEFQ QLLNQGIPVA PHTTEPMLME YPEAITRLVT GAQRPPDPAP APLGAPGLPN  240
GLLSGDEDFS SIADMDFSAL L                                            261

SEQ ID NO: 40          moltype = AA  length = 112
FEATURE                Location/Qualifiers
source                 1..112
                       mol_type = protein
                       organism = synthetic construct
SEQUENCE: 40
SLSEALLQLQ FDDEDLGALL GNSTDPAVFT DLASVDNSEF QQLLNQGIPV APHTTEPMLM  60
EYPEAITRLV TGAQRPPDPA PAPLGAPGLP NGLLSGDEDF SSIADMDFSA LL          112

SEQ ID NO: 41          moltype = AA  length = 162
FEATURE                Location/Qualifiers
source                 1..162
                       mol_type = protein
                       organism = synthetic construct
SEQUENCE: 41
SVLPQAPAPA PAPAMVSALA QAPAPVPVLA PGPPQAVAPP APKPTQAGEG TLSEALLQLQ  60
FDDEDLGALL GNSTDPAVFT DLASVDNSEF QQLLNQGIPV APHTTEPMLM EYPEAITRLV  120
TGAQRPPDPA PAPLGAPGLP NGLLSGDEDF SSIADMDFSA LL                     162

SEQ ID NO: 42          moltype = AA  length = 62
FEATURE                Location/Qualifiers
source                 1..62
                       mol_type = protein
                       organism = synthetic construct
SEQUENCE: 42
SPHTTEPMLM EYPEAITRLV TGAQRPPDPA PAPLGAPGLP NGLLSGDEDF SSIADMDFSA  60
LL                                                                 62

SEQ ID NO: 43          moltype = AA  length = 200
FEATURE                Location/Qualifiers
source                 1..200
                       mol_type = protein
                       organism = synthetic construct
SEQUENCE: 43
SQYLPDTDDR HRIEEKRKRT YETFKSIMKK SPFSGPTDPR PPPRRIAVPS RSSASVPKPA  60
PQPYPFTSSL STINYDEFPT MVFPSGQISQ ASALAPAPPQ VLPQAPAPAP APAMVSALAQ  120
APAPVPVLAP GPPQAVAPPA PKPTQAGEGT LSEALLQLQF DDEDLGALLG NSTDPAVFTD  180
LASVDNSEFQ QLLNQGIPVA                                              200

SEQ ID NO: 44          moltype = AA  length = 150
FEATURE                Location/Qualifiers
source                 1..150
                       mol_type = protein
                       organism = synthetic construct
SEQUENCE: 44
SQYLPDTDDR HRIEEKRKRT YETFKSIMKK SPFSGPTDPR PPPRRIAVPS RSSASVPKPA  60
PQPYPFTSSL STINYDEFPT MVFPSGQISQ ASALAPAPPQ VLPQAPAPAP APAMVSALAQ  120
APAPVPVLAP GPPQAVAPPA PKPTQAGEGT                                   150

SEQ ID NO: 45          moltype = AA  length = 100
FEATURE                Location/Qualifiers
source                 1..100
                       mol_type = protein
                       organism = synthetic construct
SEQUENCE: 45
SQYLPDTDDR HRIEEKRKRT YETFKSIMKK SPFSGPTDPR PPPRRIAVPS RSSASVPKPA  60
PQPYPFTSSL STINYDEFPT MVFPSGQISQ ASALAPAPPQ                        100
```

```
SEQ ID NO: 46          moltype = AA  length = 101
FEATURE                Location/Qualifiers
source                 1..101
                       mol_type = protein
                       organism = synthetic construct
SEQUENCE: 46
SRSSASVPKP APQPYPFTSS LSTINYDEFP TMVFPSGQIS QASALAPAPP QVLPQAPAPA  60
PAPAMVSALA QAPAPVPVLA PGPPQAVAPP APKPTQAGEG T                      101

SEQ ID NO: 47          moltype = AA  length = 119
FEATURE                Location/Qualifiers
source                 1..119
                       mol_type = protein
                       organism = synthetic construct
SEQUENCE: 47
PTQAGEGTLS EALLQLQFDD EDLGALLGNS TDPAVFTDLA SVDNSEFQQL LNQGIPVAPH  60
TTEPMLMEYP EAITRLVTGA QRPPDPAPAP LGAPGLPNGL LSGDEDFSSI ADMDFSALL   119

SEQ ID NO: 48          moltype = AA  length = 190
FEATURE                Location/Qualifiers
source                 1..190
                       mol_type = protein
                       organism = synthetic construct
SEQUENCE: 48
RDSREGMFLP KPEAGSAISD VFEGREVCQP KRIRPFHPPG SPWANRPLPA SLAPTPTGPV  60
HEPVGSLTPA PVPQPLDPAP AVTPEASHLL EDPDEETSQA VKALREMADT VIPQKEEAAI  120
CGQMDLSHPP PRGHLDELTT TLESMTEDLN LDSPLTPELN EILDTFLNDE CLLHAMHIST  180
GLSIFDTSLF                                                         190

SEQ ID NO: 49          moltype = AA  length = 116
FEATURE                Location/Qualifiers
source                 1..116
                       mol_type = protein
                       organism = synthetic construct
SEQUENCE: 49
PLDPAPAVTP EASHLLEDPD EETSQAVKAL REMADTVIPQ KEEAAICGQM DLSHPPPRGH  60
LDELTTTLES MTEDLNLDSP LTPELNEILD TFLNDECLLH AMHISTGLSI FDTSLF      116

SEQ ID NO: 50          moltype = AA  length = 66
FEATURE                Location/Qualifiers
source                 1..66
                       mol_type = protein
                       organism = synthetic construct
SEQUENCE: 50
DLSHPPPRGH LDELTTTLES MTEDLNLDSP LTPELNEILD TFLNDECLLH AMHISTGLSI  60
FDTSLF                                                             66

SEQ ID NO: 51          moltype = AA  length = 126
FEATURE                Location/Qualifiers
source                 1..126
                       mol_type = protein
                       organism = synthetic construct
SEQUENCE: 51
SSLAPTPTGP VHEPVGSLTP APVPQPLDPA PAVTPEASHL LEDPDEETSQ AVKALREMAD  60
TVIPQKEEAA ICGQMDLSHP PPRGHLDELT TTLESMTEDL NLDSPLTPEL NEILDTFLND  120
ECLLHA                                                             126

SEQ ID NO: 52          moltype = AA  length = 101
FEATURE                Location/Qualifiers
source                 1..101
                       mol_type = protein
                       organism = synthetic construct
SEQUENCE: 52
PLDPAPAVTP EASHLLEDPD EETSQAVKAL REMADTVIPQ KEEAAICGQM DLSHPPPRGH  60
LDELTTTLES MTEDLNLDSP LTPELNEILD TFLNDECLLH A                      101

SEQ ID NO: 53          moltype = AA  length = 76
FEATURE                Location/Qualifiers
source                 1..76
                       mol_type = protein
                       organism = synthetic construct
SEQUENCE: 53
SVKALREMAD TVIPQKEEAA ICGQMDLSHP PPRGHLDELT TTLESMTEDL NLDSPLTPEL  60
NEILDTFLND ECLLHA                                                  76

SEQ ID NO: 54          moltype = AA  length = 51
FEATURE                Location/Qualifiers
source                 1..51
                       mol_type = protein
```

-continued

```
                         organism = synthetic construct
SEQUENCE: 54
DLSHPPPRGH LDELTTTLES MTEDLNLDSP LTPELNEILD TFLNDECLLH A           51

SEQ ID NO: 55            moltype = AA  length = 316
FEATURE                  Location/Qualifiers
source                   1..316
                         mol_type = protein
                         organism = synthetic construct
SEQUENCE: 55
GRADALDDFD LDMLGSDALD DFDLDMLGSD ALDDFDLDML GSDALDDFDL DMLINSRSSG  60
SPKKKRKVGS GGGSGGSGSV LPQAPAPAPA PAMVSALAQA PAPVPVLAPG PPQAVAPPAP  120
KPTQAGEGTL SEALLQLQFD DEDLGALLGN STDPAVFTDL ASVDNSEFQQ LLNQGIPVAP  180
HTTEPMLMEY PEAITRLVTG AQRPPDPAPA PLGAPGLPNG LLSGDEDFSS IADMDFSALL  240
SGGGSGGSGS DLSHPPPRGH LDELTTTLES MTEDLNLDSP LTPELNEILD TFLNDECLLH  300
AMHISTGLSI FDTSLF                                                  316

SEQ ID NO: 56            moltype = AA  length = 526
FEATURE                  Location/Qualifiers
source                   1..526
                         mol_type = protein
                         organism = synthetic construct
SEQUENCE: 56
GRADALDDFD LDMLGSDALD DFDLDMLGSD ALDDFDLDML GSDALDDFDL DMLINSRSSG  60
SPKKKRKVGS QYLPDTDDRH RIEEKRKRTY ETFKSIMKKS PFSGPTDPRP PPRRIAVPSR  120
SSASVPKPAP QPYPFTSSLS TINYDEFPTM VFPSGQISQA SALAPAPPQV LPQAPAPAPA  180
PAMVSALAQA PAPVPVLAPG PPQAVAPPAP KPTQAGEGTL SEALLQLQFD DEDLGALLGN  240
STDPAVFTDL ASVDNSEFQQ LLNQGIPVAP HTTEPMLMEY PEAITRLVTG AQRPPDPAPA  300
PLGAPGLPNG LLSGDEDFSS IADMDFSALL GSGSGSRDSR EGMFLPKPEA GSAISDVFEG  360
REVCQPKRIR PFHPPGSPWA NRPLPASLAP TPTGPVHEPV GSLTPAPVPQ PLDPAPAVTP  420
EASHLLEDPD EETSQAVKAL REMADTVIPQ KEEAAICGQM DLSHPPPRGH LDELTTTLES  480
MTEDLNLDSP LTPELNEILD TFLNDECLLH AMHISTGLSI FDTSLF                 526

SEQ ID NO: 57            moltype = AA  length = 11
FEATURE                  Location/Qualifiers
source                   1..11
                         mol_type = protein
                         organism = unidentified
SEQUENCE: 57
DALDDFDLDM L                                                       11

SEQ ID NO: 58            moltype = AA  length = 53
FEATURE                  Location/Qualifiers
source                   1..53
                         mol_type = protein
                         organism = synthetic construct
SEQUENCE: 58
GRADALDDFD LDMLGSDALD DFDLDMLGSD ALDDFDLDML GSDALDDFDL DML         53

SEQ ID NO: 59            moltype = AA  length = 2414
FEATURE                  Location/Qualifiers
source                   1..2414
                         mol_type = protein
                         organism = unidentified
SEQUENCE: 59
MAENVVEPGP PSAKRPKLSS PALSASASDG TDFGSLFDLE HDLPDELINS TELGLTNGGD  60
INQLQTSLGM VQDAASKHKQ LSELLRSGSS PNLNMGVGGP GQVMASQAQQ SSPGLGLINS  120
MVKSPMTQAG LTSPNMGMGT SGPNQGPTQS TGMMNSPVNQ PAMGMNTGMN AGMNPGMLAA  180
GNGQGIMPNQ VMNGSIGAGR GRQNMQYPNP GMGSAGNLLT EPLQQGSPQM GGQTGLRGPQ  240
PLKMGMMNNP NPYGSPYTQN PGQQIGASGL GLQIQTKTVL SNNLSPFAMD KKAVPGGGMP  300
NMGQQPAPQV QQPGLVTPVA QGMGSGAHTA DPEKRKLIQQ QLVLLLHAHK CQRREQANGE  360
VRQCNLPHCR TMKNVLNHMT HCQSGKSCQV AHCASSRQII SHWKNCTRHD CPVCLPLKNA  420
GDKRNQQPIL TGAPVGLGNP SSLGVGQQSA PNLSTVSQID PSSIERAYAA LGLPYQVNQM  480
PTQPQVQAKN QQNQQPGQSP QGMRPMSNMS ASPMGVNGGV GVQTPSLLSD SMLHSAINSQ  540
NPMMSENASV PSLGPMPTAA QPSTTGIRKQ WHEDITQDLR NHLVHKLVQA IFPTPDPAAL  600
KDRRMENLVA YARKVEGDMY ESANNRAEYY HLLAEKIYKI QKELEEKRRT RLQKQNMLPN  660
AAGMVPVSMN PGPNMGQPQP GMTSNGPLPD PSMIRGSVPN QMMPRITPQS GLNQFGQMSM  720
AQPPIVPRQT PPLQHHGQLA QPGALNPPMG YGPRMQQPSN QGQFLPQTQF PSQGMNVTNI  780
PLAPSSGQAP VSQAQMSSSS CPVNSPIMPP GSQGSHIHCP QLPQPALHQN SPSPVPSRTP  840
TPHHTPPSIG AQQPPATTIP APVPTPPAMP PGPQSQALHP PPRQTPTPPT TQLPQQVQPS  900
LPAAPSADQP QQQPRSQQST AASVPTPTAP LLPPQPATPL SQPAVSIEGQ VSNPPSTSST  960
EVNSQAIAEK QPSQEVKMEA KMEVDQPEPA DTQPEDISES KVEDCKMEST ETEERSTELK  1020
TEIKEEEDQP STSATQSSPA PGQSKKKIFK PEELRQALMP TLEALYRQDP ESLPFRQPVD  1080
PQLLGIPDYF DIVKSPMDLS TIKRKLDTGQ YQEPWQYVDD IWLMFNNAWL YNRKTSRVYK  1140
YCSKLSEVFE QEIDPVMQSL GYCCGRKLEF SPQTLCCYGK QLCTIPRDAT YYSYQNRYHF  1200
CEKCFNEIQG ESVSLGDDPS QPQTTINKEQ FSKRKNDTLD PELFVECTEC GRKMHQICVL  1260
HHEIIWPAGF VCDGCLKKSA RTRKENKFSA KRLPSTRLGT FLENRVNDFL RRQNHPESGE  1320
VTVRVVHASD KTVEVKPGMK ARFVDSGEMA ESFPYRTKAL FAFEEIDGVD LCFFGMHVQE  1380
YGSDCPPPNQ RRVYISYLDS VHFFRPKCLR TAVYHEILIG YLEYVKKLGY TTGHIWACPP  1440
```

-continued

```
SEGDDYIFHC HPPDQKIPKP KRLQEWYKKM LDKAVSERIV HDYKDIFKQA TEDRLTSAKE  1500
LPYFEGDFWP NVLEESIKEL EQEEEERKRE ENTSNESTDV TKGDSKNAKK KNNKKTSKNK  1560
SSLSRGNKKK PGMPNVSNDL SQKLYATMEK HKEVFFVIRL IAGPAANSLP PIVDPDPLIP  1620
CDLMDGRDAF LTLARDKHLE FSSLRRAQWS TMCMLVELHT QSQDRFVYTC NECKHHVETR  1680
WHCTVCEDYD LCITCYNTKN HDHKMEKLGL GLDDESNNQQ AAATQSPGDS RRLSIQRCIQ  1740
SLVHACQCRN ANCSLPSCQK MKRVVQHTKG CKRKTNGGCP ICKQLIALCC YHAKHCQENK  1800
CPVPFCLNIK QKLRQQQLQH RLQQAQMLRR RMASMQRTGV VGQQQGLPSP TPATPTTPTG  1860
QQPTTPQTPQ PTSQPQPTPP NSMPPYLPRT QAAGPVSQGK AAGQVTPPTP PQTAQPPLPG  1920
PPPAAVEMAM QIQRAAETQR QMAHVQIFQR PIQHQMPPMT PMAPMGMNPP PMTRGPSGHL  1980
EPGMGPTGMQ QQPPWSQGGL PQPQQLQSGM PRPAMMSVAQ HGQPLNMAPQ PGLGQVGISP  2040
LKPGTVSQQA LQNLLRTLRS PSSPLQQQQV LSILHANPQL LAAFIKQRAA KYANSNPQPI  2100
PGQPGMPQGQ PGLQPPTMPG QQGVHSNPAM QNMNPMQAGV QRAGLPQQQP QQQLQPPMGG  2160
MSPQAQQMNM NHNTMPSQFR DILRRQQMMQ QQQQQGAGPG IGPGMANHNQ FQQPQGVGYP  2220
PQQQQRMQHH MQQMQQGNMG QIGQLPQALG AEAGASLQAY QQRLLQQQMG SPVQPNPMSP  2280
QQHMLPNQAQ SPHLQGQQIP NSLSNQVRSP QPVPSPRPQS QPPHSSPSPR MQPQPSPHHV  2340
SPQTSSPHPG LVAAQANPME QGHFASPDQN SMLSQLASNP GMANLHGASA TDLGLSTDNS  2400
DLNSNLSQST LDIH                                                    2414

SEQ ID NO: 60          moltype = AA  length = 617
FEATURE                Location/Qualifiers
source                 1..617
                       mol_type = protein
                       organism = unidentified
SEQUENCE: 60
IFKPEELRQA LMPTLEALYR QDPESLPFRQ PVDPQLLGIP DYFDIVKSPM DLSTIKRKLD  60
TGQYQEPWQY VDDIWLMFNN AWLYNRKTSR VYKYCSKLSE VFEQEIDPVM QSLGYCCGRK  120
LEFSPQTLCC YGKQLCTIPR DATYYSYQNR YHFCEKCFNE IQGESVSLGD DPSQPQTTIN  180
KEQFSKRKND TLDPELFVEC TECGRKMHQI CVLHHEIIWP AGFVCDGCLK KSARTRKENK  240
FSAKRLPSTR LGTFLENRVN DFLRRQNHPE SGEVTVRVVH ASDKTVEVKP GMKARFVDSG  300
EMAESFPYRT KALFAFEEID GVDLCFFGMH VQEYGSDCPP PNQRRVYISY LDSVHFFRPK  360
CLRTAVYHEI LIGYLEYVKK LGYTTGHIWA CPPSEGDDYI FHCHPPDQKI PKPKRLQEWY  420
KKMLDKAVSE RIVHDYKDIF KQATEDRLTS AKELPYFEGD FWPNVLEESI KELEQEEEER  480
KREENTSNES TDVTKGDSKN AKKKNNKKTS KNKSSLSRGN KKKPGMPNVS NDLSQKLYAT  540
MEKHKEVFFV IRLIAGPAAN SLPPIVDPDP LIPCDLMDGR DAFLTLARDK HLEFSSLRRA  600
QWSTMCMLVE LHTQSQD                                                 617

SEQ ID NO: 61          moltype = AA  length = 308
FEATURE                Location/Qualifiers
source                 1..308
                       mol_type = protein
                       organism = Homo sapiens
SEQUENCE: 61
VNKFLRRQNH PEAGEVFVRV VASSDKTVEV KPGMKSRFVD SGEMSESFPY RTKALFAFEE  60
IDGVDVCFFG MHVQEYGSDC PPPNTRRVYI SYLDSIHFFR PRCLRTAVYH EILIGYLEYV  120
KKLGYVTGHI WACPPSEGDD YIFHCHPPDQ KIPKPKRLQE WYKKMLDKAF AERIIHDYKD  180
IFKQATEDRL TSAKELPYFE GDFWPNVLEE SIKELEQEEE ERKKEESTAA SETTEGSQGD  240
SKNAKKKNNK KTNKNKSSIS RANKKKPSMP NVSNDLSQKL YATMEKHKEV FFVIHLHAGP  300
VINTLPPI                                                           308

SEQ ID NO: 62          moltype = AA  length = 314
FEATURE                Location/Qualifiers
source                 1..314
                       mol_type = protein
                       organism = Drosophila melanogaster
SEQUENCE: 62
VNNFLKKKEA GAGEVHIRVV SSSDKCVEVK PGMRRRFVEQ GEMMNEFPYR AKALFAFEEV  60
DGIDVCFFGM HVQEYGSECP APNTRRVYIA YLDSVHFFRP RQYRTAVYHE ILLGYMDYVK  120
QLGYTMAHIW ACPPSEGDDY IFHCHPTDQK IPKPKRLQEW YKKMLDKGMI ERIIQDYKDI  180
LKQAMEDKLG SAAELPYFEG DFWPNVLEES IKELDQEEEE KRKQAEAAEA AAAANLFSIE  240
ENEVSGDGKK KGQKKAKKSN KSKAAQRKNS KKSNEHQSGN DLSTKIYATM EKHKEVFFVI  300
RLHSAQSAAS LAPI                                                    314

SEQ ID NO: 63          moltype = AA  length = 634
FEATURE                Location/Qualifiers
source                 1..634
                       mol_type = protein
                       organism = Drosophila melanogaster
SEQUENCE: 63
NGKYSDPWEY VDDVWLMFDN AWLYNRKTSR VYRYCTKLSE VFEAEIDPVM QALGYCCGRK  60
YTFNPQVLCC YGKQLCTIPR DAKYYSYQNR YTYCQKCFND IQGDTVTLGD DPLQSQTQIK  120
KDQFKEMKND HLELEPFVNC QECGRKQHQI CVLWLDSIWP GGFVCDNCLK KKNSKRKENK  180
FNAKRLPTTK LGVYIETRVN NFLKKKEAGA GEVHIRVVSS SDKCVEVKPG MRRRFVEQGE  240
MMNEFPYRAK ALFAFEEVDG IDVCFFGMHV QEYGSECPAP NTRRVYIAYL DSVHFFRPRQ  300
YRTAVYHEIL LGYMDYVKQL GYTMAHIWAC PPSEGDDYIF HCHPTDQKIP KPKRLQEWYK  360
KMLDKGMIER IIQDYKDILK QAMEDKLGSA AELPYFEGDF WPNVLEESIK ELDQEEEEKR  420
KQAEAAEAAA AANLFSIEEN EVSGDGKKKG QKKAKKSNKS KAAQRKNSKK SNEHQSGNDL  480
STKIYATMEK HKEVFFVIRL HSAQSAASLA PIQDPDPLLT CDLMDGRDAF LTLARDKHFE  540
FSSLRRAQFS TLSMLYELHN QGQDKFVYTC NHCKTAVETR YHCTVCDDFD LCIVCKEKVG  600
HQHKMEKLGF DIDDGSALAD HKQANPQEAR KQSI                              634
```

-continued

```
SEQ ID NO: 64          moltype = AA  length = 97
FEATURE                Location/Qualifiers
source                 1..97
                       mol_type = protein
                       organism = synthetic construct
SEQUENCE: 64
MDAKSLTAWS RTLVTFKDVF VDFTREEWKL LDTAQQILYR NVMLENYKNL VSLGYQLTKP  60
DVILRLEKGE EPWLVEREIH QETHPDSETA FEIKSSV                          97

SEQ ID NO: 65          moltype = AA  length = 7
FEATURE                Location/Qualifiers
source                 1..7
                       mol_type = protein
                       organism = synthetic construct
SEQUENCE: 65
PKKKRKV                                                           7

SEQ ID NO: 66          moltype = AA  length = 595
FEATURE                Location/Qualifiers
source                 1..595
                       mol_type = protein
                       organism = Homo sapiens
SEQUENCE: 66
MTMTLHTKAS GMALLHQIQG NELEPLNRPQ LKIPLERPLG EVYLDSSKPA VYNYPEGAAY  60
EFNAAAAANA QVYGQTGLPY GPGSEAAAFG SNGLGGFPPL NSVSPSPLML LHPPPQLSPF  120
LQPHGQQVPY YLENEPSGYT VREAGPPAFY RPNSDNRRQG GRERLASTND KGSMAMESAK  180
ETRYCAVCND YASGYHYGVW SCEGCKAFFK RSIQGHNDYM CPATNQCTID KNRRKSCQAC  240
RLRKCYEVGM MKGGIRKDRR GGRMLKHKRQ RDDGEGRGEV GSAGDMRAAN LWPSPLMIKR  300
SKKNSLALSL TADQMVSALL DAEPPILYSE YDPTRPFSEA SMMGLLTNLA DRELVHMINW  360
AKRVPGFVDL TLHDQVHLLE CAWLEILMIG LVWRSMEHPG KLLFAPNLLL DRNQGKCVEG  420
MVEIFDMLLA TSSRFRMMNL QGEEFVCLKS IILLNSGVYT FLSSTLKSLE EKDHIHRVLD  480
KITDTLIHLM AKAGLTLQQQ HQRLAQLLLI LSHIRHMSNK GMEHLYSMKC KNVVPLYDLL  540
LEMLDAHRLH APTSRGGASV EETDQSHLAT AGSTSSHSLQ KYYITGEAEG FPATV       595

SEQ ID NO: 67          moltype = AA  length = 314
FEATURE                Location/Qualifiers
source                 1..314
                       mol_type = protein
                       organism = synthetic construct
SEQUENCE: 67
SAGDMRAANL WPSPLMIKRS KKNSLALSLT ADQMVSALLD AEPPILYSEY DPTRPFSEAS  60
MMGLLTNLAD RELVHMINWA KRVPGFVDLT LHDQVHLLEC AWLEILMIGL VWRSMEHPVK  120
LLFAPNLLLD RNQGKCVEGM VEIFDMLLAT SSRFRMMNLQ GEEFVCLKSI ILLNSGVYTF  180
LSSTLKSLEE KDHIHRVLDK ITDTLIHLMA KAGLTLQQQH QRLAQLLLIL SHIRHMSNKG  240
MEHLYSMKCK NVVPLYDLLL EAADAHRLHA PTSRGGASVE ETDQSHLATA GSTSSHSLQK  300
YYITGEAEGF PATA                                                   314

SEQ ID NO: 68          moltype = AA  length = 314
FEATURE                Location/Qualifiers
source                 1..314
                       mol_type = protein
                       organism = synthetic construct
SEQUENCE: 68
SAGDMRAANL WPSPLMIKRS KKNSLALSLT ADQMVSALLD AEPPILYSEY DPTRPFSEAS  60
MMGLLTNLAD RELVHMINWA KRVPGFVDLT LHDQVHLLEC AWLEILMIGL VWRSMEHPGK  120
LLFAPNLLLD RNQGKCVEGM VEIFDMLLAT SSRFRMMNLQ GEEFVCLKSI ILLNSGVYTF  180
LSSTLKSLEE KDHIHRVLDK ITDTLIHLMA KAGLTLQQQH QRLAQLLLIL SHIRHMSNKR  240
MEHLYSMKCK NVVPLYDLLL EMLDAHRLHA PTSRGGASVE ETDQSHLATA GSTSSHSLQK  300
YYITGEAEGF PATV                                                   314

SEQ ID NO: 69          moltype = AA  length = 314
FEATURE                Location/Qualifiers
source                 1..314
                       mol_type = protein
                       organism = synthetic construct
SEQUENCE: 69
SAGDMRAANL WPSPLMIKRS KKNSLALSLT ADQMVSALLD AEPPILYSEY DPTRPFSEAS  60
MMGLLTNLAD RELVHMINWA KRVPGFVDLT LHDQVHLLEC AWLEILMIGL VWRSMEHPGK  120
LLFAPNLLLD RNQGKCVEGM VEIFDMLLAT SSRFRMMNLQ GEEFVCLKSI ILLNSGVYTF  180
LSSTLKSLEE KDHIHRVLDK ITDTLIHLMA KAGLTLQQQH QRLAQLLLIL SHIRHMSNKG  240
MEHLYSMKCK NVVPLYDLLL EAADAHRLHA PTSRGGASVE ETDQSHLATA GSTSSHSLQK  300
YYITGEAEGF PATA                                                   314

SEQ ID NO: 70          moltype = AA  length = 314
FEATURE                Location/Qualifiers
source                 1..314
                       mol_type = protein
                       organism = synthetic construct
```

```
SEQUENCE: 70
SAGDMRAANL WPSPLMIKRS KKNSLALSLT ADQMVSALLD AEPPILYSEY DPTRPFSEAS  60
MMGLLTNLAD RELVHMINWA KRVPGFVDLT LHDQVHLLEC AWLEILMIGL VWRSMEHPVK  120
LLFAPNLLLD RNQGKCVEGM VEIFDMLLAT SSRFRMMNLQ GEEFVCLKSI ILLNSGVYTF  180
LSSTLKSLEE KDHIHRVLDK ITDTLIHLMA KAGLTLQQQH QRLAQLLLIL SHIRHMSNKG  240
MEHLYSMKCK NVVPLYDAAL EMLDAHRLHA PTSRGGASVE ETDQSHLATA GSTSSHSLQK  300
YYITGEAEGF PATV                                                    314

SEQ ID NO: 71          moltype = AA  length = 306
FEATURE                Location/Qualifiers
source                 1..306
                       mol_type = protein
                       organism = synthetic construct
SEQUENCE: 71
PPQIEEACEL PECQVDAGNK VCNLQCNNHA CGWDGGDCSL NFNDPWKNCT QSLQCWKYFS  60
DGHCDSQCNS AGCLFDGFDC QLTEGQCNPL YDQYCKDHFS DGHCDQGCNS AECEWDGLDC  120
AEHVPERLAA GTLVLVVLLP PDQLRNNSFH FLRELSHVLH TNVVFKRDAQ GQQMIFPYYG  180
HEEELRKHPI KRSTVGWATS SLLPGTSGGR QRRELDPMDI RGSIVYLEID NRQCVQSSSQ  240
CFQSATDVAA FLGALASLGS LNIPYKIEAV KSEPVEPPLP SQLHLMYVAA AAFVLLFFVG  300
CGVLLS                                                             306

SEQ ID NO: 72          moltype = AA  length = 358
FEATURE                Location/Qualifiers
source                 1..358
                       mol_type = protein
                       organism = synthetic construct
SEQUENCE: 72
PCVGSNPCYN QGTCEPTSEN PFYRCLCPAK FNGLLCHILD YSFTGGAGRD IPPPQIEEAC  60
ELPECQVDAG NKVCNLQCNN HACGWDGGDC SLNFNDPWKN CTQSLQCWKY FSDGHCDSQC  120
NSAGCLFDGF DCQLTEGQCN PLYDQYCKDH FSDGHCDQGC NSAECEWDGL DCAEHVPERL  180
AAGTLVLVVL LPPDQLRNNS FHFLRELSHV LHTNVVFKRD AQGQQMIFPY YGHEEELRKH  240
PIKRSTVGWA TSSLLPGTSG GRQRRELDPM DIRGSIVYLE IDNRQCVQSS SQCFQSATDV  300
AAFLGALASL GSLNIPYKIE AVKSEPVEPP LPSQLHLMYV AAAAFVLLFF VGCGVLLS    358

SEQ ID NO: 73          moltype = AA  length = 21
FEATURE                Location/Qualifiers
source                 1..21
                       mol_type = protein
                       organism = synthetic construct
SEQUENCE: 73
HTRTHTGEKP FQCRICMRNF S                                            21

SEQ ID NO: 74          moltype = AA  length = 22
FEATURE                Location/Qualifiers
source                 1..22
                       mol_type = protein
                       organism = synthetic construct
SEQUENCE: 74
HLRTHTGSQK PFQCRICMRN FS                                           22

SEQ ID NO: 75          moltype = AA  length = 21
FEATURE                Location/Qualifiers
source                 1..21
                       mol_type = protein
                       organism = synthetic construct
SEQUENCE: 75
HTRTHTGEKP FQCRICMRNF S                                            21

SEQ ID NO: 76          moltype = AA  length = 22
FEATURE                Location/Qualifiers
source                 1..22
                       mol_type = protein
                       organism = synthetic construct
SEQUENCE: 76
HLRTHTGSQK PFQCRICMRN FS                                           22

SEQ ID NO: 77          moltype = AA  length = 21
FEATURE                Location/Qualifiers
source                 1..21
                       mol_type = protein
                       organism = synthetic construct
SEQUENCE: 77
HTRTHTGEKP FQCRICMRNF S                                            21

SEQ ID NO: 78          moltype = AA  length = 7
FEATURE                Location/Qualifiers
source                 1..7
                       mol_type = protein
                       organism = synthetic construct
```

-continued

```
SEQUENCE: 78
HLRTHLR                                                                    7
```

The invention claimed is:

1. An engineered genetic construct comprising a heterologous nucleic acid construct comprising, in the 5' to 3' direction;

(a) a first transcription module comprising:

(i) a first promoter in a sense orientation, (ii) a nucleotide sequence encoding a target nucleic acid (TNA) operatively linked to the first promoter, wherein the TNA is orientated in the sense orientation; and (b) a second transcriptional module, comprising:

(i) a second promoter in the opposite direction to the first promoter and the TNA, (ii) a SynTF-mediated nucleic acid sequence (SynTF-MNAS), wherein the SynTF-MNAS is operatively linked to the second promoter, wherein the SynTF-MNAS is located 3' of the TNA and 5' of the second promoter, and wherein the SynTF-MNAS encodes:

(A) at least one antisense nucleic acid sequence that can hybridize with at least a portion of the TNA, or (B) a double stranded RNA (dsRNA) molecule that can hybridize with at least a portion of the target nucleic acid sequence; and (iii) a DNA binding motif (DBM) orientated in the antisense direction to the TNA, wherein the DBM comprises a target nucleic acid for binding of an at least one DNA-binding domain (DBD) of a synthetic transcription factor (synTF), the SynTF comprising:

(A) the at least one DBD, (B) at least one Transcription activation (TA) domain, and (C) at least one cytosolic sequestering domain, wherein the cytosolic sequestering domain sequesters the synTF in cytosol of a cell in the absence of an inducer, and wherein in the presence of an inducer, the cytosolic sequestering domain is inhibited or removed, enabling the synTF to move to a nucleus of the cell in the presence of the inducer.

2. The engineered genetic construct of claim 1, wherein antisense nucleic acid sequence is selected from any of: a RNAi molecule, shRNA, siRNA, and miRNA.

3. The engineered genetic construct of claim 1, wherein the dsRNA molecule comprises at least one nucleic acid change as compared to the nucleic acid sequence of the TNA.

4. The engineered genetic construct of claim 1, further comprising a Ribosome entry (RZ) site located 3' of the TNA and 5' of the second promoter sequence.

5. The engineered genetic construct of claim 1, wherein the first and second promoters are selected from any of: constitutive promoters, inducible promoters or tissue specific promoters.

6. The engineered genetic construct of claim 5, wherein the first and second promoters are selected from a group consisting of SV40, CMV, UBC, EF1A, PGK and CAGG.

7. The engineered genetic construct of claim 5, wherein the first and second promoters are the same type of promoter or different types of promoters.

8. The engineered genetic construct of claim 1, wherein the DBD is a zinc-finger binding domain.

9. The engineered genetic construct of claim 1, wherein the TA domain is selected from a group consisting of: acidic domains, glutamine-rich domains, proline-rich domains, and isoleucine-rich domains.

10. The engineered genetic construct of claim 9, wherein the TA domain is selected from acidic domains and VP64.

11. The engineered genetic construct of claim 1, wherein the cytosolic sequestering domain is ERT2.

12. The engineered genetic construct of claim 1, wherein the inducer is 4-OHT.

13. A vector comprising the engineered genetic construct of claim 1.

14. The vector of claim 13, further comprising a third promoter operatively linked to a heterologous nucleic acid encoding a synthetic transcription factor (synTF), wherein the synTF comprises; at least one DNA-binding domain (DBD), at least one Transcription activation (TA) domain, and at least one cytosolic sequestering domain, and wherein when the synTF is expressed, the cytosolic sequestering domain sequesters the synTF in cytosol of a cell in the absence of an inducer, and wherein in the presence of an inducer, the cytosolic sequestering domain is inhibited or removed, enabling the synTF to move to a nucleus of the cell in the presence of the inducer.

15. A system comprising:

a. a synthetic transcription factor (synTF) comprising:

i. at least one DNA-binding domain (DBD), ii. at least one Transcription activation (TA) domain, and iii. at least one cytosolic sequestering domain, wherein the cytosolic sequestering domain sequesters the synTF in cytosol of a cell in the absence of an inducer, and wherein in the presence of an inducer, the cytosolic sequestering is inhibited or removed, enabling the synTF to moves to a nucleus of the cell in the presence of the inducer; and b. an engineered genetic construct comprising, in the 5' to 3' direction a first transcription module and a second transcription module, i. the first transcription module comprising: a first promoter in a sense orientation and operatively linked to a nucleotide sequence encoding a target nucleic acid sequence (TNA), wherein the TNA is orientated in the sense, and ii. the second transcriptional module, comprising:

(A) a second promoter in the opposite direction to the first promoter and the TNA, (B) a SynTF-mediated nucleic acid sequence (SynTF-MNAS) operatively linked to the second promoter, wherein the SynTF-MNAS encodes:

(1) at least one antisense nucleic acid molecule that can hybridize with at least a portion of the TNA; or (2) a double-stranded RNA molecule (dsRNA molecule) that can hybridize with at least a portion of the TNA; and (C) a DNA binding motif (DBM) orientated in the antisense direction to the TNA, wherein the DBM comprises a target nucleic acid for binding of the at least one DBD of the SynTF;

wherein, in the absence of the inducer, the synTF is sequestered in cytosol of the cell, preventing the DBD of the synTF from binding to the DBM, preventing the TA domain from being in proximity to the second promoter sequence, preventing the TA domain from activating transcription of the SynTF-MNAS, and preventing repression or gene-editing of the TNA by the SynTF-MNAS ("SynTF-MNAS OFF"), and wherein, in the presence of the inducer, the synTF moves to a nucleus of the cell, enabling the DBD to bind to the DNA binding motif (DBM), enabling the TA domain to be in proximity to the second promoter sequence, enabling the TA domain to activate transcription of the SynTF-MNAS, and enabling repression or gene-editing of the TNA by the SynTF-MNAS ("SynTF-MNAS ON").

16. The system of claim 15, wherein in the presence of an inducer, the expressed antisense sequence of the TNA hybridizes with a portion of the sense strand of nucleic acid sequence of the TNA to form a double stranded nucleic acid molecule which is degraded.

17. The system of claim 15, wherein in the presence of an inducer, the SynTF-MNAS is expressed and forms a double stranded nucleic acid molecule.

18. The system of claim 15, wherein when the dsRNA molecule is expressed and hybridizes with a portion of the TNA, it forms a double stranded RNA complex with a mismatch with at least a portion of the TNA, where the complex can be recognized and edited by RNA-editing machinery.

19. The system of claim 15, wherein the antisense nucleic acid sequence is selected from any of: a RNAi molecule, shRNA, siRNA, and miRNA.

20. The system of claim 18, wherein the dsRNA molecule has at least one nucleic acid change as compared to the TNA.

21. The system of claim 15, further comprising a Ribosome entry (RZ) site located 3' of the TNA and 5' of the SynTF-MNAS.

22. The system of claim 15, wherein the first and second promoters are constitutive promoters.

23. The system of claim 15, wherein the first and second promoters are selected from a group consisting of SV40, CMV, UBC, EFIA, PGK and CAGG.

24. The system of claim 15, wherein the first and second promoters selected are the same constitutive promoter.

25. The system of claim 15, wherein the first and second promoter selected are different constitutive promoters.

26. The system of claim 15, wherein the DBD is a zinc-finger binding domain.

27. The system of claim 15, wherein the TA domain is VP64.

28. The system of claim 15, wherein the cytosolic sequestering domain is ERT2.

29. The system of claim 15, wherein the inducer is 4-OHT.

30. The engineered genetic construct of claim 1, wherein the DBM of the second transcriptional module enables the TA domain of the SynTF to be in proximity to the second promoter sequence and enables the TA domain of the SynTF to activate transcription of the SynTF-MNAS.

* * * * *